United States Patent
Palczewski

(10) Patent No.: US 11,013,700 B2
(45) Date of Patent: *May 25, 2021

(54) COMPOUNDS AND METHODS OF TREATING OCULAR DISORDERS

(71) Applicant: CASE WESTERN RESERVE UNIVERSITY, Cleveland, OH (US)

(72) Inventor: Krzysztof Palczewski, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/526,662

(22) Filed: Jul. 30, 2019

(65) Prior Publication Data

US 2020/0129453 A1 Apr. 30, 2020

Related U.S. Application Data

(63) Continuation of application No. 15/529,299, filed as application No. PCT/US2015/062343 on Nov. 24, 2015, now Pat. No. 10,363,231.

(60) Provisional application No. 62/083,704, filed on Nov. 24, 2014.

(51) Int. Cl.
| | |
|---|---|
| *A61K 31/13* | (2006.01) |
| *A61K 31/351* | (2006.01) |
| *A61K 31/4406* | (2006.01) |
| *A61K 31/135* | (2006.01) |
| *A61K 31/133* | (2006.01) |
| *A61K 31/137* | (2006.01) |

(52) U.S. Cl.
CPC ............ *A61K 31/13* (2013.01); *A61K 31/133* (2013.01); *A61K 31/135* (2013.01); *A61K 31/137* (2013.01); *A61K 31/351* (2013.01); *A61K 31/4406* (2013.01)

(58) Field of Classification Search
CPC .... A61K 31/13; A61K 31/135; A61K 31/137; A61K 31/4406; A61K 31/133; A61K 31/351; A61P 27/02
See application file for complete search history.

(56) References Cited

U.S. PATENT DOCUMENTS

| | | |
|---|---|---|
| 2009/0197967 A1 | 8/2009 | Kubota et al. |
| 2012/0295895 A1 | 11/2012 | Palczewski et al. |

*Primary Examiner* — Sahar Javanmard

(74) *Attorney, Agent, or Firm* — Tarolli, Sundheim, Covell & Tummino LLP

(57) ABSTRACT

A method of treating an ocular disorder in a subject associated with increased all-trans-retinal in an ocular tissue includes administering to the subject a therapeutically effective amount of a primary amine compound of formula (I):

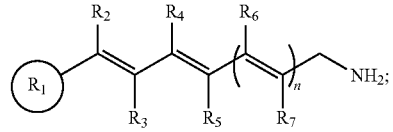

and pharmaceutically acceptable salts thereof.

23 Claims, 6 Drawing Sheets

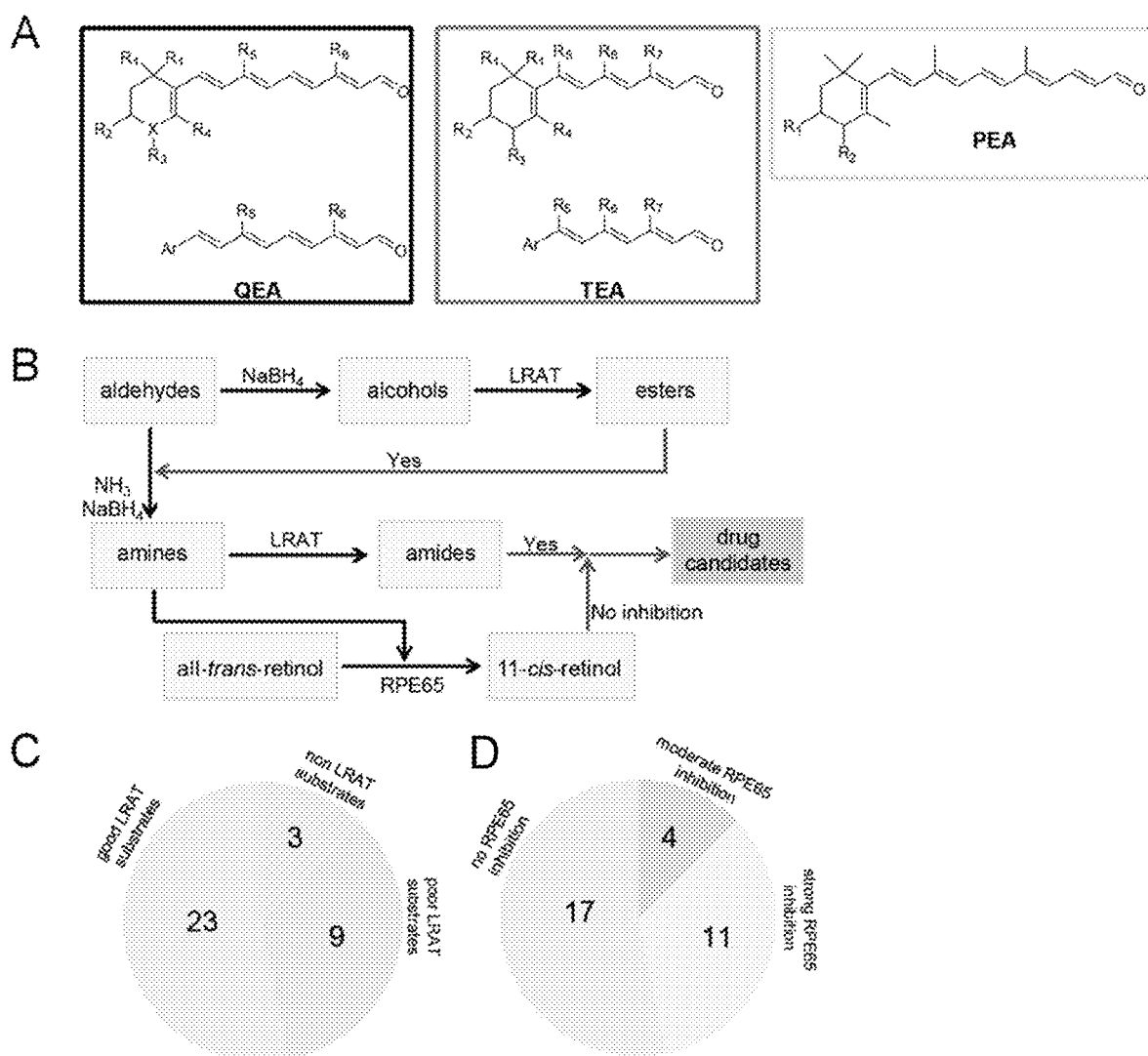
Figs. 2A-D

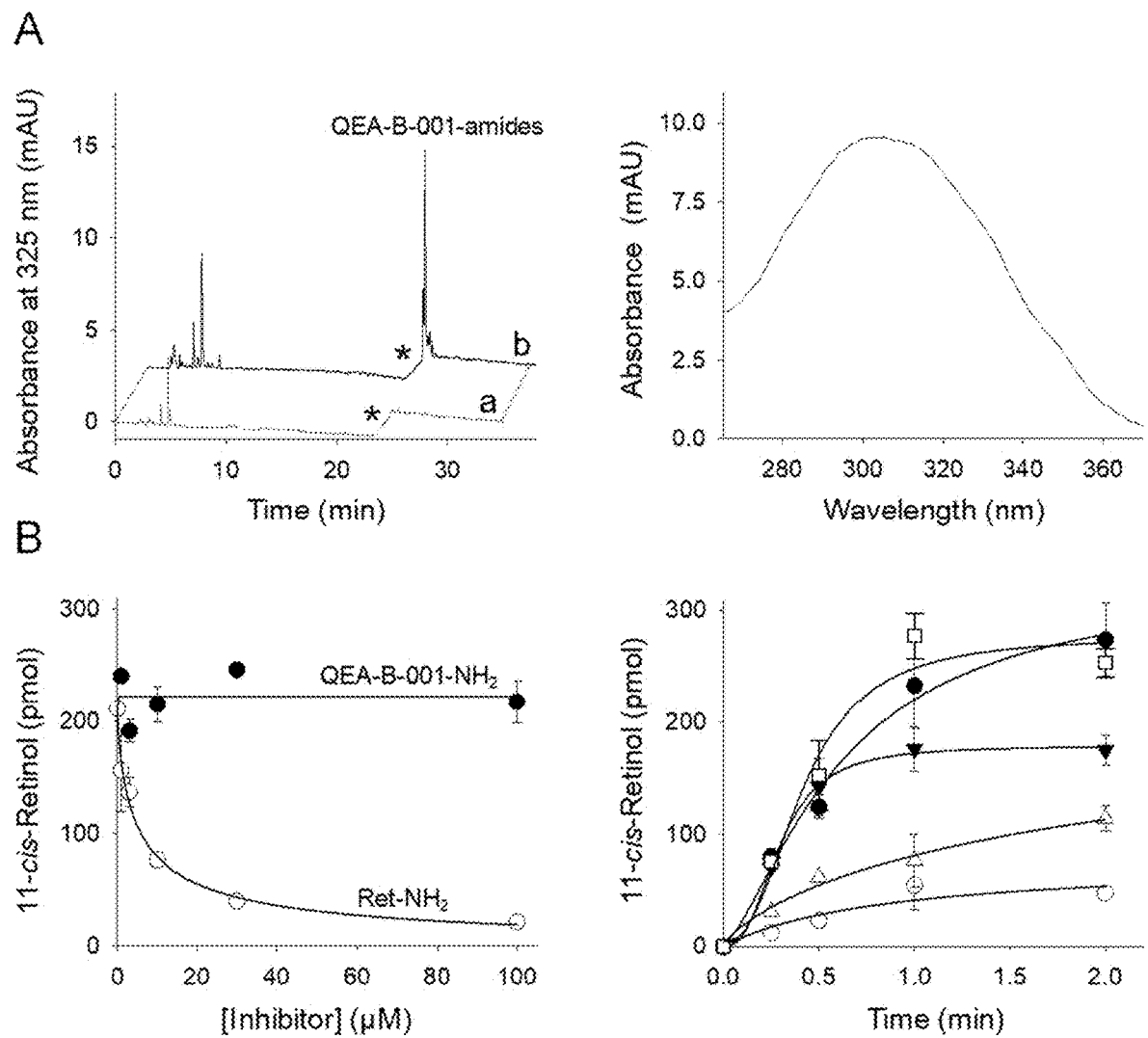
Figs. 3A-B

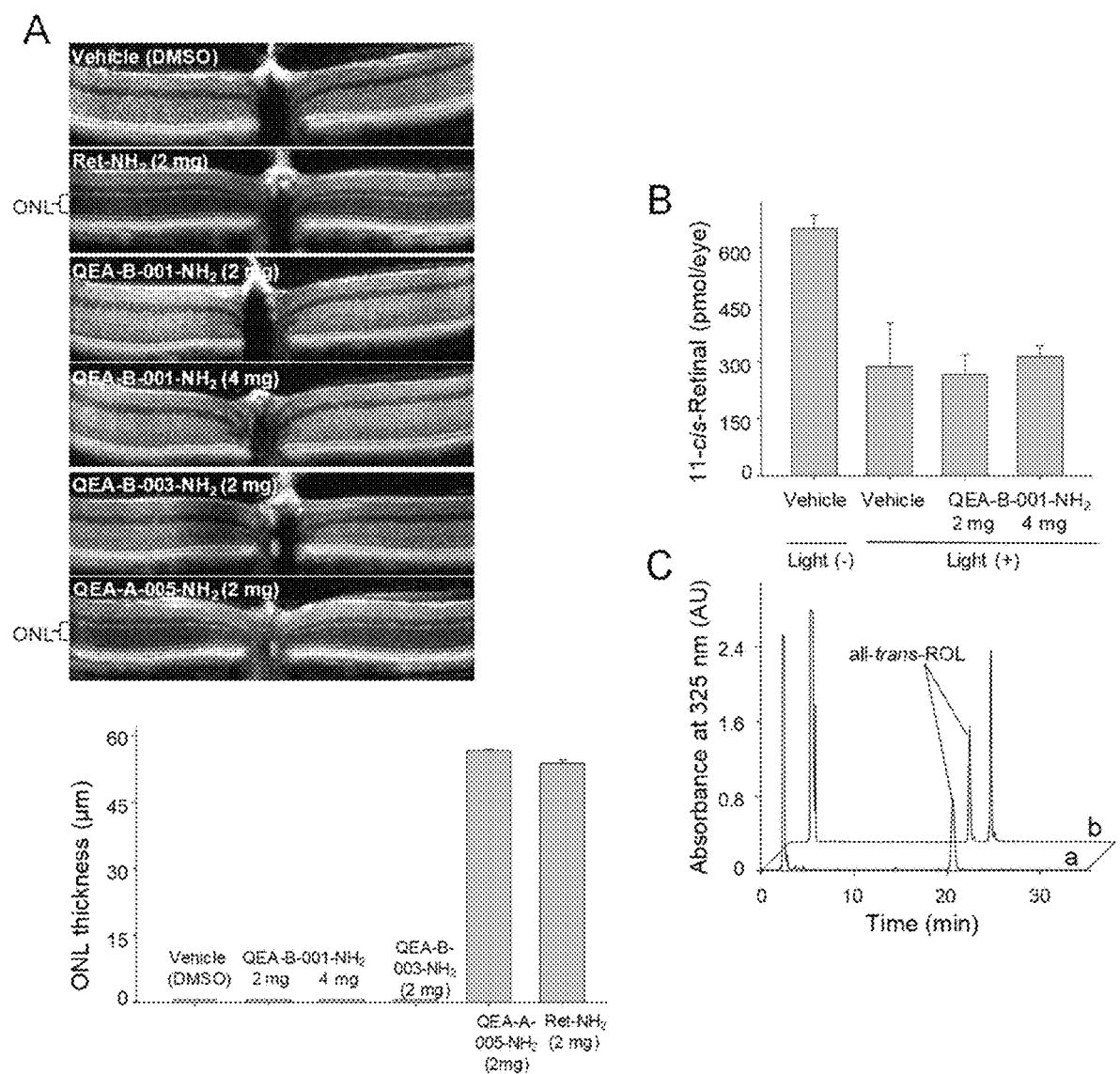
Figs. 4A-C

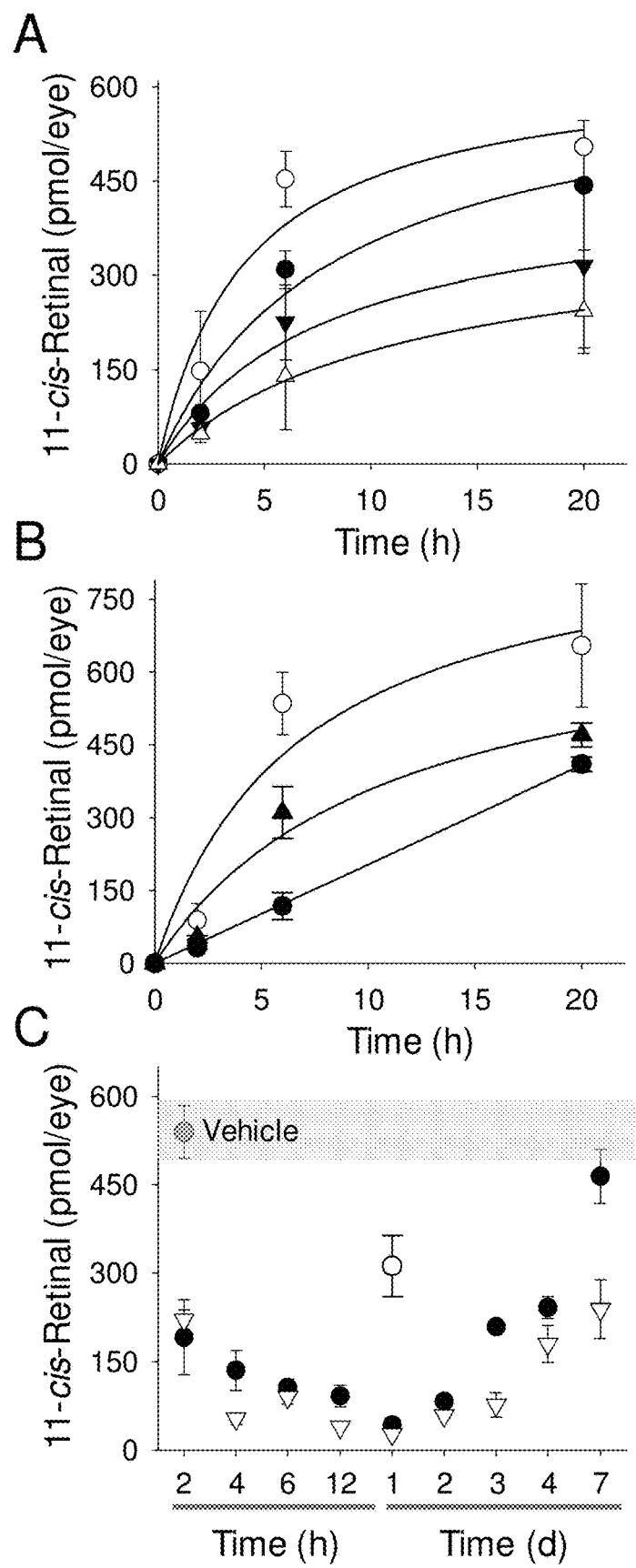
Figs. 5A-C

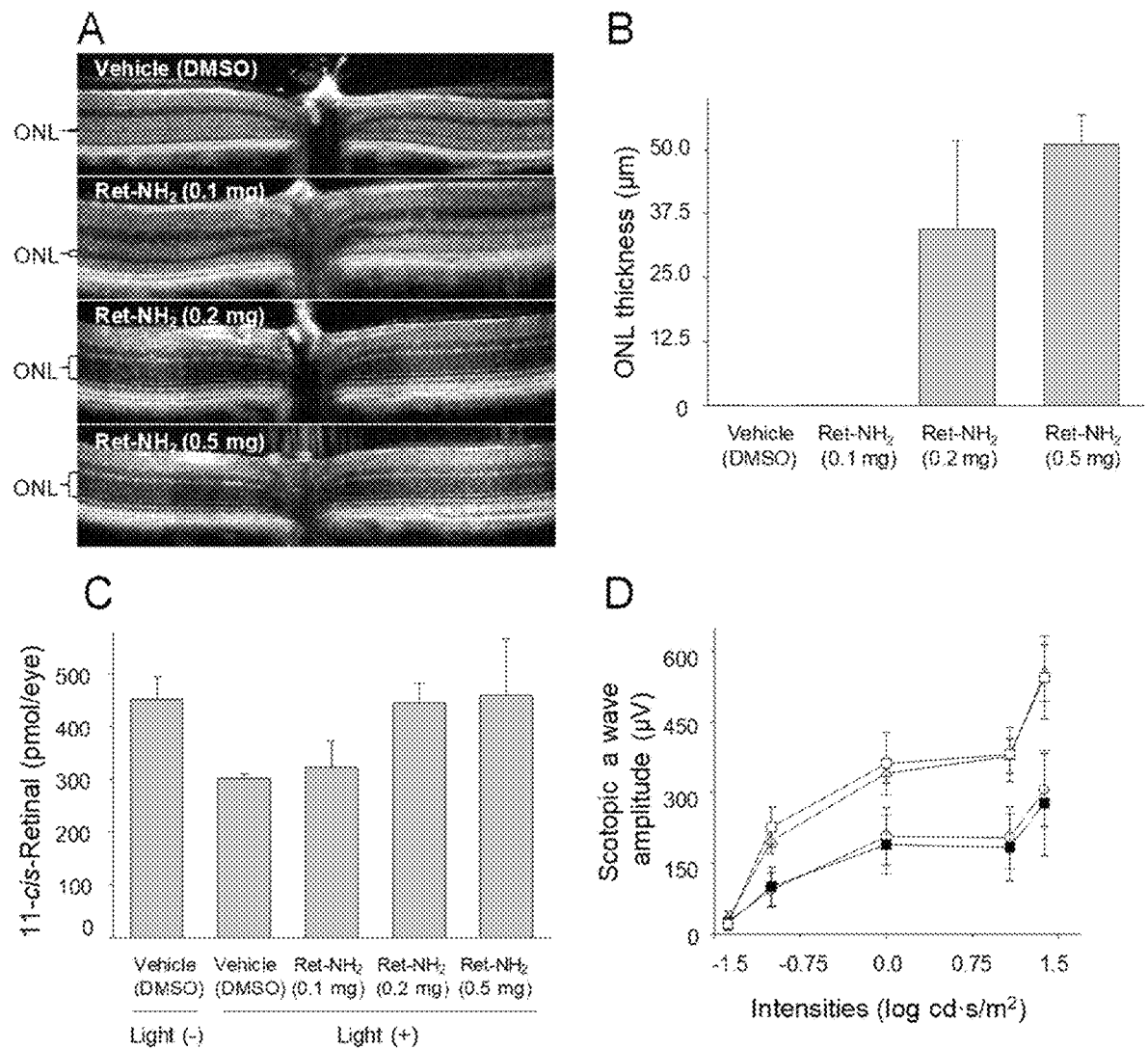
Figs. 6A-D

COMPOUNDS AND METHODS OF TREATING OCULAR DISORDERS

RELATED APPLICATION

This application claims priority from U.S. Provisional Application No. 62/083,704, filed Nov. 24, 2014, the subject matter, which is incorporated herein by reference.

GOVERNMENT FUNDING

This invention was made with government support under Grant No. EY09339 awarded by The National Institute of Health. The United States Government has certain rights in the invention.

TECHNICAL FIELD

This application relates to compounds and methods of treating ocular and/or retinal disorders that are associated with elevated levels of all-trans-retinal in the ocular tissue, and more particularly to compounds and methods of treating retinal degeneration and/or retinal disorders using primary amine compounds.

BACKGROUND

Highly expressed in rod and cone photoreceptor cells of the retina, visual pigments are G protein-coupled receptors (GPCRs) comprised of an opsin apo-protein combined with a universal chromophore, 11-cis-retinal through a protonated Schiff base. Upon absorption of a photon of light, the retinylidene chromophore is efficiently photoisomerized to an all-trans configuration with subsequent activation of the photoreceptor. Spontaneous hydrolysis of the Schiff base bond subsequently liberates all-trans-retinal from the opsin, but because visual pigments are densely packed at a local concentration up to 5 mM, an intense stream of photons can produce high levels of all-trans-retinal. At even low micromolar concentrations, this aldehyde is toxic, and primarily affects photoreceptor cells.

To restore photoreceptor sensitivity to light, a constant supply of 11-cis-retinal is required, and vertebrates employ a metabolic pathway called the retinoid (visual) cycle by which all trans retinal is enzymatically re-isomerized back to the 11-cis configuration. This process is facilitated by two non-redundant enzymes, namely lecithin:retinol acyltransferase (LRAT) and retinoid isomerase, a retinal pigmented epithelium-specific 65 kDa protein (RPE65) (FIG. 1). Retinylamine was the first described potent inhibitor of RPE65 discovered. But both enzymes employ retinylamine as a substrate. First retinylamine is retained in the eye by the action of LRAT that produces its amidated precursor, and then the resulting retinyl amide then is slowly hydrolyzed to evoke long-lasting suppression of retinoid isomerase activity.

An operative visual cycle is critical for sustaining continuous vision and maintaining the health of photoreceptor cells. Proper homeostasis of retinoid metabolism supports visual function under a variety of lighting conditions. However, certain environmental insults including prolonged exposure to intense light in combination with an unfavorable genetic background can exceed the adaptive capabilities of the visual cycle and thus compromise retinal function. A clinical example is Stargardt disease, an inherited form of juvenile macular degeneration that results in progressive vision loss associated with mutations in the photoreceptor-specific ATP binding cassette transporter (ABCA4) that causes a delay in all-trans-retinal clearance. The resulting increased concentrations of all-trans-retinal exert a direct cytotoxic effect on photoreceptors in addition to contributing to formation of side-products such as N-retinylidene-N-retinylethanolamine (A2E) and retinal dimer.

SUMMARY

This application relates to compounds and methods of treating an ocular disorder in a subject associated with increased or excessive all-trans-retinal levels in the ocular tissue of a subject. The ocular disorder can include, for example, retinal disorders, such as retinal degeneration, macular degeneration, including age-related macular degeneration, Stargardt disease, and retinitis pigmentosa. The method of treating the ocular disorder in a subject can include administering to the subject a therapeutically effective amount of a primary amine compound of formula:

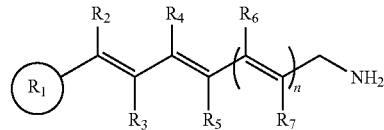

wherein $R_1$ is a cyclic or polycyclic ring, wherein the ring is a substituted or unsubstituted aryl, heteroaryl, cycloalkyl, or heterocyclyl;

n=1-3;

wherein $R_2$, $R_3$, $R_4$, $R_5$, $R_6$, and $R_7$, are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof, wherein, $R_2$ and $R_4$ may be linked to form a cyclic or polycyclic ring, wherein the ring is a substituted or unsubstituted aryl, heteroaryl, cycloalkyl, or heterocyclyl; and pharmaceutically acceptable salts thereof.

In an aspect of the application, the primary amine compound does not inhibit RPE65 enzymatic activity or any other proteins involved in retinoid metabolism in the eye of the subject. The primary amine compounds can reduce the formation of A2E and/or retinal dimer in the subject's retina and promote 11-cis-retinal production in the subject. The primary amine compound does not induce night blindness.

In another aspect of the application, the primary amine compound can be delivered to the subject by at least one of topical administration, systemic administration, intravitreal injection, and/or intraocular delivery. In one example, the primary amine can be provided in an ocular preparation for sustained delivery.

BRIEF DESCRIPTION OF THE DRAWINGS

FIGS. 2(A-D) are a Schematic representation of retinoid-based amines and their biological activities. (A) Retinoid-based amines. For QEA, R1 and R4 represent H or methyl, R2 and R3 are H or hydroxyl, R5 is H, methyl, t-butyl, benzyl or p-methoxy benzyl, R6 corresponds to H, methyl or t-butyl, and X could be O or N. For QEA-D and QEA-G-001, R5 represents a (CH2)3-bridge connecting C7 and C9. For TEA, R1 and R4 can be H or methyl, whereas R2 and R3 are H or hydroxyl, R5 is H or t-butyl, R6 can be H, methyl, t-butyl or benzyl, and R7 corresponds to H or methyl. For PEA, R1 and R2 are H or hydroxyl. (B) Schematic representation of the experimental design used to test the biological activity of amines. (C) Fraction of tested compounds that serve as substrates of LRAT. (D) Extent of inhibition displayed by tested amines against RPE65 enzymatic activity.

FIGS. 3(A-B) illustrate esterification QEA-B-001-NH2 and inhibition of RPE65. Primary amines were preincubated with bovine RPE microsomes at room temperature for 10 min; then all-trans-retinol was added and the mixture was incubated at 37° C. (A) HPLC chromatograph showing acylation of QEA-B-001-NH2 by LRAT in RPE microsomes (left panel); chromatograms 'a' and 'b' correspond to extracts of RPE microsomes in the absence and presence of QEA-B-001-NH2, respectively. Asterisks indicate a step change in the ethyl acetate mobile phase concentration (from 10% to 30% hexane). UV/Vis absorbance spectrum of a peak at 26 min of elution (right panel). This spectrum corresponds to QEA-B-001-NH2 amide (solid line). (B) Effect of inhibitor concentrations on the production of 11-cis-retinol (left panel). Inhibition of RPE65 enzymatic activity was measured as a decline in 11-cis-retinol production. (●)—QEA-B-001-NH2; (○)—retinylamine. All incubation mixtures were quenched by addition of methanol after 1 h of incubation at room temperature. 11-cis-Retinol production in the presence of (●)—5 NM QEA-B-001-NH2 (right panel); (▼)—30 μM QEA-B-001-NH2; (Δ)—5 μM Ret-NH2; (○)—30 μM retinylamine; (□)—control.

FIGS. 4(A-C) illustrate the protective effects of selected amines against light-induced retinal degeneration. Abca4$^{-/-}$ Rdh8$^{-/-}$ mice treated with tested amines were kept in the dark for 24 h and then bleached with 10,000 lux light for 1 h. (A) Representative OCT images of retinas from mice treated with 2 mg of different amines. Quantification of the protective effects of QEA-B-003-NH2, QEA-A-005-NH2, and retinylamine (Ret-NH2) are shown by measuring the averaged thickness of ONL. A dramatic decrease in ONL thickness indicates advanced retinal degeneration. Ret-NH2 and QEA-A-005-NH2 (2 mg) protected the ONLs of these mice. (B) Quantification of 11-cis-retinal in the eyes of mice kept in dark for 7 days after bleaching. The decreased amount of 11-cis-retinal in damaged eyes reflects the loss of photoreceptors. (C) HPLC chromatograph showing acylation of QEA-B-001-NH2 in mouse liver; 'a' is a representative chromatogram of a liver extract from mice treated with DMSO only, whereas 'b' corresponds to an extract from mice treated with QEA-B-001-NH2 (2 mg).

FIGS. 5(A-C) illustrate the inhibitory effect of retinylamine on the visual cycle in vivo. Inhibition of retinoid cycle was measured by recovery of 11-cis-retinal in eyes of WT mice after exposure to bright light. (A) Recovery of 11-cis-retinal in the eyes of mice when retinylamine was administered 2 h (A) or 24 h (B) prior to light exposure; (○)—control; (●)—0.2 mg retinylamine; (▼)—0.5 mg retinylamine; (Δ)—1.0 mg retinylamine; (▲)—0.5 mg retinylamine. Mice treated with vehicle only achieved above 80% of 11-cis-retinal recovery by 6 h after bleaching. (C) Temporal profile of the retinylamine effect on the retinoid cycle. Mice were gavaged with retinylamine 2 h to 7 days before light exposure. Amounts of 11-cis-retinal in the eye were measured 6 h after bleaching. Inhibition achieved a maximum at 24 h after bleaching and lasted more than 7 days. Symbols represent doses of retinylamine; (○)—0.1 mg, (●)—0.2 mg, and (Δ)—0.5 mg.

FIGS. 6(A-D) illustrate the protective effects of retinylamine against light-induced retinal degeneration. Mice gavaged with different doses of retinylamine were kept in the dark for 24 h and then bleached with 10,000 lux light for 1 h. (A) Representative OCT images of mouse retinas 3 days after bleaching. (B) Quantification of ONL thickness by OCT. (C) Recovery of 11-cis-retinal in retinas of mice kept in the dark for 7 days after bleaching. The decreased amounts of 11-cis-retinal in damaged eyes reflect the loss of photoreceptors. (D) Representative ERG responses of mice kept in the dark for 7 days after bleaching.

DETAILED DESCRIPTION

Figure 1:
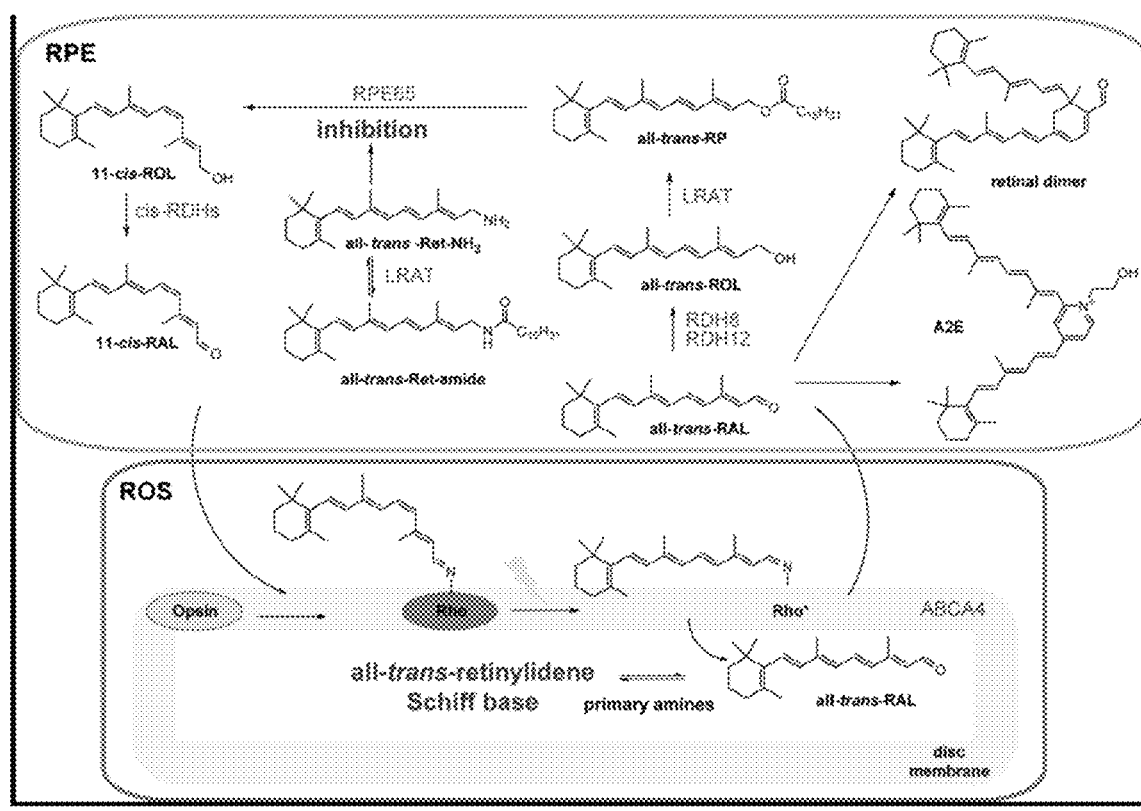
FIG. 1 is a schematic illustration of the retinoid (visual) cycle with therapeutic strategies against all-trans-retinal-mediated retinal degeneration. Photoisomerization of 11-cis-retinylidene bound to opsin results in release of all-trans-retinal from its protein opsin scaffold. All-trans-retinal is flipped by ABCA4, to the cytoplasmic leaflet of the disc lipid membrane and then reduced to all-trans-retinol by RDH8 and RDH11 in the RPE. Insufficient activity of these enzymes results in over-accumulation of all trans-retinal and subsequent formation of precursors of A2E and retinal dimer. Importantly, all trans-retinal itself is cytotoxic to photoreceptors. Formation of a transient Schiff base with primary amines can sequester the excess of this toxic aldehyde. Alternatively, cytoprotection can be achieved by inhibiting the visual cycle to slow down the supply of all-trans-retinal.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" refers to compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are nonsuperimposable mirror images are termed "enantiomers", or sometimes optical isomers. A carbon atom bonded to four nonidentical substituents is termed a "chiral center".

The term "chiral isomer" refers to a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2n-1$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric isomers" refer to the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative", refers to compounds that have a common core structure, and are substituted with various groups as described herein. For example, all of the compounds represented by formula I are primary amines and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" refer to modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" refers to inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" refers to stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term a "pharmaceutical composition" refers to a formulation containing the disclosed compounds in a form suitable for administration to a subject. The pharmaceutical composition can be in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including ocular, oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" refers to a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" refers to pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated within the scope of the claims.

The phrase "pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present application is intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds described herein wherein a hydroxy, amino, sulfhydryl, carboxy, or carbonyl group is bonded to any group that may be cleaved in vivo to form a free hydroxyl, free amino, free sulftydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds described herein, and the like (e.g., Bundegaard, H. "Design of Prodrugs" p1-92, Elesevier, New York-Oxford (1985)).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2$^{nd}$ ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" refers to a functional group that converts an amine, amide, or other nitrogen-containing moiety into a different chemical group that is substantially inert to the conditions of a particular chemical reaction. Amine protecting groups can be removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other amine protecting groups can be identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" refers to solvent addition forms that contain either stoichiometric or non stoichiometric amounts of solvent. Some compounds have a tendency to trap a fixed molar ratio of solvent molecules in the crystalline solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g. an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as primates, mammals, and vertebrates.

The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" refer to molecules and other agents that are biologically, physiologically, or pharmacologically active substances that act locally or systemically in a patient or subject to treat a disease or condition, such as retinal degeneration or other forms of retinal disease whose etiology involves elevated levels of all trans-retinal in the ocular tissue of a subject. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" refer to the dose of a drug, which produces 50% of its maximum response or effect, or alternatively, the dose, which produces a pre-determined response in 50% of test subjects or preparations. The term "LD50" refers to the dose of a drug, which is lethal in 50% of test subjects. The term "therapeutic index" refers to the therapeutic index of a drug, defined as LD50/ED50.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" refers to a molecule, which has a molecular weight of less than about 2000 amu, or less than about 1000 amu, and even less than about 500 amu.

All percentages and ratios used herein, unless otherwise indicated, are by weight.

The term "retina" refers to a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The term "macula" refers to the central region of the retina, which contains the fovea where visual images are processed by long slender cones in high spatial detail ("visual acuity"). "Macular degeneration" is a form of retinal neurodegeneration, which attacks the macula and destroys high acuity vision in the center of the visual field. AMD can be in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipfuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

The term "ERG" is an acronym for electroretinogram, which is the measurement of the electric field potential emitted by retinal neurons during their response to an experimentally defined light stimulus. ERG is a non-invasive measurement, which can be performed on either living subjects (human or animal) or a hemisected eye in solution that has been removed surgically from a living animal.

The present invention relates to primary amine containing compounds for use in the treatment of diseases and disorders related to excess or increased all-trans-retinal in a subject's ocular tissue. It has been discovered that all-trans-retinal, a retinoid metabolite naturally produced during visual processing, is highly toxic when present at elevated levels. To lower its toxicity, therapeutic primary amines have been identified in the Examples below that can be delivered to and retained in the eye when amidated with fatty acids by lecithin:retinol acyl transferase (LRAT).

In some embodiments, the ocular disorder associated with increased or excessive all-trans-retinal in the ocular tissue of a subject can include, for example, retinal degeneration, macular degeneration, including age-related macular degeneration including the dry form and the wet form of age related macular degeneration, Stargardt's disease, Stargardt macular degeneration, fundus flavimaculatus, geographic atrophy, retinitis pigmentosa, ABCA4 mutation related retinal dystrophies, vitelliform (or Best) macular degeneration, adult onset form of vitelliform macular dystrophy, Sorsby's fundus dystrophy, Malattia leventinese (Doyne honeycomb or dominant radial drusen), diabetic retinopathy, diabetic maculopathy, diabetic macular edema, retinopathy that is or presents geographic atrophy and/or photoreceptor degeneration, retinopathy that is a lipofuscin-based retinal degeneration, aberrant modulation of lecithin-retinol acyltransferase in an eye, Leber's congenital amaurosis, retinal detachment, hemorrhagic retinopathy, hypertensive retinopathy, hereditary or non hereditary optic neuropathy, inflammatory retinal disease, retinal blood vessel occlusion, retinopathy of prematurity, ischemia reperfusion related retinal injury, proliferative vitreoretinopathy, retinal dystrophy, uveitis, retinal disorders associated with Alzheimer's disease, retinal disorders associated with multiple sclerosis, retinal disorders associated with Parkinson's disease, retinal disorders associated with viral infection (cytomegalovirus or herpes simplex virus), retinal disorders related to light overexposure or myopia, retinal disorders associated with AIDS, glaucoma, genetic retinal dystrophies, traumatic injuries to the optic nerve, such as by physical injury, excessive light exposure, or laser light, neuropathies due to a toxic agent or caused by adverse drug reactions or vitamin deficiency, progressive retinal atrophy or degeneration, retinal diseases or disorders resulting from mechanical injury, chemical or drug-induced injury, thermal injury, radiation injury, light injury, or laser injury, hereditary and non-hereditary retinal dystrophy, ophthalmic injuries from environmental factors, such as light-induced oxidative retinal damage, laser-induced retinal damage, "flash bomb injury," or "light dazzle", refractive errors including but not limited to myopia, and retinal diseases related to A2E accumulation including RDS/PHRP2-related macular degeneration, Batten disease (juvenile neuronal ceroid lipofuscinosis), and central serous chorioretinopathy.

Present at high micromolar levels, all-trans-retinal is uniquely concentrated in the eye and constitutes an ideal target for primary amine-containing drugs that do not interact with cellular machinery and processes. In certain embodiments, the primary amine containing compounds described herein do not inhibit enzymes, channels or receptors but instead react with all-trans-retinal. When administered to a subject, the primary amine containing compounds described herein transiently sequester all-trans-retinal in ocular tissue by forming a Schiff base and thus reduce peak concentrations of the toxic aldehyde. Because this reaction is readily reversible, there is no discernable diminution in the total amount of all-trans retinal needed for replenishment of the visual chromophore, 11-cis-retinal. In certain embodiments, the stability of the Schiff-bases formed from the primary amine compounds should be such that the level of free all-trans-retinal in the ocular tissue of a subject is reduced to a level that is effective to mitigate retinal degeneration but not impair the normal retinoid cycle.

In some embodiments, the primary amine compounds in accordance with the application do not inhibit RPE65 and/or LRAT enzymatic activity or any other proteins involved in retinoid metabolism in the eye of the subject. Inhibition of retinoid isomerase (RPE65) can produce the highly undesirable side effect of severely delayed dark adaptation. Therefore, in certain embodiments, the primary amine compounds for use in a method described herein do not inhibit RPE65 and subsequently do not cause delayed dark adaptation (i.e., night blindness) in a subject.

In an embodiment of the application, the primary amine compounds that can inhibit retinal degeneration upon administration to a subject can be selected using an in vitro assays that measure the ability of a primary amine compound to act as a substrate for LRAT and sequester excessive all-trans-retinal in the ocular tissue and in vivo assays that measure, the optical coherence tomography score of retinas of Rdh8$^{-/-}$Abca4$^{-/-}$ mice exposed to intense light-induced retinal degeneration. In certain embodiments, the primary amine compounds that can inhibit retinal degeneration upon administration to a subject do not significantly inhibit RPE65 activity in a subject's ocular tissue. In some embodiments, primary amine compounds when administered to a Rdh8$^{-/-}$Abca4$^{-/-}$ mouse increase the optical coherence tomography score of the mouse in comparison to untreated control animal are effective in treating ocular diseases and disorders in a subject associated with increased or excessive all-trans-retinal levels in ocular tissue. Additionally, in some embodiments, therapeutic efficacy of the primary amine compounds of the application can be determined using an in vitro assay that measures the ability of a primary amine compound to improve viability of RPE cells treated with retinal.

In some embodiments, the primary amine compound for use in a method described herein can include the structural formula (I):

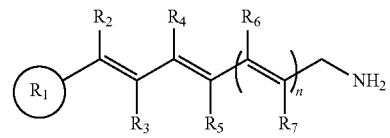

wherein $R_1$ is a cyclic or polycyclic ring, wherein the ring is a substituted or unsubstituted aryl, heteroaryl, cycloalkyl, or heterocyclyl;
wherein n=1-3;
wherein $R_2$, $R_3$, $R_4$, $R_5$, $R_6$, and $R_7$, are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof; and
wherein, $R_2$ and $R_4$ may be linked to form a cyclic or polycyclic ring, wherein the ring is a substituted or unsubstituted aryl, heteroaryl, cycloalkyl, or heterocyclyl; and pharmaceutically acceptable salts thereof.

In some embodiments, the primary amine compound for use in a method described herein can include the structural formula (II):

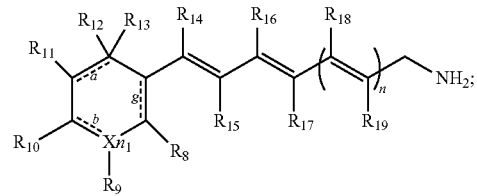

wherein a, b and g indicate optional double bonds;
wherein X═C, O or N, n=1-3, $n_1$=0 or 1;
wherein when $n_1$ is 0, the ring becomes a five member substituted or unsubstituted ring structure;

wherein $R_8$, $R_9$, $R_{10}$, $R_{11}$, $R_{12}$, $R_{13}$, $R_{14}$, $R_{15}$, $R_{16}$, $R_{17}$, $R_{18}$, and $R_{19}$ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

wherein, $R_{10}$ and $R_{11}$, $R_{13}$ and $R_{14}$ or $R_8$ and $R_{15}$ may be linked to form a cyclic or polycyclic ring, wherein the ring is a substituted or unsubstituted aryl, heteroaryl, cycloalkyl, or heterocyclyl; and pharmaceutically acceptable salts thereof.

In some embodiments, the primary amine compound for use in a method described herein can include the structural formula (III):

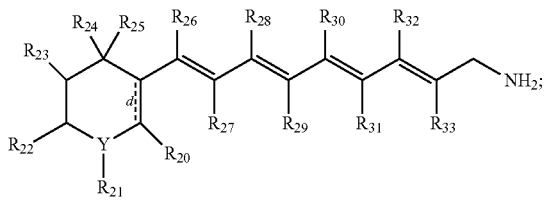

wherein d indicates an optional double bond;
wherein Y=C or O;
wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, and $R_{33}$, are each individually hydrogen, CH3, OH, t-butyl, benzene, arisole (methoxybenzene) or combinations thereof;
wherein $R_{26}$ and $R_{28}$ may be linked to form a cycloalkene ring; and pharmaceutically acceptable salts thereof.

In some embodiments, the primary amine compound for use in a method described herein can include the structural formula (IV):

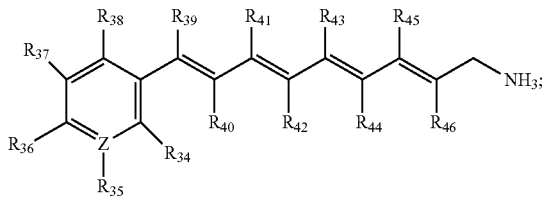

wherein Z=C or N;
wherein $R_{34}$, $R_{35}$, $R_{36}$, $R_{37}$, $R_{38}$, $R_{39}$, $R_{40}$, $R_{41}$, $R_{42}$, $R_{43}$, $R_{44}$, $R_{45}$, and $R_{46}$ are each individually hydrogen, trifluoromethyl (—CF$_3$), Cl, nitro (—NO$_2$), CH$_3$, OH, t-butyl, benzene, arisole (methoxybenzene) or combinations thereof;

wherein $R_{36}$ and $R_{37}$ may be linked to form a cyclohexane ring and $R_{39}$ and $R_{41}$ may be linked to form a cycloalkene ring; and pharmaceutically acceptable salts thereof.

In some embodiments, the primary amine compound for use in a method described herein can include the structural formula (V):

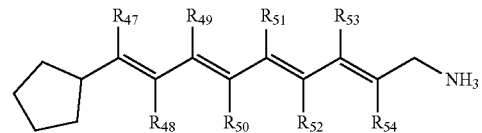

wherein $R_{47}$, $R_{48}$, $R_{49}$, $R_{50}$, $R_{51}$, $R_{52}$, $R_{53}$, and $R_{54}$ are each individually hydrogen, —CH$_3$ or combinations thereof; and pharmaceutically acceptable salts thereof.

In some embodiments, the primary amine compound for use in a method described herein can include the structural formula (VI):

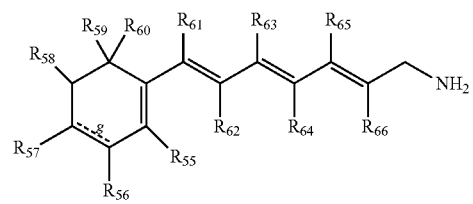

wherein g indicates an optional double bond;
wherein $R_{55}$, $R_{56}$, $R_{57}$, $R_{58}$, $R_{59}$, $R_{60}$, $R_{61}$, $R_{62}$, $R_{63}$, $R_{64}$, $R_{65}$, and $R_{66}$ are each individually hydrogen, CH$_3$, OH, t-butyl, benzene, or combinations thereof; and pharmaceutically acceptable salts thereof.

In some embodiments, the primary amine compound for use in a method described herein can include the structural formula (VII):

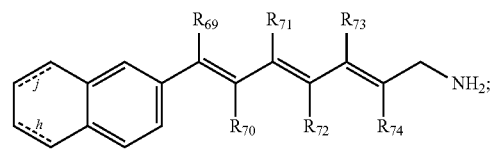

wherein j and h indicate an optional double bond;
wherein $R_{69}$, $R_{70}$, $R_{71}$, $R_{72}$, $R_{73}$, and $R_{74}$ are each individually hydrogen, CH$_3$, t-butyl, benzene, or combinations thereof; and pharmaceutically acceptable salts thereof.

In some embodiments, the primary amine compound for use in a method described herein can include the structural formula (VIII):

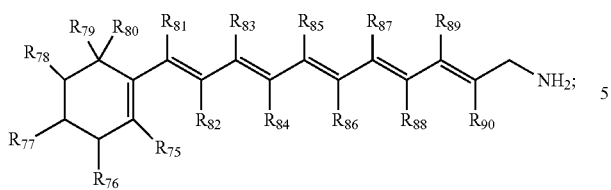

wherein $R_{75}$, $R_{76}$, $R_{77}$, $R_{78}$, $R_{79}$, $R_{80}$, $R_{81}$, $R_{82}$, $R_{83}$, $R_{84}$, $R_{85}$, $R_{86}$, $R_{87}$, $R_{88}$, $R_{89}$ and $R_{90}$ are each individually hydrogen, $CH_3$, OH, or combinations thereof; and pharmaceutically acceptable salts thereof.

In an embodiment of the application, the primary amine compounds can include primary amine compounds having the following structural formulas:

QEA-A-002-NH2

QEA-A-003-NH2

QEA-A-004-NH2

QEA-A-005-NH2

QEA-A-006-NH2

QEA-B-001-NH2

QEA-B-002-NH2

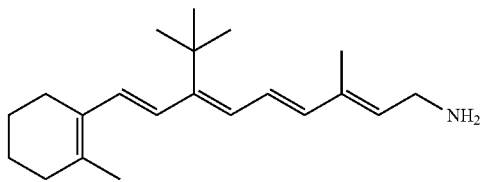

QEA-B-003-NH2

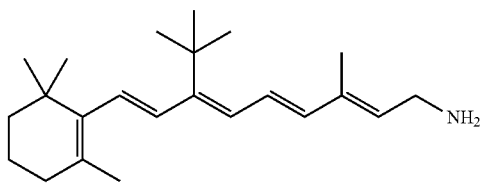

QEA-B-004-NH2

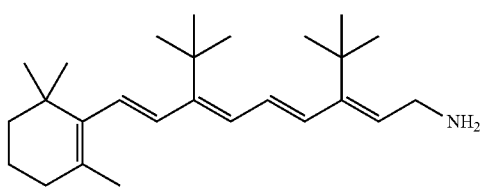

QEA-B-005-NH2

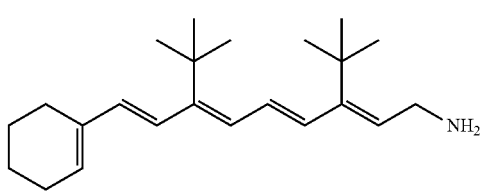

QEA-C-001-NH2

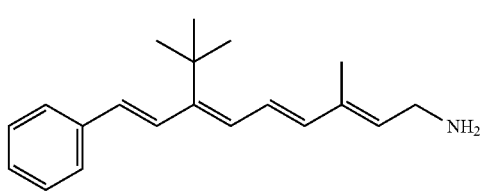

QEA-C-002-NH2

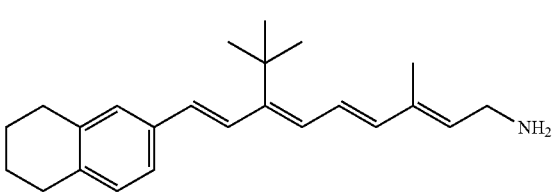

QEA-C-003-NH2

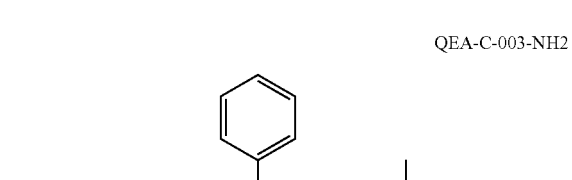

-continued
QEA-C-004-NH2
QEA-C-005-NH2
QEA-C-006-NH2
QEA-D-001-NH2
QEA-D-002-NH2
QEA-E-001-NH2
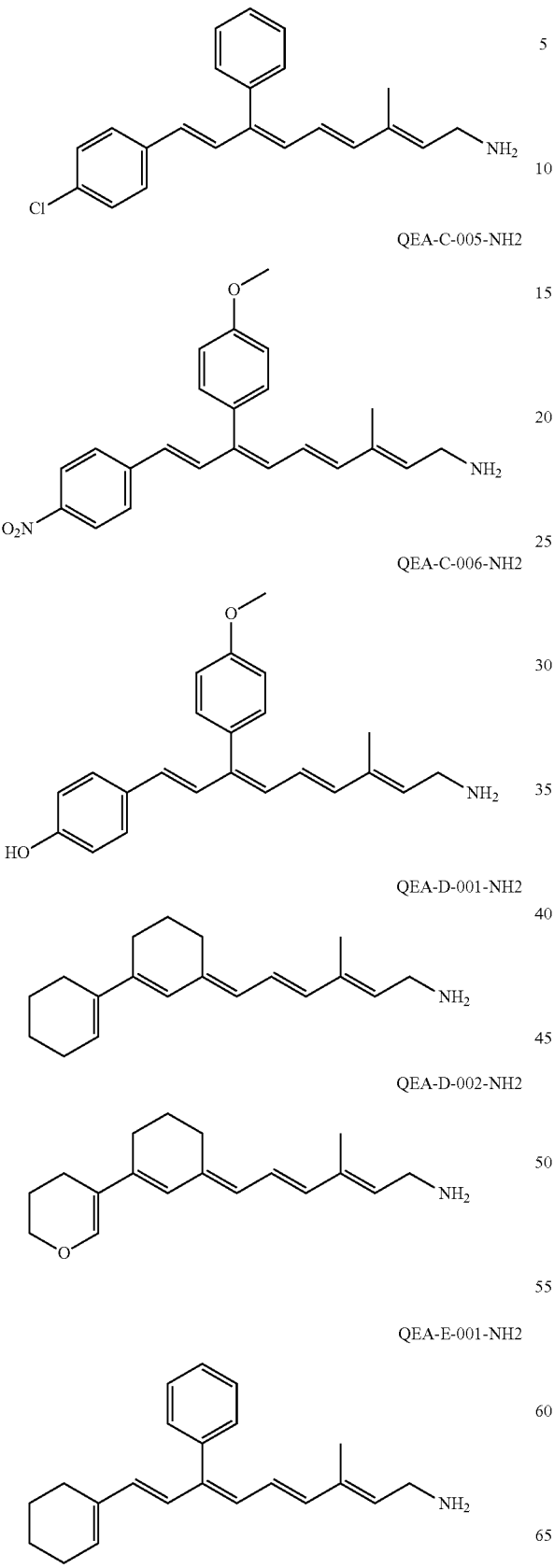
-continued
QEA-E-002-NH2
QEA-F-001-NH2
QEA-F-002-NH2
QEA-G-001-NH2
QEA-G-002-NH2
TEA-A-001-NH2
TEA-A-002-NH2
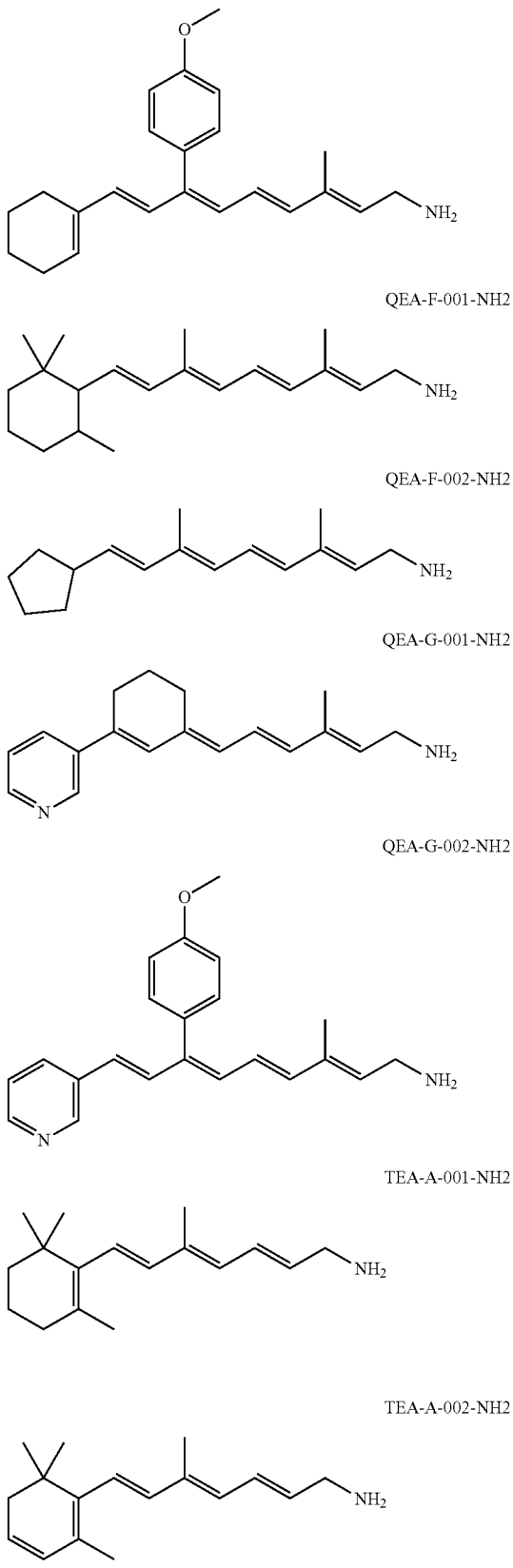

TEA-A-003-NH2
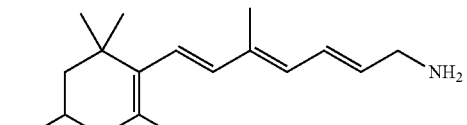

TEA-A-004-NH2
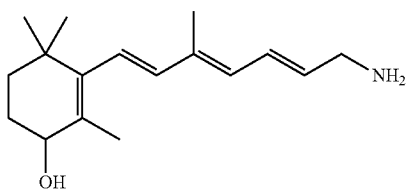

TEA-B-001-NH2
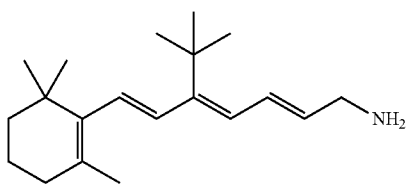

TEA-B-002-NH2
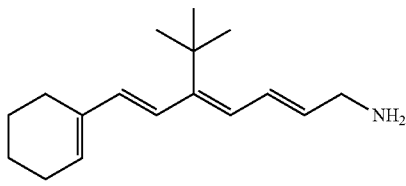

TEA-B-003-NH2
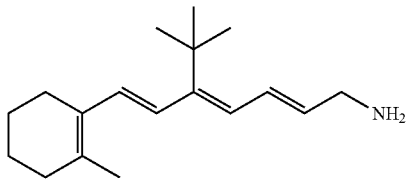

TEA-B-004-NH2
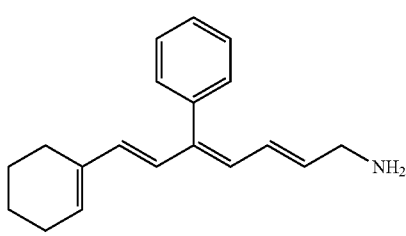

TEA-C-001-NH2
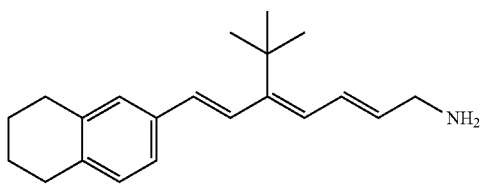

TEA-C-002-NH2
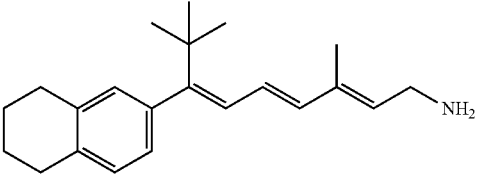

PEA-A-001-NH2
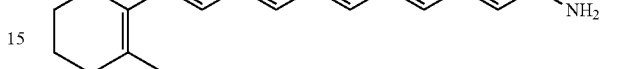

PEA-A-002-NH2
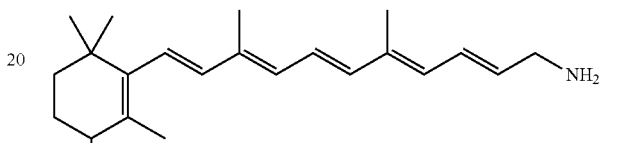

PEA-A-003-NH2
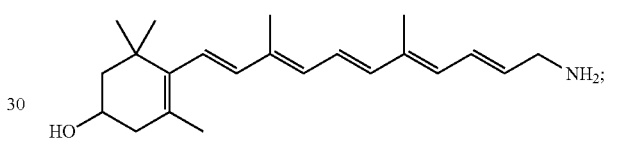

and pharmaceutically acceptable salts thereof.

The primary amine compounds used in methods described herein can be administered to the subject to treat the ocular disorder (e.g., macular degeneration or Stargardt disease) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In another embodiment, the primary amine compound can be administered after induction of macular degeneration has occurred.

The treatment methods can include administering to the subject a therapeutically effective amount of the primary amine compound. Determination of a therapeutically effective amount is within the capability of those skilled in the art. The exact formulation, route of administration, and dosage can be chosen by the individual physician in view of the subject's condition.

Formulation of pharmaceutical compounds for use in the modes of administration noted above (and others) are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y. U.S.A., 1999.

In one example, the primary amine compound can be provided in an ophthalmic preparation that can be administered to the subject's eye. The ophthalmic preparation can contain the primary amine compound in a pharmaceutically acceptable solution, suspension or ointment. Some variations in concentration will necessarily occur, depending on the particular primary amine compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Examples of preservatives for use in such a solution include benzalkonium chloride, benzethonium chloride, chlorobutanol, thimerosal and the like. Examples of buffers include boric acid, sodium and potassium bicarbonate, sodium and potassium borates, sodium and potassium carbonate, sodium acetate, and sodium biphosphate, in amounts sufficient to maintain the pH at between about pH 6 and about pH 8, and for example, between about pH 7 and about pH 7.5. Examples of tonicity agents are dextran 40, dextran 70, dextrose, glycerin, potassium chloride, propylene glycol, and sodium chloride.

Examples of antioxidants and stabilizers include sodium bisulfite, sodium metabisulfite, sodium thiosulfite, and thiourea. Examples of wetting and clarifying agents include polysorbate 80, polysorbate 20, poloxamer 282 and tyloxapol. Examples of viscosity-increasing agents include gelatin, glycerin, hydroxyethylcellulose, hydroxmethylpropylcellulose, lanolin, methylcellulose, petrolatum, polyethylene glycol, polyvinyl alcohol, polyvinylpyrrolidone, and carboxymethylcellulose. The ophthalmic preparation will be administered topically to the eye of the subject in need of treatment by conventional methods, for example, in the form of drops or by bathing the eye in the ophthalmic solution.

The primary amine compound can also be formulated for topical administration through the skin. "Topical delivery systems" also include transdermal patches containing the ingredient to be administered. Delivery through the skin can further be achieved by iontophoresis or electrotransport, if desired.

Formulations for topical administration to the skin can include, for example, ointments, creams, gels and pastes comprising the primary amine compound in a pharmaceutical acceptable carrier. The formulation of the primary amine compound for topical use includes the preparation of oleaginous or water-soluble ointment bases, as is well known to those in the art. For example, these formulations may include vegetable oils, animal fats, and, for example, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Subjects affected with or at risk of macular degeneration, which are not readily accessible or suitable for ophthalmic (e.g. eye-drops) and/or topical administration, can be treated by a systemic approach, such as intravenous infusion. For example, the primary amine compound can be administered at a low dosage by continuous intravenous infusion. In another example, in which a patient requires longer-term care, the primary amine compound can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the primary amine compound to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the primary amine compound.

As discussed above, the primary amine compounds may be administered to a subject in order to treat or prevent macular degeneration and other forms of retinal disease whose etiology involves elevated levels of toxic all-trans-retinal in a subject. Other diseases, disorders, or conditions characterized by increased or excessive all-trans-retinal in ocular tissue may be similarly treated.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves increased all-trans-retinal in ocular tissue of a subject, and then the compound is administered. In another embodiment, a subject may be identified as being at risk for developing other forms of retinal disease whose etiology involves increased all-trans-retinal in ocular tissue, and then the disclosed compound is administered. In some embodiments, a compound is administered prophylactically. In some embodiments, a subject has been diagnosed as having the disease before retinal damage is apparent. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves increased all-trans-retinal in ocular tissue, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD, which is treated with, e.g., photodynamic therapy.

In yet another embodiment, the primary amine compound described herein can be administered as part of a combinatorial therapy with additional therapeutic agents. The phrase "combinatorial therapy" or "combination therapy" embraces the administration of a primary amine compound, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

The invention is further illustrated by the following example, which is not intended to limit the scope of the claims.

Example

Two enzymes are critical for retinoid recycling in the eye. Lecithin:retinol acyl transferase (LRAT) is the enzyme that initially traps retinol from circulation and photoreceptor cells to produce the esterified substrate for the second enzyme, retinoid isomerase (RPE65) which converts the retinoid ester to an alcohol. Thus protective compounds and substrates of LRAT could be selectively delivered to the eye. However, the similarity of LRAT's substrate/product profile with that of RPE65 could inhibit the isomerase and produce delayed dark adaptation, a debilitating visual problem for humans. Here we delineated certain chemical boundaries for LRAT substrate and RPE65 inhibitor specificities together with their protection against retinal degeneration in mice.

We investigated retinylamine and many of its derivatives to assess their substrate/inhibitor binding specificities for RPE65 and LRAT, the mechanism(s) of their action, potency, retention in the eye and protection against acute light-induced retinal degeneration in mice. Such information could be critical for understanding the modes of action for current and future visual cycle modulators.

Methods

Chemicals and Synthesis

Unless otherwise stated, solvents and reagents were purchased from Sigma (St. Louis, Mo.). QEA-A-002 and QEA-A-003 were obtained from Toronto Research Chemicals Inc. (Toronto, Canada). Other aldehydes were synthesized as described in Supporting Information. Syntheses of primary alcohols and amines were performed by previously described procedures. $^1$H NMR spectra (300, 400 or 600 MHz) and $^{13}$C NMR spectra (100 or 150 MHz) were recorded with Varian Gemini and Varian Inova instruments.

Because retinal is much more stable than retinylamine or retinol, all novel retinoid derivatives were synthesized and stored in their aldehyde forms and were converted to primary alcohols/amines just prior to drug screening. The general scheme of synthesis began with building the β-ionone ring analogs, and was followed by elongating the polyene chain with an aldol condensation, a Wittig-Horner reaction or Suzuki coupling. Synthesized retinal analogs were categorized as QEA, TEA, and PEA based on their polyene chain length (FIG. 2A). Among 35 synthesized aldehydes, four—QEA-E-001, QEA-E-002, QEA-F-001, and QEA-F-002 were unstable and decomposed before proper NMR spectra were completed. Structures and purities of all other compounds were confirmed by H and $^{13}$C NMR as well as by mass spectrometry.

RPE Microsomal Preparations

Bovine RPE microsomes were isolated from RPE homogenates by differential centrifugation as previously described. The resulting microsomal precipitate was resuspended in 10 mM Bis-Tris propane/HCl buffer, pH 7.4, to achieve a total protein concentration of ~5 mg. ml$^{-1}$. Then the mixture was placed in a quartz cuvette and irradiated for 6 min at 4° C. with a ChromatoUVE transilluminator (model TM-15; UVP) to eliminate residual retinoids. After irradiation, DTT was added to the RPE microsomal mixture to achieve a final concentration of 5 mM.

LRAT Activity Assays

Two μl of a synthesized primary alcohol or amine dissolved in DMF (final concentration 10 μM) and 2 μl of 1,2-diheptanoyl-sn-glicerol-3-phosphocholine (water, final concentration 1 mM) were added to 200 μl of 10 mM Bis-Tris propane/HCl buffer, pH 7.4, containing 150 μg of RPE microsomes and 1% (v/w) BSA. The resulting mixture was incubated at 37° C. for 1 h. The reaction was quenched by adding 300 μl of methanol. Most reaction products were extracted with 300 μl of hexanes, except for products from the QEA-C-006 and QEA-G groups which were extracted by adding 300 μl of ethyl acetate and 300 μl of water.

Reaction products were separated and quantified by normal phase HPLC (Agilent Sil 5 μm, 4.6 mm×250 mm) in stepwise gradient of ethyl acetate in hexanes (0-15 min, 10%; 20-30 min, 30%) at a flow rate of 1.4 ml·min$^{-1}$. Because for each tested compound, both the substrate and product showed almost same UV absorption maximum, quantification was based on equivalent UV absorption by the substrate and product at this specific wavelength.

Retinoid Isomerase Activity Assays

Two μl of the synthesized primary amine (in DMF, final concentration ranging between 0.1 and 10 μM) was added to 10 mM Bis-Tris propane/HCl buffer, pH 7.4, containing 150 μg of RPE microsomes, 1% BSA, 1 mM disodium pyrophosphate and 20 μM aporetinaldehyde-binding protein 1 (CRALBP). The resulting mixture was pre incubated at room temperature for 5 min. Then 1 μl of all-trans-retinol (in DMF, final concentration 20 μM) was added. The resulting mixture was incubated at 37° C. for 15 min to 2 h. The reaction was quenched by adding 300 μl of methanol, and products were extracted with 300 μl of hexanes. Production of 11-cis-retinol was quantified by normal phase HPLC with 10% (v/v) ethyl acetate in hexanes as the eluent at a flow rate of 1.4 ml·min$^{-1}$. Retinoids were detected by monitoring their absorbance at 325 nm and quantified based on a standard curve representing the relationship between the amount of 11-cis-retinol and the area under the corresponding chromatographic peak.

Mouse Handling and Drug Administration

Abca4$^{-/-}$Rdh8$^{-/-}$ double knockout mice were generated as previously described. Mice were housed in the animal facility at the School of Medicine, Case Western Reserve University, where they were maintained under either complete darkness or in a 12-h light (~300 lux) and 12-h dark cycle. All tested primary amines were suspended in 100 μl of soybean oil with less than 10% (v/v) DMSO and were administered by oral gavage with a 22-gauge feeding needle. Experimental manipulations in the dark were done under dim red light transmitted through a Kodak No. 1 safelight filter (transmittance >560 nm). All animal procedures and experiments were approved by the Case Western Reserve University Animal Care Committees and conformed to recommendations of the American Veterinary Medical Association Panel on Euthanasia and the Association of Research for Vision and Ophthalmology.

Induction of Acute Retinal Degeneration in Abca4$^{-/-}$Rdh8$^{-/-}$ Mice

After dark adaptation for 24 h, 4-week-old male or female Abca4$^{-/-}$Rdh8$^{-/-}$ mice with pupils dilated by 1% tropicamide were exposed to fluorescent light (10,000 lx; 150 W spiral lamp, Commercial Electric) for 1 h in a white paper bucket (Papersmith), and then kept in the dark for an additional 3 d. Development of retinal degeneration was then examined by ultra-high resolution spectral-domain OCT (SDOCT; Bioptigen) and ERGs as previously described.

Analysis of Retinoid Composition in Mouse Tissues

Two mg of primary amines were administered by oral gavage to 4-week-old Abca4$^{-/-}$ Rdh8$^{-/-}$ mice, which then were kept in the dark for 24 h. Then mice were euthanized, and their livers were homogenized in 1 ml of 10 mM sodium phosphate buffer, pH 7.4, containing 50% methanol (v/v). The resulting mixture was extracted with 4 ml of hexanes. Extracts were dried in vacuo, and reconstituted in 300 μl of hexanes. 100 μl of this solution was analyzed by HPLC as described above for the LRAT activity assay.

Visual Chromophore Recovery Assay

After bright light exposure that resulted in photoactivation of 90% of rhodopsin, mice were kept in darkness for 2 h to 7 d. Then animals were euthanized and their eyes were collected and homogenized in 10 mM sodium phosphate buffer, pH 7.4, containing 50% methanol (v/v) and 40 mM hydroxylamine. The resulting mixture was extracted with 4 ml of hexanes. Extracts were dried in vacuo, reconstituted in 300 μl of hexanes and 100 μl of the extract was injected into an HPLC for analysis with 10% (v/v) ethyl acetate in hexanes.

Statistical Analyses

Data representing the means±s.d. for the results of at least three independent experiments were compared by the one-way analysis of variance Student's t test. Differences with P values <0.05 were considered as statistically significant.

Results

Design and Synthesis of Novel Retinal Analogs

To find primary amines that have potential to serve as substrates of LRAT without imposing a strong inhibitory effect on retinoid isomerization, we designed and synthesized a series of retinoid analogs (FIG. 2A). Prior to this study, the only known primary amine acting as a substrate for LRAT was retinylamine.

Thus retinylamine was chosen as a starting moiety for further chemical modifications. Although LRAT was shown to have a broad substrate specificity, chemical boundaries that determine the substrate selectivity for this enzyme have not yet been clarified.

In contrast, the crystal structure of RPE65 has been elucidated in detail revealing a narrow tunnel that leads into the active site of this enzyme. Indeed, a relatively small structural modification of the retinoid moiety could effectively abolish binding of an inhibitor to this enzyme. Thus, we hypothesized that subset of primary amines and LRAT substrates would not inhibit RPE65 enzymatic activity.

In Vitro Screening for Lead Compounds

The properties of retinoid derivatives were examined by two standard enzymatic tests, the LRAT and retinoid isomerization assays. To identify substrates of LRAT, aldehydes were reduced by sodium borohydrate to their corresponding primary alcohols that then were directly used in the esterification assay (FIG. 2B).

The alcohols were incubated with RPE microsomes that served as a source of LRAT enzymatic activity. Products of the enzymatic reaction as well as the remaining substrates were extracted with organic solvents and analyzed by HPLC. The ratio between a substrate and its esterified form was used to measure enzymatic activity efficiency, based on equivalent UV absorption of the substrate and product at their specific UV maxim wavelengths. Compounds classified as 'good' LRAT substrates converted at least 50% of their available alcohol substrates into corresponding esters under these experimental conditions, whereas marginal LRAT substrates were converted at less than 5%. Alcohols with a 5-50% conversion ratio were classified as weak substrates. An example is shown in FIG. 3A for QEB-B-001. Among 35 tested compounds, 23 were categorized as good and 9 as weak substrates; 3 compounds were not esterified by LRAT (Table 1 and FIG. 2C). Based on these data, we conclude that a six carbon ring is a critical structural feature for LRAT's substrate recognition (Table 1). Importantly, various modifications within the β-ionone ring, including incorporation of heteroatoms, deletion of methyl groups or addition of functional groups did not significantly alter ester formation. Moreover, breaking double bond conjugation along the polyene chain or deletion of a C9 and/or a C13 methyl group also was allowed. In contrast, exchange of the C13 methyl with a bulky tertbutyl group strongly inhibited substrate binding. Interestingly, the C9 methyl could be replaced with a variety of substituents including a tertbutyl, benzene and its derivatives or even an alkyl chain bridging to C7 which resulted in a rigid configuration of the polyene chain. Reduced enzymatic activity was observed with ionylidene analogues of fewer than 12 carbons in length.

Primary amines of compounds derived from the aldehydes were subsequently tested for their ability to inhibit the RPE65-dependent retinoid isomerization reaction in dose- and time dependent reactions as exemplified by QEB-B-001 (FIG. 3B). Amines were incubated with RPE microsomes in the presence of all-trans-retinol and the 11-cis-retinoid binding protein, CRALBP.

Progress of the enzymatic reaction was monitored by HPLC separation of retinoids and quantification of 11-cis-retinol with a decrease of 11-cis-retinol production reflecting inhibition of RPE65 by a tested amine. Compounds with an $IC_{50}$ below 10 μM were defined as strong inhibitors, those with an IC50 between 10-100 μM were categorized as moderate inhibitors, and compounds with an IC50 above 100 μM were viewed as non-inhibitors (Table 1). Among the 32 amines which served as substrates of LRAT, 11 exhibited strong inhibition of RPE65; 4 showed moderate inhibition and 17 did not affect the isomerization reaction. Those amines exhibiting no inhibition had two common features: an altered β-ionone ring structure characterized by the absence of methyl groups and the presence of one bulky group like a t-butyl or benzyl group at the C9 position. For example, QEA-B-001-NH2 was a good LRAT substrate but a modest or non-inhibitor of RPE65 (FIG. 3). Compounds containing only one of these modifications (QEA-A-006-NH2 and QEA-B-003-NH2) showed moderate inhibition of RPE65 implying a synergistic effect of both changes in completely undermining the RPE65 inhibitory effect (Table 1). This moderate inhibition could be enhanced by shortening the polyene chain length (TEA amines) or diminished by introducing an extra positive charge into the tested compounds (QEA-G amines).

TABLE 1

Summary of primary amines as substrates for LRAT and RPE65 in vitro

| Compound | Structure | LRAT Substrate[a] | Inhibition of RPE65[b] |
|---|---|---|---|
| QEA-A-001-NH$_2$ (retinyl amine) | 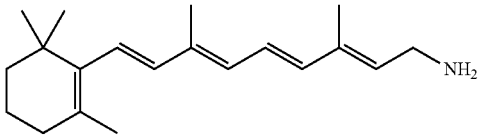 [SMILES: CC1=C(/C=C/C(C)=C/C=C/C(C)=C/CN)C(C)(C)CCC1] | 100% | Strong |
| QEA-A-002-NH$_2$ | 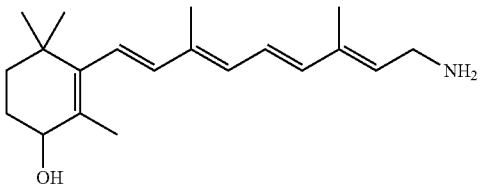 [SMILES: CC1=C(/C=C/C(C)=C/C=C/C(C)=C/CN)C(C)(C)CCC1O] | 100% | Strong |
| QEA-A-003-NH$_2$ | 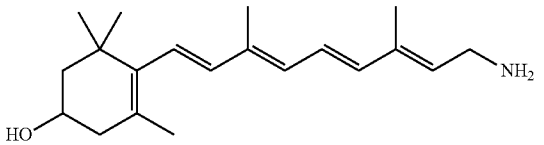 [SMILES: CC1=C(/C=C/C(C)=C/C=C/C(C)=C/CN)C(C)(C)CC(O)C1] | 100% | Strong |
| QEA-A-004-NH$_2$ | 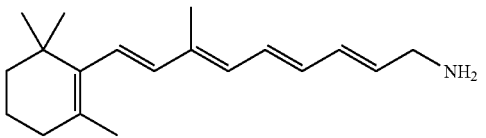 [SMILES: CC1=C(/C=C/C(C)=C/C=C/C=C/CN)C(C)(C)CCC1] | 100% | Strong |
| QEA-A-005-NH$_2$ | 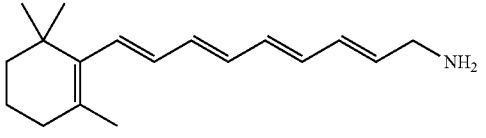 [SMILES: CC1=C(/C=C/C=C/C=C/C=C/CN)C(C)(C)CCC1] | 100% | Strong |
| QEA-A-006-NH$_2$ | 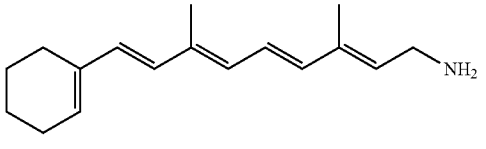 [SMILES: CC(/C=C/C1=CCCCC1)=C\C=C\C(C)=C\CN] | 100% | Moderate |
| QEA-B-001-NH$_2$ | 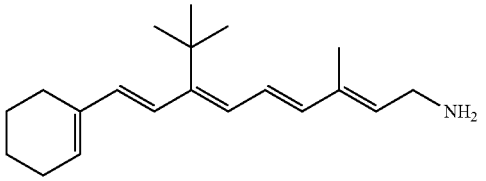 [SMILES: CC(/C=C/C=C(/C=C/C1=CCCCC1)C(C)(C)C)=C\CN] | 80% | None |

TABLE 1-continued

Summary of primary amines as substrates for LRAT and RPE65 in vitro

| Compound | Structure | LRAT Substrate[a] | Inhibition of RPE65[b] |
|---|---|---|---|
| QEA-B-002-NH$_2$ | 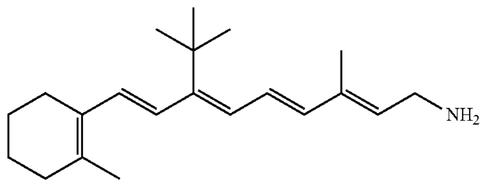 [SMILES: CC1=C(/C=C/C(=C/C=C/C(C)=C/CN)C(C)(C)C)CCCC1] | 30% | None |
| QEA-B-003-NH$_2$ | 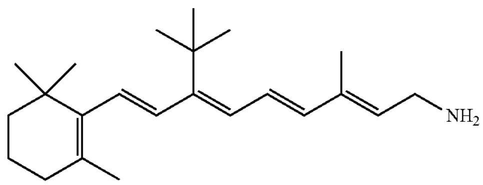 [SMILES: CC1=C(/C=C/C(=C/C=C/C(C)=C/CN)C(C)(C)C)C(C)(C)CCC1] | 100% | Moderate |
| QEA-B-004-NH$_2$ | 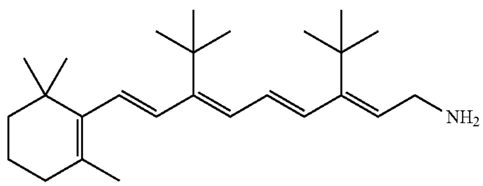 [SMILES: CC1=C(/C=C/C(=C/C=C/C(=C/CN)C(C)(C)C)C(C)(C)C)C(C)(C)CCC1] | 0 | —[c] |
| QEA-B-005-NH$_2$ | 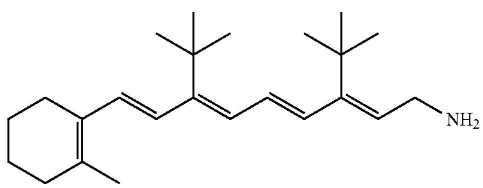 [SMILES: CC1=C(/C=C/C(=C/C=C/C(=C/CN)C(C)(C)C)C(C)(C)C)CCCC1] | 0 | —[c] |
| QEA-C-001-NH$_2$ | 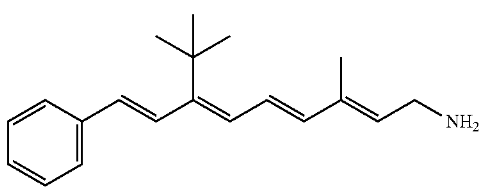 [SMILES: CC(/C=C/C=C(/C=C/c1ccccc1)C(C)(C)C)=C\CN] | 50% | None |
| QEA-C-002-NH$_2$ | 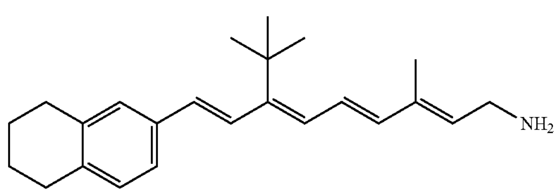 [SMILES: CC(/C=C/C=C(/C=C/c1ccc2c(c1)CCCC2)C(C)(C)C)=C\CN] | 15% | None |
| QEA-C-003-NH$_2$ | 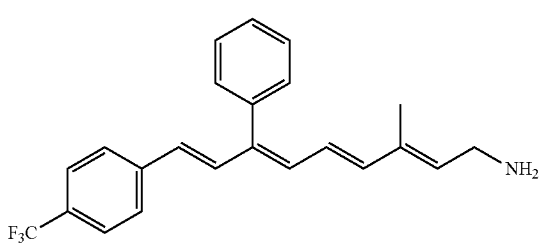 [SMILES: CC(/C=C/C=C(/C=C/c1ccc(C(F)(F)F)cc1)c1ccccc1)=C\CN] | 100% | None |

TABLE 1-continued

Summary of primary amines as substrates for LRAT and RPE65 in vitro

| Compound | Structure | LRAT Substrate[a] | Inhibition of RPE65[b] |
|---|---|---|---|
| QEA-C-004-NH$_2$ | 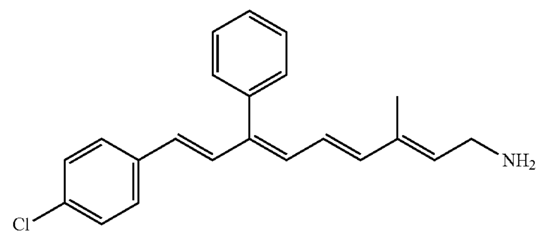 [SMILES: CC(/C=C/C=C(/C=C/c1ccc(Cl)cc1)c1ccccc1)=C\CN] | 100% | None |
| QEA-C-005-NH$_2$ | 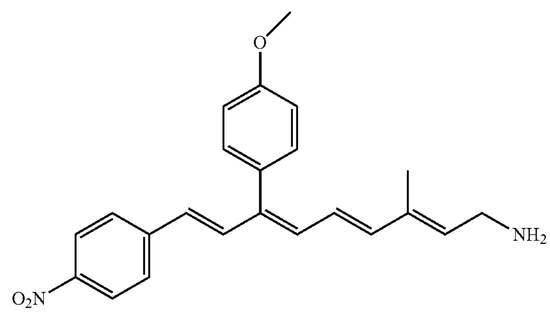 [SMILES: COc1ccc(C(=C\C=C\C(C)=C\CN)/C=C/c2ccc([N+](=O)[O-])cc2)cc1] | 100% | None |
| QEA-C-006-NH$_2$ | 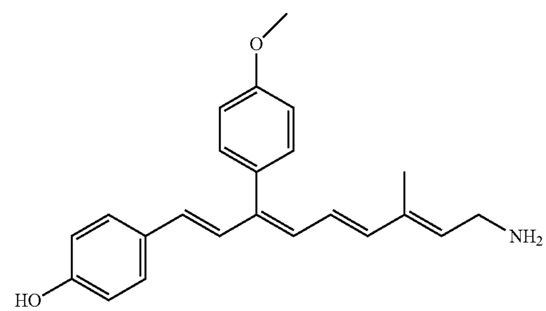 [SMILES: COc1ccc(C(=C\C=C\C(C)=C\CN)/C=C/c2ccc(O)cc2)cc1] | 50% | None |
| QEA-D-001-NH$_2$ | 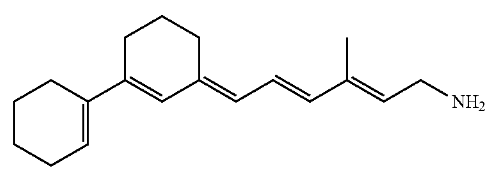 [SMILES: CC(/C=C/C=C1/C=C(C2=CCCCC2)CCC1)=C\CN] | 100% | None |
| QEA-D-002-NH$_2$ | 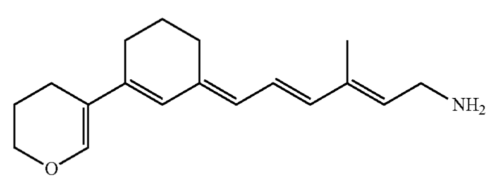 [SMILES: CC(/C=C/C=C1/C=C(C2=COCCC2)CCC1)=C\CN] | 100% | None |
| QEA-E-001-NH$_2$ | 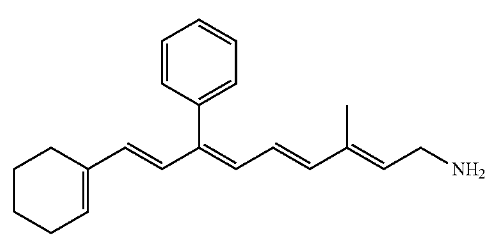 [SMILES: CC(/C=C/C=C(/C=C/C1=CCCCC1)c1ccccc1)=C\CN] | 100% | None |

TABLE 1-continued

Summary of primary amines as substrates for LRAT and RPE65 in vitro

| Compound | Structure | LRAT Substrate[a] | Inhibition of RPE65[b] |
|---|---|---|---|
| QEA-E-002-NH$_2$ | 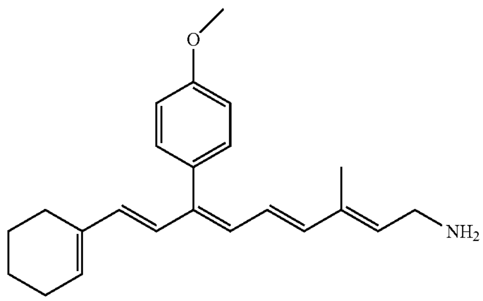 [SMILES: COc1ccc(C(=C\C=C\C(C)=C\CN)/C=C/C2=CCCCC2)cc1] | 100% | None |
| QEA-F-001-NH$_2$ | 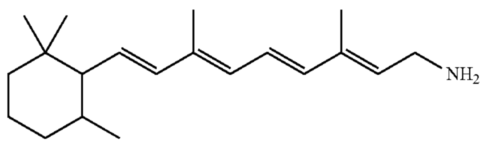 [SMILES: CC(/C=C/C1C(C)CCCC1(C)C)=C\C=C\C(C)=C\CN] | —[c] | —[c] |
| QEA-F-002-NH$_2$ | 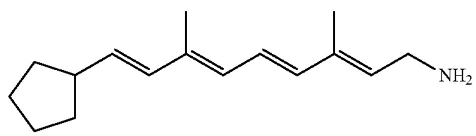 [SMILES: CC(/C=C/C1CCCC1)=C\C=C\C(C)=C\CN] | —[c] | —[c] |
| QEA-G-001-NH$_2$ | 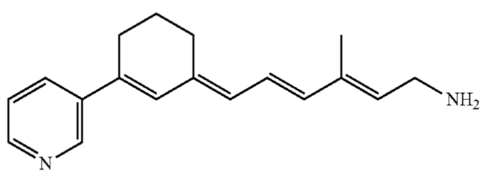 [SMILES: CC(/C=C/C=C1/C=C(c2cccnc2)CCC1)=C\CN] | 100% | Moderate |
| QEA-G-002-NH$_2$ | 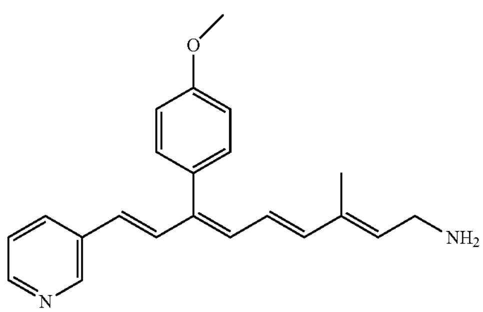 [SMILES: COc1ccc(C(=C\C=C\C(C)=C\CN)/C=C/c2cccnc2)cc1] | 100% | Moderate |
| TEA-A-001-NH$_2$ | 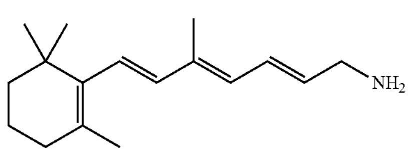 [SMILES: CC1=C(/C=C/C(C)=C/C=C/CN)C(C)(C)CCC1] | 100% | Strong |
| TEA-A-002-NH$_2$ | 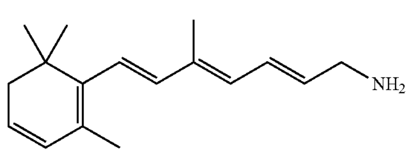 [SMILES: CC1=C(/C=C/C(C)=C/C=C/CN)C(C)(C)CC=C1] | 100% | Strong |
| TEA-A-003-NH$_2$ | 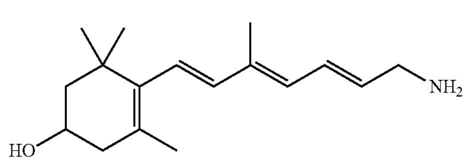 [SMILES: CC1=C(/C=C/C(C)=C/C=C/CN)C(C)(C)CC(O)C1] | 90% | Strong |

TABLE 1-continued

Summary of primary amines as substrates for LRAT and RPE65 in vitro

| Compound | Structure | LRAT Substrate[a] | Inhibition of RPE65[b] |
|---|---|---|---|
| TEA-A-004-NH₂ | | 90% | Strong |
| TEA-B-001-NH₂ | | 100% | None |
| TEA-B-002-NH₂ | | 10% | None |
| TEA-B-003-NH₂ | | 20% | None |
| TEA-B-004-NH₂ | | 30% | None |
| TEA-C-001-NH₂ | | 0 | —[c] |
| TEA-C-002-NH₂ | | 20% | None |

TABLE 1-continued

Summary of primary amines as substrates for LRAT and RPE65 in vitro

| Compound | Structure | LRAT Substrate[a] | Inhibition of RPE65[b] |
|---|---|---|---|
| PEA-A-001-NH$_2$ | 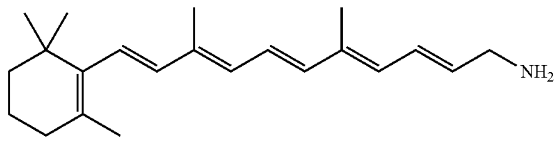 [SMILES: CC1=C(/C=C/C(C)=C/C=C/C(C)=C/C=C/CN)C(C)(C)CCC1] | 100% | Strong |
| PEA-A-002-NH$_2$ | 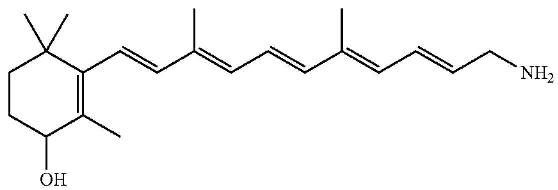 [SMILES: CC1=C(/C=C/C(C)=C/C=C/C(C)=C/C=C/CN)C(C)(C)CCC1O] | 90% | Strong |
| PEA-A-003-NH$_2$ | 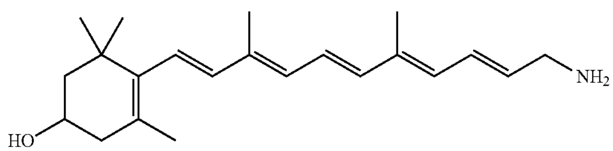 [SMILES: CC1=C(/C=C/C(C)=C/C=C/C(C)=C/C=C/CN)C(C)(C)CC(O)C1] | 90% | Strong |

[a]LRAT substrates were assessed as percentages of their corresponding primary alcohols that were esterified by LRAT in 1 h at 37° C.
[b]'Strong' inhibition indicates that the IC$_{50}$ of the tested amine was below 10 μM; 'moderate' inhibition means that IC$_{50}$ was between 10-100 μM; and 'none' signifies that the IC$_{50}$ was above 200 μM.
[c]Not tested.

Protective Effects of Primary Amines Against Light-Induced Retinal Degeneration

Our in vitro screening identified 17 candidates which could be acylated by LRAT and yet did not inhibit RPE65. For practical reasons, only eight of these leading compounds (QEA-B-001-NH$_2$, B-002-NH$_2$, C-001-NH$_2$, C-003-NH$_2$, C006-NH$_2$, E-002-NH$_2$, TEA-B-002-NH$_2$, and C00-2-NH$_2$) along with retinylamine as a control were selected for further testing in Abca4$^{-/-}$ Rdh8$^{-/-}$ mice, an animal model for light-induced retinal degeneration (Table 2). Additionally, two novel amines with moderate inhibition of RPE65 (QEA-A-006-NH$_2$ and QEA-B-003-NH$_2$) and one with strong inhibition (QEA-A-005-NH$_2$) were added to the first test group for comparison. Mice were gavaged with 1 mg of a test compound and then kept in the dark for 24 h prior to being exposed to bright light (~10,000 lux) for 1 h. Retinal damage was assessed with OCT that measured the thickness of the outer nuclear layer and by quantification of tissue 11-cis retinal levels. An example is shown for imaging results in FIG. 4A and for 11-cis-retinal quantification in FIG. 4B. Additionally, extracts of livers obtained from treated mice were analyzed by HPLC to estimate the amounts of corresponding amides (FIG. 4C).

As shown in Table 2, compounds characterized as weak inhibitors did not prevent retinal deterioration. One possible explanation is that instability of these compounds in vivo caused their failure to protect. Despite being substrates for LRAT, seven compounds (QEA-A-006-NH$_2$, B-002-NH$_2$, B-003 NH$_2$, C-003-NH$_2$, C-006-NH$_2$, E-002-NH$_2$, and TEA-B-002-NH$_2$) were not efficiently amidated in vivo as shown by lack of accumulation of their amide forms in mouse liver. Whether these compounds were removed from the biological system before or after amidation by LRAT is not clear.

TABLE 2

Protective effects of primary amines against intense light-induced retinal degeneration in 4-week-old Abca4$^{-/-}$Rdh8$^{-/-}$ mice[a]

| Compound | Structure | Protection by amide in liver | Toxicity |
|---|---|---|---|
| QEA-A-001-NH$_2$ (retinylamine) | 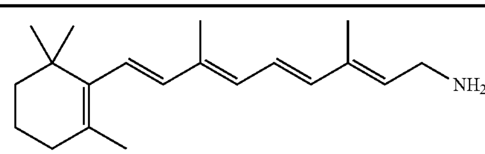 | Strong | None |
| QEA-A-005-NH$_2$ | 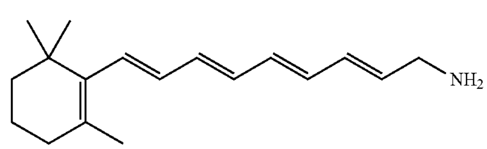 [SMILES: CC1=C(/C=C/C=C/C=C/C=C/CN)C(C)(C)CCC1] | Strong | None |

TABLE 2-continued
Protective effects of primary amines against intense light-induced retinal degeneration in 4-week-old Abca4⁻/⁻Rdh8⁻/⁻ mice[a]
| Compound | Structure | Protection by amide in liver | Toxicity |
|---|---|---|---|
| QEA-A-006-NH$_2$ | 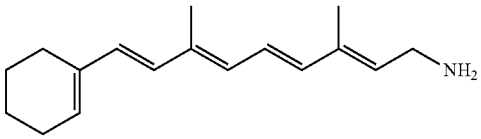 [SMILES: CC(/C=C/C1=CCCCC1)=C\C=C\C(C)=C\CN] | None | None |
| QEA-B-001-NH$_2$ | 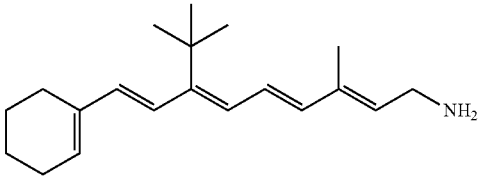 [SMILES: CC(/C=C/C=C(/C=C/C1=CCCCC1)C(C)(C)C)=C\CN] | Strong | Yes |
| QEA-B-002-NH$_2$ | 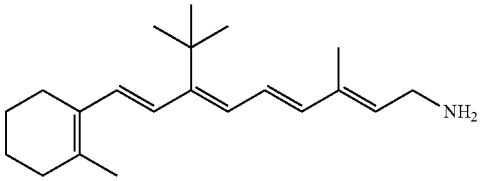 [SMILES: CC1=C(/C=C/C(=C/C=C/C(C)=C/CN)C(C)(C)C)CCCC1] | None | None |
| QEA-B-003-NH$_2$ | 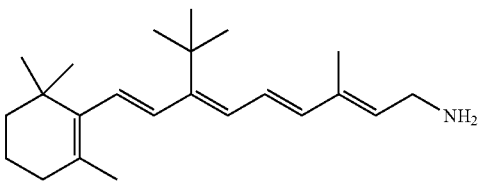 [SMILES: CC1=C(/C=C/C(=C/C=C/C(C)=C/CN)C(C)(C)C)C(C)(C)CCC1] | Weak | None |
| QEA-C-001-NH$_2$ | 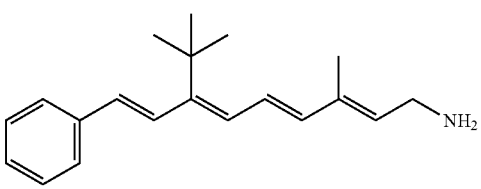 [SMILES: CC(/C=C/C=C(/C=C/c1ccccc1)C(C)(C)C)=C\CN] | Strong | Yes |
| QEA-C-003-NH$_2$ | 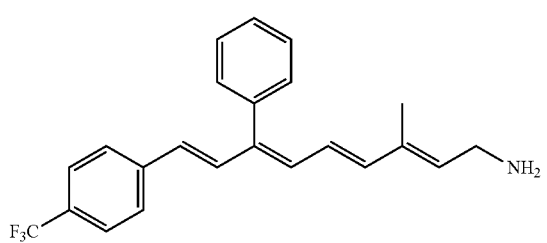 [SMILES: CC(/C=C/C=C(/C=C/c1ccc(C(F)(F)F)cc1)c1ccccc1)=C\CN] | None | Yes |
| QEA-C-006-NH$_2$ | 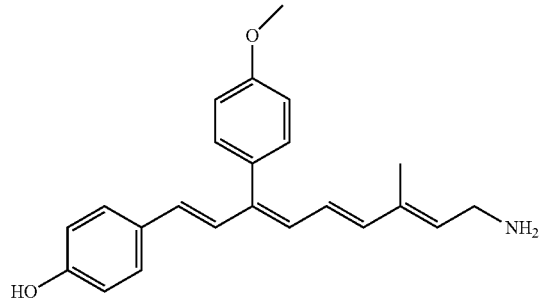 [SMILES: COc1ccc(C(=C\C=C\C(C)=C\CN)/C=C/c2ccc(O)cc2)cc1] | None | None |

TABLE 2-continued

Protective effects of primary amines against intense light-induced retinal degeneration in 4-week-old Abca4$^{-/-}$Rdh8$^{-/-}$ mice$^a$

| Compound | Structure | Protection by amide in liver | Toxicity |
|---|---|---|---|
| QEA-E-002-NH$_2$ | 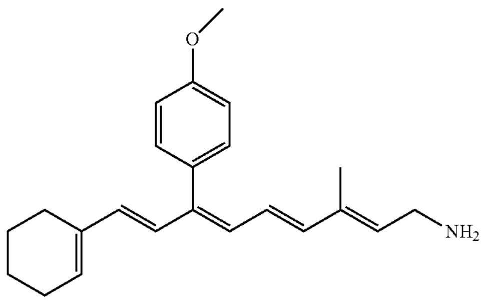 [SMILES: COc1ccc(C(=C\C=C\C(C)=C\CN)/C=C/C2=CCCCC2)cc1] | Weak | None |
| TEA-B-002-NH$_2$ | 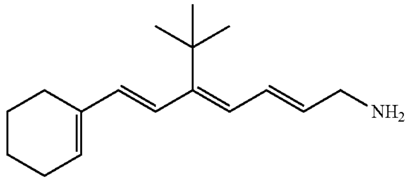 [SMILES: CC(C)(C)C(=C\C=C\CN)/C=C/C1=CCCCC1] | None | Yes |
| TEA-C-002-NH$_2$ | 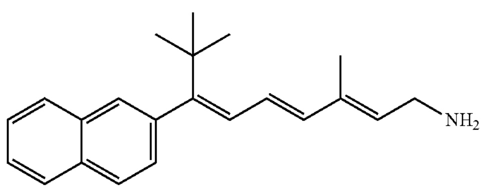 [SMILES: CC(/C=C/C=C(/c1ccc2ccccc2c1)C(C)(C)C)=C\CN] | Strong | Yes |

$^a$Abca4$^{-/-}$Rdh8$^{-/-}$ mice treated with tested amines were kept in the dark for 24 h, and then bleached with 10,000 lux light for 1 h as described in the Methods section.

Nonetheless, inadequate levels of primary amines in vivo would have resulted from either scenario. Thus, it was not surprising to observe retinal degeneration in OCT images of mice treated with these amines (FIG. 4A). In contrast, compounds QEA-B-001-NH$_2$, C-001-NH$_2$, and TEA-C-002-NH$_2$ that did not inhibit RPE65 were efficiently converted into amides in vivo as was apparent form their intense amide peaks present in liver. Levels of 11-cis-retinal quantified 1 week after light exposure indicated that only 50% of photoreceptors remained as compared to those in control healthy mice (FIG. 4B). Although QEA-B-001-NH$_2$ was stored as an amide in liver, its inability to prevent light-induced retinal degeneration could be attributed to an insufficient concentration of free amine in eyes needed to sequester the excess of all-trans-retinal produced by bleaching.

Functional Relationship Between Inhibition of the Visual Cycle and Retinal Protection As indicated above, inhibition of RPE65 can protect the retina against light-induced damage. However, a fundamental question is to what extent does RPE65 enzymatic activity need to be affected to achieve this therapeutic effect. To answer this question, we measured the rate of the visual chromophore recovery in WT mice pretreated with retinylamine and exposed to light illumination that activated ~90% of rhodopsin yet failed to trigger retinal degeneration. As demonstrated in FIG. 5A, mice without treatment had recovered ~85±5% of the pre-bleached 11-cis-retinal level in the eye at 6 h, whereas mice exposed to light 2 h after administration of 0.2 mg of retinylamine recovered only 50±13%. Importantly, animals treated with the same amount of retinylamine but exposed to light 24 h later exhibited a much slower recovery of 11-cis-retinal in the eye, namely only 22±5.0% of the pre-bleached level (FIG. 5B). When the retinylamine inhibitory effect was investigated over a broader time period (FIG. 5C), 24 h postadministration was found to be the time point with the strongest inhibition regardless of a 5 fold difference in the retinylamine dose. The inhibitory effect observed for the 0.2 mg dose decreased by day 3, resulting in 61±2.2% of recovered 11-cis-retinal, and nearly disappeared by day 7. In contrast, 0.5 mg of retinylamine still strongly affected the rate of 11-cis-retinal regeneration at 7 days, allowing only a partial recovery (56±9.1%).

Once the time course of retinylamine's inhibitory effect was established, we investigated the correlation between the level of inhibition and the protective effect on the retina. Four week old Abca4$^{-/-}$Rdh8$^{-/-}$ mice were gavaged with 0.1, 0.2, and 0.5 mg of retinylamine, respectively, and kept in the dark for 24 h. Mice then were bleached with 10,000 lux bright light for 1 h. Measured as described above, the recovery of visual chromophore was inhibited by about 40%, 80%, and 95%, respectively by these tested drug doses (FIGS. 5B and 5C). Bleached mice were kept in the dark for 3 d, and then imaged by OCT (FIGS. 6A and 6B). Mice treated with only 0.1 mg of retinylamine developed severe retinal degeneration, similar to that observed in mice without treatment, whereas mice treated with 0.5 mg retinylamine showed a clear intact ONL image. The average ONL thickness in the latter group of mice was 51.1±5.8 μm, well within the range of healthy retinas. Concurrently, OCT imaging revealed that mice treated with the 0.2 mg dose were partially protected. Their average ONL thickness was 34.4±17.4 μm. Notably, changes in the ONL appearance observed 3 days after light exposure did not necessarily represent permanent retinal damage. In an equivalent experiment, mice were kept in the dark for 7 days prior to quantification of visual chromophore levels. (Amounts of 11-cis-retinal reflect the concentration of rhodopsin and thus can be used to verify the health of photoreceptor cells). Mice treated with 0.2 mg of retinylamine showed the same 11-cis-retinal levels (445±37 pmol/eye) as control mice not exposed to light (452±43 pmol/eye), whereas mice gavaged with a 0.1 mg dose and untreated animals had 323±48 pmol/eye and 301±8 pmol/eye, respectively, suggesting irreversible damage to the retina (FIG. 6C). Furthermore, mice treated with the 0.2 mg and 0.5 mg doses of retinylamine showed the same ERG scotopic a wave responses as unbleached control mice, whereas animals provided with 0.1 mg of the drug revealed attenuated ERG responses similar to those of untreated controls (FIG. 6D). Thus, the 0.1 mg dose failed to protect against retinal degeneration under the bright light exposure conditions described in this study.

Chemical Synthesis of Compounds Used in this Study

TEA-A-001 (5-Methyl-7-(2,6,6-trimethyl-cyclohex-1-enyl)-hepta-2,4,6-trienal)

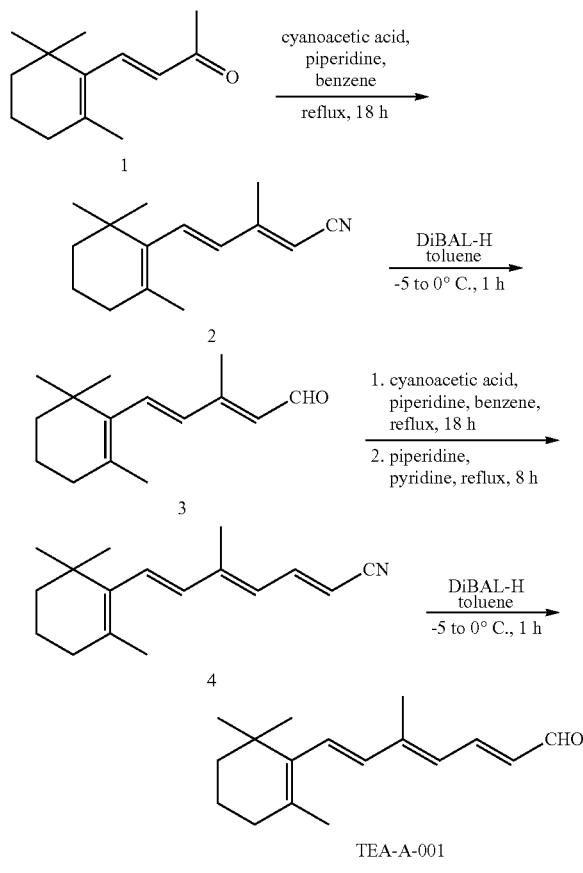

Preparation of Compound-2: To a stirred solution of Compound-1 (20 g, 10 mmol) in benzene (120 mL) at 0° C. was added a solution of cyanoacetic acid (17.6 g, 20 mmol) followed by piperidine (20 mL) and the resulting mixture was refluxed for 18 h. After cooling to room temperature, the mixture was diluted with water (200 mL) and the aqueous layer was extracted with ethyl acetate (3×200 mL). The combined organic layers were dried over anhydrous $Na_2SO_4$ and concentrated. The residue was purified by column chromatography on 60-120 mesh silica gel and eluted with 0.5% ethyl acetate/petroleum ether to obtain Compound-2 (19.3 g, 86%). MS (m/z): $[M+H]^+$, 216.

Preparation of Compound-3: To a stirred solution of Compound-2 (19.3 g, 89.6 mmol) in dry toluene (96 mL) at −5° C. was slowly added DIBAL-H (1 M in toluene, 89.6 mL) and the reaction mixture was stirred at 0° C. for 1 h. A chilled 1 M $H_2SO_4$ solution was added and the resulting mixture was extracted thrice with ether. The combined organic layers were dried over anhydrous $Na_2SO_4$ and concentrated. The residue was purified by column chromatography on 60-120 mesh silica gel and eluted with 0.5% ethyl acetate/petroleum ether to obtain Compound-3 (15.6 g, 79.7%). MS (m/z): $[M+H]^+$, 219.

Preparation of Compound-4: To a stirred solution of Compound-3 (8.3 g, 38 mmol) in benzene (50 mL) cooled to 0° C. was slowly added a solution of cyanoacetic acid (7.12 g, 76 mmol) followed by piperidine (82 mL). The resulting mixture was refluxed for 18 h, and then evaporated under vacuum. The residue was dissolved in piperidine (25 mL) and pyridine (25 mL). The resulting solution was refluxed for 8 h, and then evaporated under vacuum. The residue was washed with cold 1 M HCl solution and brine, dried over anhydrous $Na_2SO_4$ and concentrated. The residue was purified by column chromatography on 60-120 mesh silica gel and eluted with 40% DCM/petroleum ether to obtain Compound-4 (3.4 g, 37%). MS (m/z): $[M+H]^+$, 242.

Preparation of TEA-A-001: To a stirred solution of Compound-4 (3.4 g, 14 mmol) in dry toluene (17.5 mL) at −5° C. was slowly added DIBAL-H (1 M in toluene, 14 mL) and the reaction mixture was stirred at 0° C. for 1 h. The reaction was quenched with a chilled 1 M $H_2SO_4$ solution and extracted thrice with ether. The combined organic layers were dried over anhydrous $Na_2SO_4$ and concentrated. The residue was purified by column chromatography on 60-120 mesh silica gel and eluted with 30% of DCM/petroleum ether to obtain TEA-A-001 (800 mg, 23.3%). $^1$H NMR ($CDCl_3$, 400 MHz): δ 1.04 (s, 6H), 1.46-1.49 (m, 2H), 1.58-1.64 (m, 2H), 1.73 (d, J=0.8 Hz, 3H), 2.04 (t, J=6.4 Hz, 2H), 2.09 (d, J=0.8 Hz, 3H), 6.14-6.23 (m, 2H), 6.29 (d, J=12 Hz, 1H), 6.50 (d, J=16.4 Hz, 1H), 7.54 (dd, J=12 Hz, 15.2 Hz, 1H), 9.61 (d, J=8 Hz, 1H); $^{13}$C NMR ($CDCl_3$, 100 MHz): δ 10.79, 16.75, 19.44, 26.61, 30.85, 31.91, 37.21, 125.1, 128.4, 129.3, 130.2, 134.1, 135.0, 144.5, 145.8, 191.4. MS (m/z): $[M+H]^+$, 245.3.

TEA-A-002 (5-Methyl-7-(2,6,6-trimethyl-cyclohexa-1,3-dienyl)-hepta-2,4,6-trienal) and TEA-A-003 (7-(3-Hydroxy-2,6,6-trimethyl-cyclohex-1-enyl)-5-methyl-hepta-2,4,6-trienal)

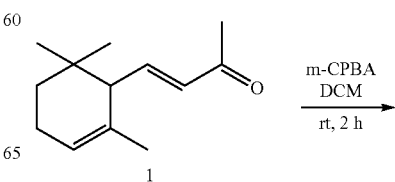

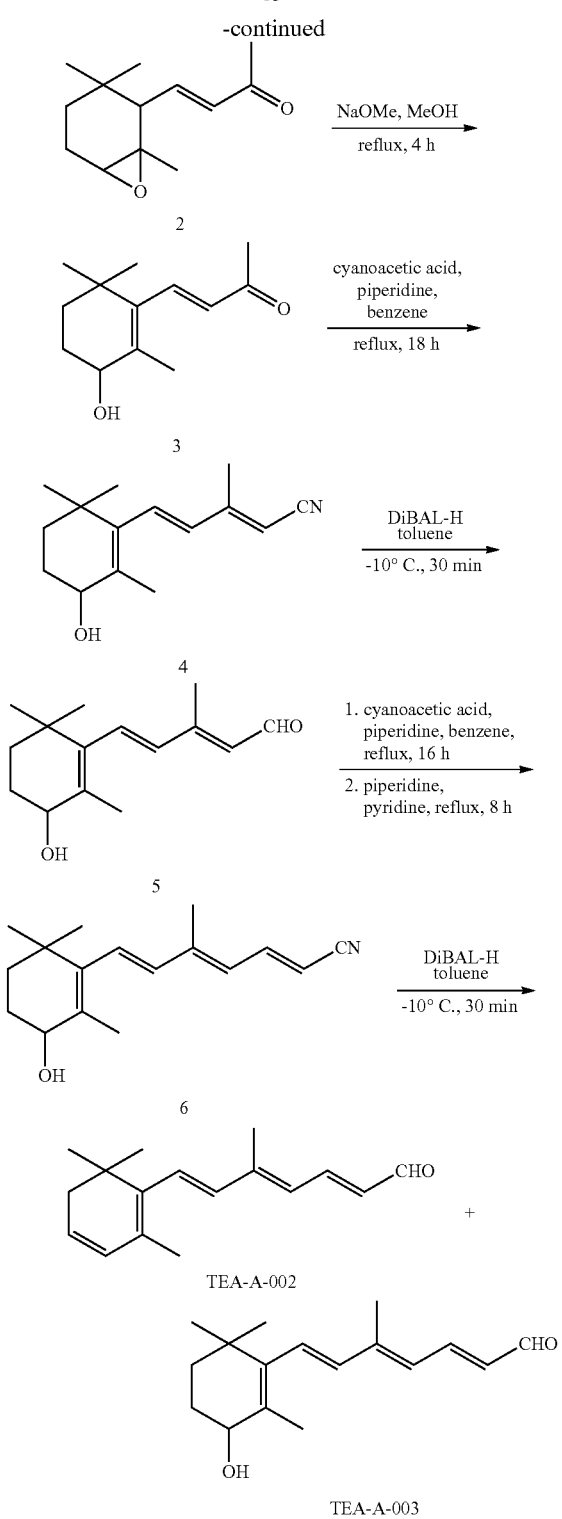

obtain Compound-2 (10.2 g). The crude material was used for the next step without further purification. MS (m/z): [M+H]$^+$, 209.2.

Preparation of Compound-3: To a stirred solution of NaOMe (18 mmol) in methanol (50 mL) was slowly added a solution of Compound-2 (12.5 g, 60 mmol) in methanol (15 mL) and the solution was refluxed for 4 h. Then the solution was neutralized to pH 7 with diluted acetic acid and evaporated under vacuum. The residue was poured into water (300 mL) and the aqueous layer was extracted with ethyl acetate (5×100 mL). The combined organic layers were washed with brine, dried over anhydrous Na$_2$SO$_4$ and concentrated. The crude compound was purified by column chromatography on 60-120 mesh silica gel and eluted with 15% of ethyl acetate/petroleum ether to obtain Compound-3 (3.7 g, 42.7% for 2 steps). MS (m/z): [M+H]$^+$, 209.2.

Preparation of Compound-4: To a stirred solution of Compound-3 (8.5 g, 40.8 mmol) in benzene (15 mL) at 0° C. was added cyanoacetic acid (6.94 g, 81 mmol) followed by piperidine (8.1 mL, 81 mmol). The reaction mixture was refluxed for 18 h and then cooled to room temperature. Water (100 mL) was added and the resulting aqueous layer was extracted with ethyl acetate (5×100 mL). The combined organic layers were dried over anhydrous Na$_2$SO$_4$ and concentrated. The crude compound was purified by column chromatography on 100-200 mesh silica gel and eluted with 12% ethyl acetate/petroleum ether to obtain Compound-4 (8.2 g, 86.9%). MS (m/z): [M–OH]$^+$, 214.2.

Preparation of Compound-5: To a stirred solution of Compound-4 (8.3 g, 35 mmol) in dry toluene (45 mL) at −10° C. under a nitrogen atmosphere was added dropwise DIBAL-H (1 M in toluene, 71.8 mL). The reaction mixture was stirred at −10° C. for 30 min. Then 1 M H$_2$SO$_4$ (20 mL) solution was added and the resulting mixture was extracted with ether (6×100 mL). The combined organic layers were washed with brine, dried over anhydrous Na$_2$SO$_4$ and concentrated. The crude compound was purified by column chromatography on 60-120 mesh silica gel and eluted with 15% ethyl acetate/petroleum ether to obtain Compound-5 (3 g, 35.7%). MS (m/z): [M–OH]$^+$, 217.1.

Preparation of Compound-6: To a stirred solution of Compound-5 (3.0 g, 12.8 mmol in benzene (10 mL) at 0° C. was added a solution of cyanoacetic acid (2.17 g, 25 mmol) followed by piperidine (3 mL, 25 mmol). The reaction mixture was refluxed for 16 h and then evaporated under vacuum. A solution of piperidine (20 mL) and pyridine (20 mL) was added and the resulting solution was refluxed for 8 h before being evaporated again under vacuum. The residue was diluted with water and extracted with ethyl acetate (200 mL). The combined organic layers were washed with chilled 1 M HCl solution, dried over anhydrous Na$_2$SO$_4$ and concentrated to obtain Compound-6 (750 mg, 22.7%). MS (m/z): [M–OH]$^+$, 240.3.

Preparation of TEA-A-002 and TEA-A-003: To a stirred solution of Compound-7 (750 mg, 2.9 mmol) in dry toluene (4 mL) at −10° C. was slowly added DIBAL-H (1 M in toluene, 5.83 mL). The reaction mixture was stirred for at 0° C. for 30 min, quenched with a cooled saturated sodium potassium tartrate solution and filtered through celite. The filtrate was extracted twice with chloroform. The combined organic layers were dried over anhydrous Na$_2$SO$_4$ and concentrated. The residue was purified by column chromatography on 60-120 mesh silica gel and eluted with 6% ethyl acetate/petroleum ether to obtain TEA-A-002 (60 mg, 2.4% based on Compound-5) and TEA-A-003 (80 mg, 2.6% based on Compound-5). TEA-A-002: $^1$H NMR (CDCl$_3$, 400 MHz): δ 1.05 (s, 6H), 1.88 (s, 3H), 2.09 (m, 2H), 2.11 (d, Preparation of Compound-2: To a stirred solution of Compound-1 (8 g, 41.6 mmol) in dry DCM (120 mL) at 0° C. was slowly added m-CPBA (15.8 g, 91 mmol). The resulting mixture was stirred at room temperature for 2 h. Then the mixture was filtered and the precipitate was washed with DCM. The combined filtrate was washed serially with 10% aq. Na$_2$SO$_3$, 5% aq. NaOH, water and brine, dried over anhydrous Na$_2$SO$_4$ and concentrated to J=0.8 Hz, 3H), 5.79 (m, 1H), 5.87 (d, J=7.6 Hz, 1H), 6.18 (dd, J=14.8 Hz, 8 Hz, 2H), 6.34 (m, 2H), 6.51 (d, J=16 Hz, 1H), 7.54 (dd, J=14.8 Hz, 12 Hz, 1H), 9.61 (d, J=8 Hz, 1H); $^{13}$C NMR (CDCl$_3$, 100 MHz): δ 13.27, 20.60, 26.97, 29.92, 34.25, 40.10, 126.5, 128.1, 129.1, 130.0, 131.0, 131.5, 135.9, 138.0, 146.8, 148.1, 193.9. IR: 1676 cm$^{-1}$. MS (m/z): [M+H]$^+$, 243.2.

TEA-A-003: $^1$H NMR (CDCl$_3$, 400 MHz): δ 1.02 (s, 3H), 1.05 (s, 3H), 1.40-1.48 (m, 1H), 1.62-1.76 (m, 2H), 1.83 (s, 3H), 1.84-1.96 (m, 1H), 2.09 (d, J=1.2 Hz, 3H), 4.02 (t, J=4.8 Hz, 1H), 6.15-6.24 (m, 2H), 6.30 (d, J=11.6 Hz, 1H), 6.44 (d, J=16 Hz, 1H), 7.53 (dd, J=12 Hz, 15.2 Hz, 1H), 9.61 (d, J=8 Hz, 1H); $^{13}$C NMR (CDCl$_3$, 100 MHz): δ 13.36, 18.88, 27.76, 28.62, 29.25, 29.92, 34.73, 35.04, 70.33, 128.4, 131.4, 131.7, 137.8, 141.4, 146.3, 148.0, 194.0. IR: 3418, 1677 cm$^{-1}$. MS (m/z): [M+H]$^+$, 243.2.

TEA-A-004 (7-(4-Hydroxy-2,6,6-trimethyl-cyclohex-1-enyl)-5-methyl-hepta-2,4,6-trienal)

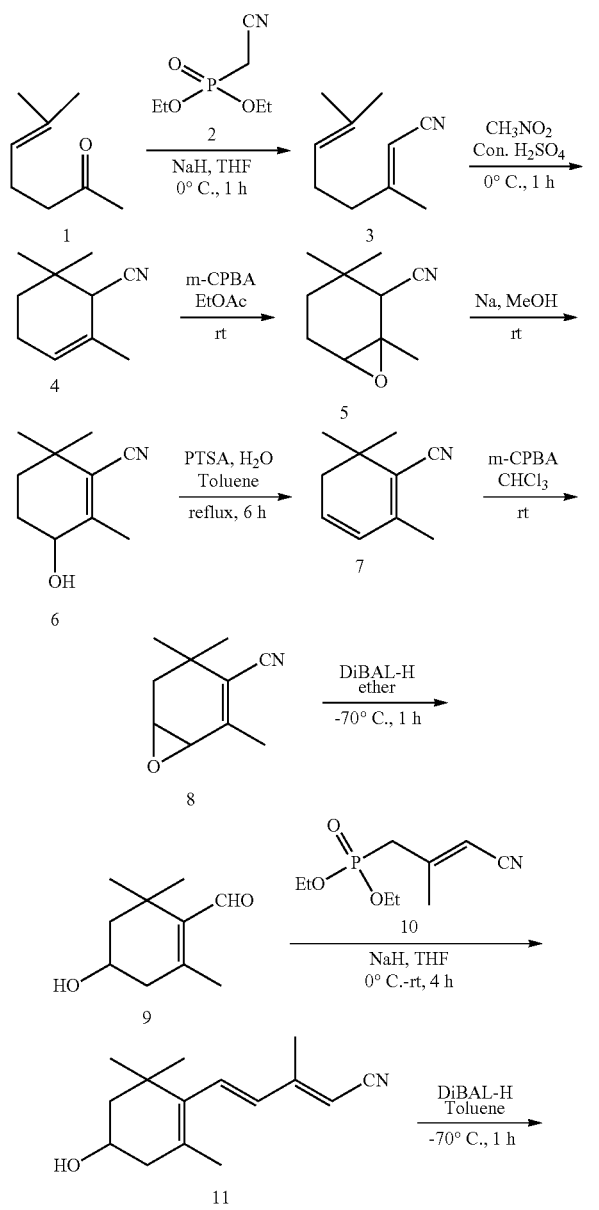

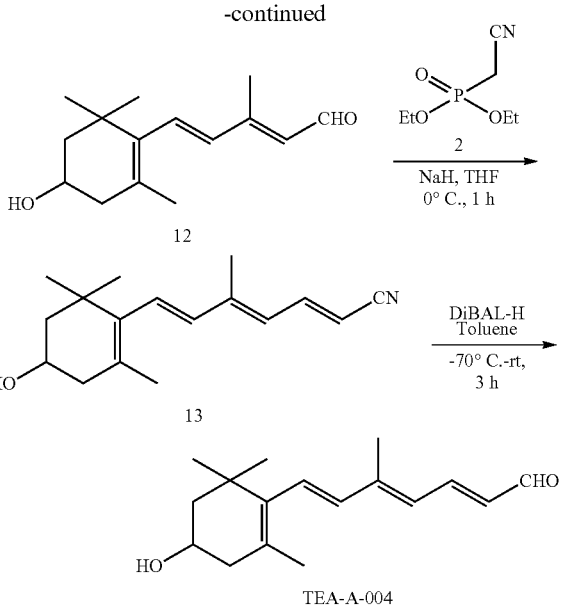

TEA-A-004

Preparation of Compound-3: To a stirred suspension of NaH (141 g, 3.52 mol) in THF (7.4 L) at 0° C. was added dropwise a solution of Compound-2 (571.7 g, 3.23 mol) in dry THF (10 mL). The reaction mixture was stirred at 0° C. for 30 min and a solution of Compound-1 (370 g, 2.937 mol) in THF (10 mL) was slowly added. The resulting mixture was stirred at room temperature for 1 h. The reaction was quenched with diluted HCl and the resulting mixture was extracted thrice with ethyl acetate. The combined organic layers were washed with brine, dried over anhydrous sodium sulfate and concentrated. The crude compound was purified by column chromatography on 60-120 mesh silica gel and eluted with 1% ethyl acetate/petroleum ether to obtain Compound-3 (370 g, 84.4%). MS (m/z): [M+H]$^+$, 150.2.

Preparation of Compound-4: To a solution of conc. H$_2$SO$_4$ (360 mL) at 0° C. was added dropwise a solution of compound-3 (120 g, 0.8 mole) in nitromethane (3 L). The mixture was stirred for 1 h at 0° C. Then the reaction was quenched with ice and the resulting mixture was extracted thrice with ether. The combined organic layers were washed with NaHCO$_3$ solution, dried over anhydrous Na$_2$SO$_4$ and concentrated. The crude compound was purified by column chromatography on 60-120 mesh silica gel and eluted with 1% ethyl acetate/petroleum ether to obtain Compound-4 (82 g, 68.7%). MS (m/z): [M+H]$^+$, 150.2. Preparation of Compound-5: To a stirred solution of m-CPBA (217 g, 0.88 mol) in ethyl acetate (787 mL) cooled to 0° C. was added a solution of Compound-4 (65.6 g, 0.44 mol) and the solution was stirred at room temperature overnight. Then the reaction was quenched with TEA at 0° C. The resulting mixture was diluted with ethyl acetate and washed twice with water. The organic layer was dried over anhydrous sodium sulfate and concentrated. The crude compound was purified by column chromatography on 60-120 mesh silica gel and eluted with 4-5% ethyl acetate/petroleum ether to obtain Compound-5 (30 g, 41.2%). MS (m/z): [M+H]$^+$, 166.2.

Preparation of Compound-6: To a stirred solution of sodium (1.25 g, 54 mmol) in methanol (10 mL) at 0° C. was slowly added methanol (450 mL) followed by Compound-5 (30 g, 180 mmol) in methanol (10 mL). The resulting solution was stirred at room temperature overnight, and then evaporated under vacuum. The residue was diluted with water, neutralized with acetic acid and extracted thrice with ethyl acetate. The combined organic layers were washed with brine, dried over anhydrous $Na_2SO_4$ and concentrated. The crude compound was purified by column chromatography on 60-120 mesh silica gel and eluted with 20% ethyl acetate/petroleum ether to obtain Compound-6 (23 g, 77.3%). MS (m/z): [M+H]$^+$, 166.2.

Preparation of Compound-7: To a stirred solution of Compound-6 (16 g, 96 mmol) in dry toluene (160 mL) was added PTSA (6.47 g, 37.6 mmol) and the reaction mixture was refluxed for 6 h. Then the solution was cooled to room temperature and water (200 mL) was added. The resulting aqueous layer was extracted with ethyl acetate (3×200 mL). The combined organic layers were washed with an aq. $NaHCO_3$ solution, then brine, dried over anhydrous $Na_2SO_4$ and concentrated. The crude compound was purified by column chromatography on 60-120 mesh silica gel and eluted with 4% ethyl acetate/petroleum ether to obtain Compound-7 (6.5 g, 45.6%). MS (m/z): [M+H]$^+$, 148.2.

Preparation of Compound-8: To a stirred solution of m-CPBA (12 g, 48 mmol) in chloroform (72 mL) cooled to 0° C. was added a solution of Compound-7 (6 g, 40 mmol) in chloroform (10 mL) and the solution was stirred at room temperature overnight. The solution was cooled to 4° C. and both TEA and water were added. The resulting mixture was extracted with DCM. The organic layer was dried over anhydrous $Na_2SO_4$ and concentrated. The crude compound was purified by column chromatography on 60-120 mesh silica gel and eluted with 4% ethyl acetate/petroleum ether to obtain Compound-8 (4.9 g, 73.8%). MS (m/z): [M+H]$^+$, 164.2.

Preparation of Compound-9: To a stirred solution of Compound-8 (4.9 g, 30 mmol) in ether (49 mL) cooled to −60° C. under nitrogen was added dropwise DIBAL-H (1.7 M in toluene, 62 mL), and the resulting solution was stirred at room temperature for 3 h before cooling to −70° C. Then wet silica gel was added at −70° C. and the resulting mixture was stirred for 1 h. The mixture was filtered and the filtrate was dried over anhydrous $Na_2SO_4$ and concentrated. The crude compound was purified by column chromatography on 60-120 mesh silica gel and eluted with 20% ethyl acetate/petroleum ether to obtain Compound-9 (3.5 g, 70%). IR: 3406, 1668, 1611 cm$^{-1}$. MS (m/z): [M+H]$^+$, 169.2.

Preparation of Compound-11: To a stirred suspension of NaH (750 mg, 35 mmol) in dry THF (30 mL) at 0° C. was added a solution of Compound-10 (6.76 g, 35 mmol) in dry THF (10 mL). The resulting solution was stirred for 1 h, cooled to 0° C. and then a solution of Compound-9 (1.5 g, 8.9 mmol) in dry THF (10 mL) was slowly added. The reaction mixture was further stirred at room temperature for 3 h. The reaction was quenched with an $NH_4Cl$ solution and the resulting mixture was extracted thrice with ether. The combined organic layers were washed with brine, dried over anhydrous $Na_2SO_4$ and concentrated. The crude compound was purified by column chromatography on 60-120 mesh silica gel eluted with 20% ethyl acetate/petroleum ether to obtain Compound-11 (1 g, 48.6%). IR: 3407, 2211, 1617 cm$^{-1}$. MS (m/z): [M+H]$^+$, 214.3.

Preparation of Compound-12: To a stirred solution of Compound-11 (1 g, 4.3 mmol) in dry toluene (10 mL) at −60° C. under nitrogen was added dropwise DIBAL-H (1.7 M in toluene, 8.9 mL). After addition, the solution was stirred at −60° C. for 2 h and cooled to −70° C. Wet silica gel was added and the mixture was stirred at room temperature for 1 h. The reaction mixture was filtered and the filtrate was dried over anhydrous $Na_2SO_4$ and concentrated. The crude compound was purified by column chromatography on 60-120 mesh silica gel and eluted with 20% ethyl acetate/petroleum ether to obtain Compound-12 (830 mg, 83%). MS (m/z): [M+H]$^+$, 235.3.

Preparation of Compound-13: To a stirred suspension of NaH (149 mg, 6 mmol) in dry THF (10 mL) cooled to 0° C. under nitrogen was added a solution of Compound-2 (1.1 g, 6 mmol) in dry THF (10 mL). This solution was stirred for 30 min. A solution of Compound-12 (730 mg, 3.1 mmol) in dry THF (10 mL) was added at 0° C. and the resulting mixture was further stirred at room temperature for 3 h. The reaction was quenched with $NH_4Cl$ solution, and the mixture was extracted with ether twice. The combined organic layers were washed with brine, dried over anhydrous $Na_2SO_4$ and concentrated. The crude compound was purified by column chromatography on 60-120 mesh silica gel and eluted with 20% ethyl acetate/petroleum ether to obtain Compound-14 (530 mg, 66.4%). MS (m/z): [M+H]$^+$, 258.2.

Preparation of TEA-A-004: To a stirred solution of Compound-14 (530 mg, 2 mmol) in toluene (5.3 mL) cooled to −60° C. under nitrogen was added dropwise DIBAL-H (1.7 M in toluene, 4.24 mL) and the solution was stirred at room temperature for 2 h. Then reaction mass was cooled to −70° C., wet silica gel was added and the mixture was stirred for 1 h. The mixture was filtered and the filtrate was dried over anhydrous $Na_2SO_4$ and concentrated. The crude compound was purified by column chromatography on 60-120 mesh silica gel and eluted with 20% ethyl acetate/petroleum ether to obtain TEA-A-004 (230 mg, 44%). $^1$H NMR (CDCl$_3$, 400 MHz): δ 1.08 (s, 6H), 1.48 (t, J=12 Hz, 1H), 1.74 (s, 3H), 1.76-1.81 (m, 1H), 2.02-2.08 (m, 1H), 2.09 (s, 3H), 2.41 (dd, J=6 Hz, 17.2 Hz, 1H), 4.00 (m, 1H), 6.15-6.21 (m, 2H), 6.29 (d, J=12 Hz, 1H), 6.43 (d, J=15.6 Hz, 1H), 7.53 (dd, J=12 Hz, 14.8 Hz, 1H), 9.61 (d, J=8 Hz, 1H); $^{13}$C NMR (CDCl$_3$, 100 MHz): δ 13.36, 21.85, 28.94, 30.43, 37.31, 42.76, 48.51, 65.07, 128.1, 128.4, 131.2, 131.6, 137.37, 137.39, 146.5, 148.1, 194.0. IR: 3413, 1667 cm$^{-1}$. MS (m/z): [M+H]$^+$, 261.2.

PEA-A-003 (11-(4-Hydroxy-2,6,6-trimethyl-cyclohex-1-enyl)-5,9-dimethyl-undeca-2,4,6,8,10-pentaenal)

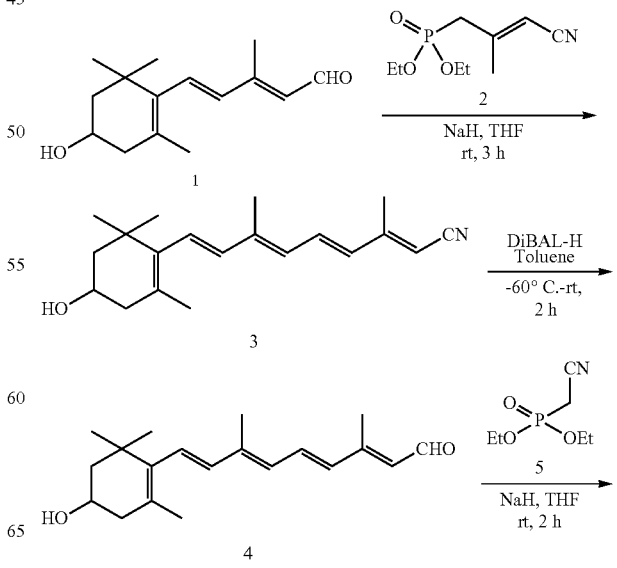

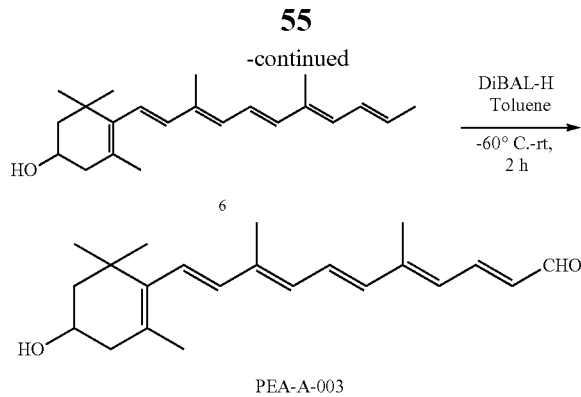

PEA-A-003

Preparation of Compound-3: To a stirred suspension of NaH (190 mg, 7.9 mmol) in dry THF (20 mL) cooled to 0° C. under nitrogen was added a solution of Compound-2 (1.68 g, 7.9 mmol) in dry THF (10 mL). The solution was stirred for 10 min and a solution of Compound-1 (530 mg, 2.2 mmol) in dry THF (10 mL) was added. The resulting solution was stirred at room temperature for 3 h, and then the reaction was quenched with an NH$_4$Cl solution. The mixture was extracted thrice with ether. The combined organic layers were washed with brine, dried over anhydrous Na$_2$SO$_4$ and concentrated. The crude compound was purified by column chromatography on 60-120 mesh silica gel and eluted with 20% ethyl acetate/petroleum ether to obtain Compound-3 (580 mg, 86.3%). MS (m/z): [M+H]$^+$, 298.4.

Preparation of Compound-4: To a stirred solution of Compound-3 (580 mg, 1.95 mmol) in toluene (6 mL) at −60° C. under nitrogen was added dropwise DIBAL-H (1.7 M in toluene, 4 mL) and the mixture was stirred at room temperature for 2 h. Then the solution was cooled to −20° C., and poured onto wet silica gel. The resulting mixture was stirred for 1 h, and filtrated. The filtrate was dried over anhydrous Na$_2$SO$_4$ and concentrated. The crude compound was purified by column chromatography on 60-120 mesh silica gel and eluted with 20% ethyl acetate/petroleum ether to obtain Compound-4 (250 mg, 42.6%). MS (m/z): [M+H]$^+$, 301.4.

Preparation of Compound-6: To a stirred suspension of NaH (40 mg, 1.66 mmol) in dry THF (8 mL) cooled to 0° C. under nitrogen was added a solution of Compound-5 (295 mg, 1.66 mmol) in dry THF (10 mL). The mixture was stirred for 30 min and cooled to 0° C. A solution of Compound-4 (250 mg, 0.83 mmol) in dry THF (10 mL) was added and the mixture was stirred at room temperature for 2 h. The reaction was quenched with NH$_4$Cl solution and the resulting mixture was extracted thrice with ethyl acetate. The combined organic layers were washed with brine, dried over anhydrous Na$_2$SO$_4$ and concentrated. The crude compound was purified by column chromatography on 60-120 mesh silica gel and eluted with 20% ethyl acetate/petroleum ether to obtain Compound-6 (200 mg, 74.5%). MS (m/z): [M+H]$^+$, 323.4.

Preparation of PEA-A-003: To a stirred solution of Compound-6 (200 mg, 0.6 mmol) in toluene (5 mL) at −60° C. under nitrogen was added DIBAL-H (1.7 M in toluene, 1.2 mL). The resulting solution was stirred at room temperature for 2 h, cooled to −20° C. and poured onto wet silica gel. This mixture was stirred for 1 h and filtered. The filtrate was dried over anhydrous Na$_2$SO$_4$ and concentrated. The crude compound was purified by column chromatography on 60-120 mesh silica gel and eluted with 20% ethyl acetate/petroleum ether to obtain PEA-A-003 (100 mg, 49.6%). $^1$H NMR (CDCl$_3$, 400 MHz): δ 1.07 (s, 6H), 1.48 (t, J=12 Hz, 1H), 1.74 (s, 3H), 1.76-1.80 (m, 1H), 2.00 (s, 3H), 2.01-2.09 (m, 1H), 2.11 (s, 3H), 2.39 (dd, J=6 Hz, 17 Hz, 1H), 4.00 (m, 1H), 6.12-6.16 (m, 4H), 6.35 (d, J=12.4 Hz, 1H), 6.39 (d, J=15.2 Hz, 1H), 6.91 (dd, J=11.4 Hz, 15 Hz, 1H), 7.51 (dd, J=12 Hz, 14.8 Hz, 1H), 9.61 (d, J=8 Hz, 1H); $^{13}$C NMR (CDCl$_3$, 100 MHz): δ 13.14, 13.51, 21.85, 28.95, 30.46, 37.33, 42.76, 48.58, 65.21, 127.1, 127.8, 128.9, 129.9, 130.6, 131.1, 136.1, 137.8, 138.3, 139.3, 146.8, 147.9, 193.8. MS (m/z): [M+H]$^+$, 327.3.

PEA-A-002 (11-(3-Hydroxy-2,6,6-trimethyl-cyclohex-1-enyl)-5,9-dimethyl-undeca-2,4,6,8,10-pentaenal)

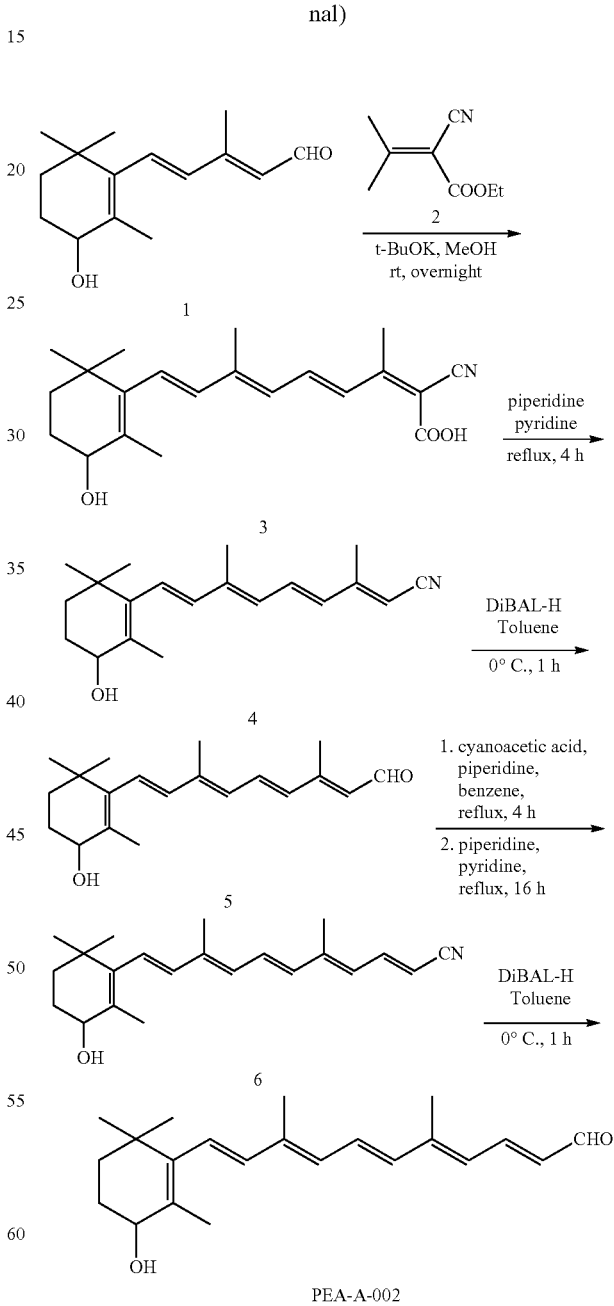

PEA-A-002

Preparation of Compound-3: To a stirred solution of t-BuOK (4.3 g, 38 mmol) in methanol (150 mL) at 0° C. was added a solution of Compound-2 (6.0 g, 25 mmol) in methanol (10 mL) followed by a solution of Compound-1 (7.8 g, 51 mmol) in methanol (10 mL). The solution was stirred at room temperature overnight and then evaporated. The residue was poured into water (100 mL) and the resulting aqueous layer was extracted twice with ether. Then the aqueous layer was acidified with diluted HCl and extracted thrice with ether. The combined ether organic layers were dried over anhydrous $Na_2SO_4$ and concentrated to obtain Compound-3 (6.0 g, 70%).

Preparation of Compound-4: A solution of Compound-3 (6.0 g, 17.5 mmol) in piperidine (120 mL) and pyridine (120 mL) was refluxed for 3 h, and then evaporated under vacuum. The residue was diluted with ethyl acetate and washed with a diluted HCl solution. The organic layer was dried over anhydrous $Na_2SO_4$ and concentrated. The crude compound was purified by column chromatography on 60-120 mesh silica gel and eluted with 10% ethyl acetate/petroleum ether to obtain Compound-4 (2.7 g, 51.7%). MS (m/z): $[M-OH]^+$, 280.4.

Preparation of Compound-5: To a stirred solution of Compound-4 (2.7 g, 9 mmol) in dry toluene (22 mL) at −5° C. under nitrogen was added dropwise DIBAL-H (1M in toluene, 13.6 mL) and the solution was stirred at 0° C. for another hour. The reaction was slowly quenched with a cold saturated sodium potassium tartrate solution, and the resulting mixture was filtered through celite. The filtrate was extracted with chloroform. The combined organic layers were dried over anhydrous $Na_2SO_4$ and concentrated. The crude compound was purified by column chromatography on 60-120 mesh silica gel and eluted with 10% acetone/petroleum ether to obtain Compound-5 (1.77 g, 65.5%). MS (m/z): $[M-OH]^+$, 283.4.

Preparation of Compound-6: To a stirred solution of Compound-5 (1.77 g, 5.9 mmol) in benzene (10.6 mL) cooled to 10° C. was added a solution of cyanoacetic acid (1.0 g, 11 mmol) followed by piperidine (1.4 mL, 11 mmol). The reaction mixture was relaxed for 4 h and evaporated under vacuum. The residue was dissolved in a solution of piperidine (25 mL) and pyridine (25 mL). The reaction mixture was refluxed for 16 h and then concentrated under vacuum. The residue was re-dissolved in ethyl acetate and washed with a diluted HCl solution. The aqueous layer was extracted twice with ethyl acetate. The combined organic layers were dried over anhydrous $Na_2SO_4$ and concentrated. The residue was purified by column chromatography on 60-120 mesh silica gel and eluted with 10% acetone/petroleum ether to obtain compound-6 (650 mg, 34.2%). MS (m/z): $[M-OH]^+$, 307.4.

Preparation of PEA-A-002: To a stirred solution of Compound-7 (650 mg, 2 mmol) in toluene (4 mL) at −5° C. under nitrogen was added DIBAL-H (1 M in toluene, 3 mL) dropwise. The reaction mixture was stirred at 0° C. for 1 h, and then the reaction was slowly quenched with a cold saturated sodium potassium tartrate solution. The resulting mixture was filtered through celite. The filtrate was extracted with chloroform. The combined organic layers were dried over anhydrous $Na_2SO_4$ and concentrated. The crude compound was column chromatography on 230-400 mesh silica gel and eluted with 5% acetone/petroleum ether to obtain PEA-A-002 (240 mg, 36.8%). $^1H$ NMR ($CDCl_3$, 400 MHz): δ 1.02 (s, 3H), 1.05 (s, 3H), 1.40-1.46 (m, 1H), 1.61-1.73 (m, 2H), 1.84 (s, 3H), 1.88-1.92 (m, 1H), 2.01 (d, J=0.8 Hz, 3H), 2.11 (d, J=0.8 Hz, 3H), 4.01 (t, J=4.6 Hz, 1H), 6.14-6.21 (m, 4H), 6.36 (d, J=13.6 Hz, 1H), 6.40 (d, J=15.2 Hz, 1H), 6.91 (dd, J=11.6 Hz, 14.8 Hz, 1H), 7.51 (dd, J=12 Hz, 14.8 Hz, 1H), 9.61 (d, J=8 Hz, 1H); $^{13}C$ NMR ($CDCl_3$, 100 MHz): δ 13.13, 13.52, 18.93, 27.74, 28.67, 29.31, 34.75, 35.04, 70.47, 127.9, 129.0, 129.8, 130.5, 131.0, 131.2, 136.3, 138.6, 139.1, 141.9, 146.7, 147.8, 193.8. MS (m/z): [M−OH], 309.

QEA-A-005 (9-(2,6,6-Trimethyl-cyclohex-1-enyl)-nona-2,4,6,8-tetraenal)

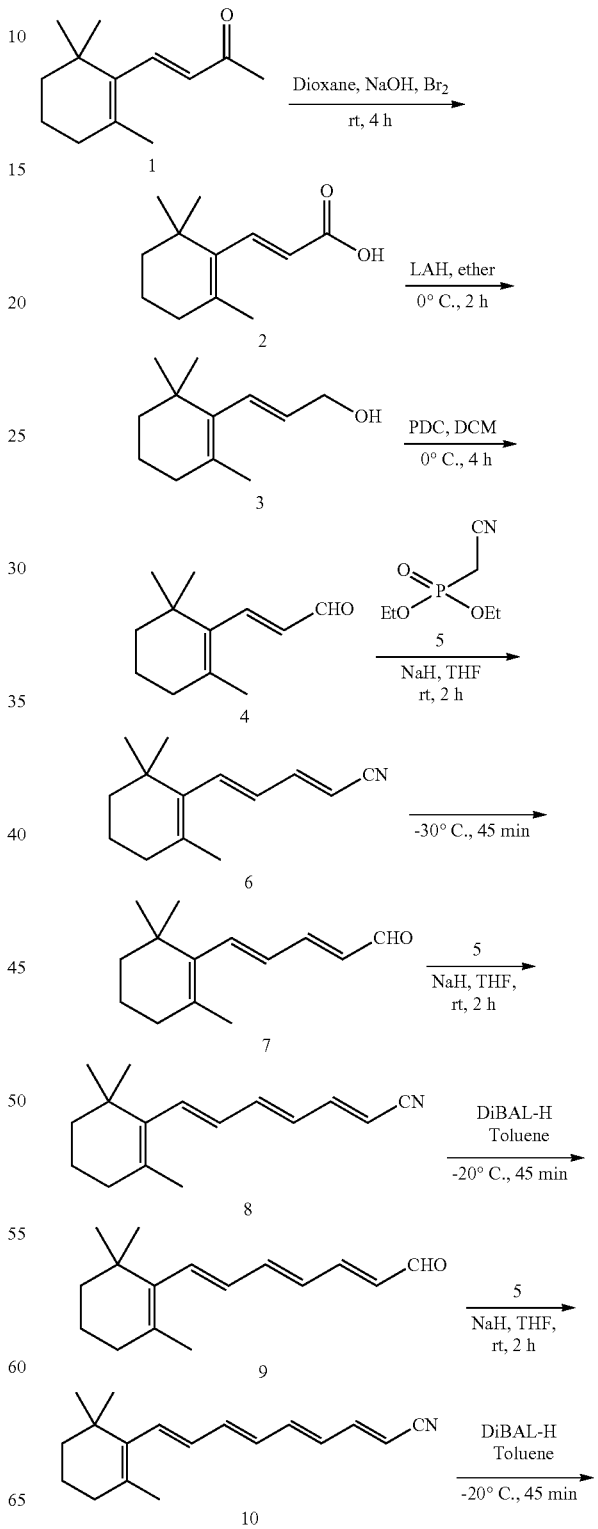

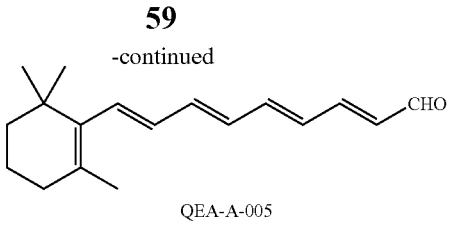

QEA-A-005

Preparation of Compound-2: To a stirred solution of NaOH (112 g, 2.8 mol) in water (480 mL) at 0° C. was added bromine (36.2 mL, 1.4 mol) and the reaction mixture was stirred for 2 h. Then a solution of Compound-1 (30 g, 156 mmol) in dioxane (60 mL) was slowly added. The mixture was stirred at room temperature for 4 h. The reaction was quenched with sodium sulphite solution and the resulting mixture was washed twice with ether. The aqueous layer was cooled to 0° C., acidified with diluted HCl and extracted thrice with ethyl acetate. The combined organic layers were washed with brine, dried over anhydrous $Na_2SO_4$ and concentrated to obtain Compound-2 (30 g, 99%). MS (m/z): $[M+H]^+$, 195.2.

Preparation of Compound-3: To a solution of LAH (8.2 g, 216 mmol) in anhydrous ether (168 mL) at 0° C. was added a solution of Compound-2 (21 g, 108 mmol) in anhydrous ether. The reaction mixture was stirred at 0° C. for 2 h. Then the reaction was quenched with a cold saturated $NH_4Cl$ solution and the resulting mixture was filtered through celite. The organic layer was separated from the filtrate, dried over anhydrous $Na_2SO_4$ and concentrated. The crude compound was purified by column chromatography on silica gel and eluted with 15-20% ethyl acetate/hexane to obtain Compound-3 (19 g, 97.5%). MS (m/z): $[M-OH]^+$, 163.3.

Preparation of Compound-4: To a stirred solution of Compound-3 (19 g, 105 mmol) in DCM (20 mL) at 0° C. was added PDC (119 g, 316 mmol) in portions. The reaction mixture was stirred at 0° C. for 4 h, diluted with ether and filtered through silica gel and concentrated. The crude compound was purified by column chromatography on 100-200 mesh silica gel and eluted with 4% ethyl acetate/hexane to obtain Compound-4 (10.7 g, 57.2%). MS (m/z): $[M+H]^+$, 179.3.

Preparation of Compound-6: To a stirred suspension of NaH (1.4 g, 58 mmol) in THF (10 mL) cooled to 0° C. was slowly added a solution of Compound-5 (10.3 g, 58 mmol) in dry THF (10 mL). The reaction mixture was stirred for 10 min, cooled to 0° C. and a solution of Compound-4 (6.9 g, 38 mmol) in THF (10 mL) was added. The reaction was continued at room temperature for 2 h, quenched with an $NH_4Cl$ solution and the resulting mixture was extracted thrice with ethyl acetate. The combined organic layers were washed with brine, dried over anhydrous $Na_2SO_4$ and concentrated. The crude compound was purified by column chromatography on silica gel and eluted with 5% ethyl acetate/hexane to obtain Compound-6 (4.5 g 57.8%). IR: 2212 $cm^{-1}$. MS (m/z): $[M+H]^+$, 202.3.

Preparation of Compound-7: To a stirred solution of Compound-6 (9 g, 44 mmol) in toluene (90 mL) at −30° C. was added dropwise DIBAL-H (1.7 M in toluene, 29 mL) under nitrogen. The reaction solution was stirred at −30° C. for 30 min, quenched with an ice cold sodium potassium tartrate solution and stirred at −30° C. for 45 min. The reaction mixture was filtered through celite, the precipitate was washed with ether and the aqueous layer from the filtrate was extracted twice with chloroform. The combined organic layers were dried over anhydrous $Na_2SO_4$ and concentrated. The crude compound was purified by column chromatography on 100-200 mesh silica gel and was eluted with 1% ethyl acetate/hexane to obtain Compound-7 (1.78 g, 19.5%). MS (m/z): $[M+H]^+$, 205.3.

Preparation of Compound-8: To a stirred suspension of NaH (312 mg, 13 mmol) in THF (10 mL) cooled to 0° C. was slowly added a solution of Compound-5 (2.3 g, 13 mmol) in dry THF (10 mL) and the reaction mixture was stirred for another 10 min. A solution of Compound-6 (1.78 g, 8.7 mmol) in THF (10 mL) was added and the solution was stirred at room temperature for 2 h. The reaction was quenched with $NH_4Cl$ solution and the resulting mixture was extracted thrice with ethyl acetate. The combined organic layers were washed with brine, dried over anhydrous $Na_2SO_4$ and concentrated. The crude compound was purified by column chromatography on 60-120 mesh silica gel and eluted with 1% ethyl acetate/hexane to obtain Compound-8 (1.39 g, 70%). MS (m/z): $[M+H]^+$, 228.3.

Preparation of Compound-9: To a stirred solution of Compound-8 (1.39 g, 6.1 mmol) in toluene (10 mL) at −20° C. under nitrogen was added dropwise DIBAL-H (1.7 M in toluene, 7.2 mL). The reaction mixture was stirred at −20° C. for 30 min. Then the reaction was quenched with an ice cold solution of sodium potassium tartrate. The resulting mixture was stirred at −20° C. for another 45 min, and filtered through celite. The precipitate was washed with ether and the aqueous layer of the filtrate was extracted twice with chloroform. The combined organic layers were dried over anhydrous $Na_2SO_4$ and concentrated. The crude compound was purified by column chromatography on 100-200 mesh silica gel and eluted with 2% ethyl acetate/hexane to obtain Compound-9 (490 mg, 35%). MS (m/z): $[M+H]^+$, 230.5.

Preparation of Compound-10: To a stirred suspension of NaH (76 mg, 3.19 mmol) in THF (5.6 mL) cooled to 0° C. was slowly added a solution of Compound-5 (566 mg, 3.19 mmol) in dry THF (10 mL). The reaction mixture was stirred for 10 min, cooled to 0° C. A solution of Compound-9 (490 mg, 2.13 mmol) in THF (10 mL) was added, and the solution was stirred at room temperature for 2 h. The reaction was quenched with $NH_4Cl$ solution and the resulting mixture was extracted thrice with ethyl acetate. The combined organic layers were washed with brine, dried over anhydrous $Na_2SO_4$ and concentrated. The crude compound was purified by silica gel column chromatography and eluted with 1% ethyl acetate/hexane to obtain Compound-10 (450 mg, 83.4%). MS (m/z): $[M+H]^+$, 254.4.

Preparation of QEA-A-005: To a stirred solution of Compound-10 (450 mg, 1.77 mmol) in toluene (4.5 mL) at −20° C. under nitrogen was added dropwise DIBAL-H (1.7 M in toluene, 2 mL). The mixture was stirred at −20° C. for 30 min. Then the reaction was quenched with an ice cold solution of sodium potassium tartrate and the resulting solution was stirred at −20° C. for another 45 min. The mixture was filtered through celite. The precipitate was washed with ether and the aqueous layer of filtrate was extracted twice with chloroform. The combined organic layers were dried over anhydrous $Na_2SO_4$ and concentrated. The crude compound was purified by column chromatography on 100-200 mesh silica gel and eluted with 1% ethyl acetate/hexane to obtain QEA-A-005 (80 mg, 17.6%). $^1H$ NMR ($CDCl_3$, 300 MHz): δ 1.04 (s, 6H), 1.45 (m, 2H), 1.61 (m, 2H), 1.74 (s, 3H), 2.04 (t, J=6.6 Hz, 2H), 6.14 (dd, J=8 Hz, 15.2 Hz, 1H), 6.20 (dd, J=10.8 Hz, 15.2 Hz, 1H), 6.30 (dd, J=11.2 Hz, 14.8 Hz, 1H), 6.38 (d, dd, J=16 Hz, 1H), 6.43 (dd, J=11.2 Hz, 14.8 Hz, 1H), 6.55 (dd, J=11 Hz, 15 Hz, 1H), 6.73 (dd, J=11 Hz, 14.8 Hz, 1H), 7.15 (dd, J=11.2 Hz, 15.2 Hz, 1H), 9.55 (d, J=8 Hz, 1H); $^{13}C$ NMR ($CDCl_3$, 100

MHz): δ 19.31, 22.05, 29.15, 33.65, 34.39, 39.96, 129.18, 129.92, 130.68, 132.55, 132.76, 137.54, 140.45, 152.46, 193.8. MS (m/z): [M+H]⁺, 257.3.

QEA-A-004 (7-Methyl-9-(2,6,6-trimethyl-cyclohex-1-enyl)-nona-2,4,6,8-tetraenal)

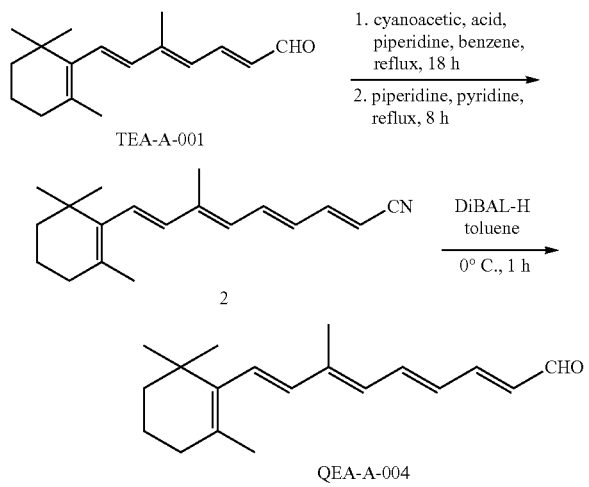

Preparation of Compound-2: To a stirred solution of TEA-A-001 (2.0 g, 8.1 mmol) in benzene (12 mL) at 0° C. was added a solution of cyanoacetic acid (1.4 g, 16.3 mmol) followed by piperidine (1.61 mL, 16.3 mmol). The reaction mixture was stirred for 18 h and then evaporated. A solution of piperidine (25 mL) and pyridine (25 mL) was added. The resulting solution was refluxed for 8 h, and then evaporated under vacuum. The residue was poured into ethyl acetate and washed thrice with a dilute HCl solution. The organic layer was dried over anhydrous $Na_2SO_4$ and concentrated. The crude compound was purified by column chromatography on 60-120 mesh silica gel and eluted with 40% DCM/petroleum ether to obtain Compound-2 (900 mg, 41.5%). MS (m/z): [M+H]⁺, 268.4.

Preparation of QEA-A-004: To a solution of Compound-2 (900 mg, 3.37 mmol) in dry toluene (4.5 mL) at −5° C. under nitrogen was slowly added DIBAL-H (1 M in toluene, 3.37 mL). The solution was stirred at 0° C. for 1 h, and then the reaction was quenched with 1 M $H_2SO_4$ solution. The resulting mixture was extracted thrice with ether. The combined organic layers were dried over anhydrous $Na_2SO_4$ and concentrated. The residue was purified by column chromatography on 60-120 mesh silica gel and eluted with 30% DCM/petroleum ether to obtain QEA-A-004 (180 mg, 18%). ¹H NMR (CDCl₃, 400 MHz): δ 1.03 (s, 9H), 1.45-1.49 (m, 2H), 1.58-1.65 (m, 2H), 1.72 (s, 3H), 2.02 (s, 3H), 2.03 (m, 2H), 6.11-6.19 (m, 3H), 6.35-6.49 (m, 2H), 7.07 (dd, J=14.4 Hz, 12 Hz, 1H), 7.21 (dd, J=15 Hz, 11 Hz, 1H), 9.56 (dd, J=8 Hz, 0.8 Hz, 1H); ¹³C NMR (CDCl₃, 100 MHz): δ 13.17, 19.38, 20.01, 29.19, 29.93, 33.39, 34.49, 39.79, 129.2, 129.6, 130.5, 130.7, 131.0, 137.1, 137.8, 139.5, 142.8, 152.7, 193.8. MS (m/z): [M+H]⁺, 271.4.

PEA-A-001 (5,9-Dimethyl-11-(2,6,6-trimethyl-cyclohex-1-enyl)-undeca-2,4,6,8,10-pentaenal)

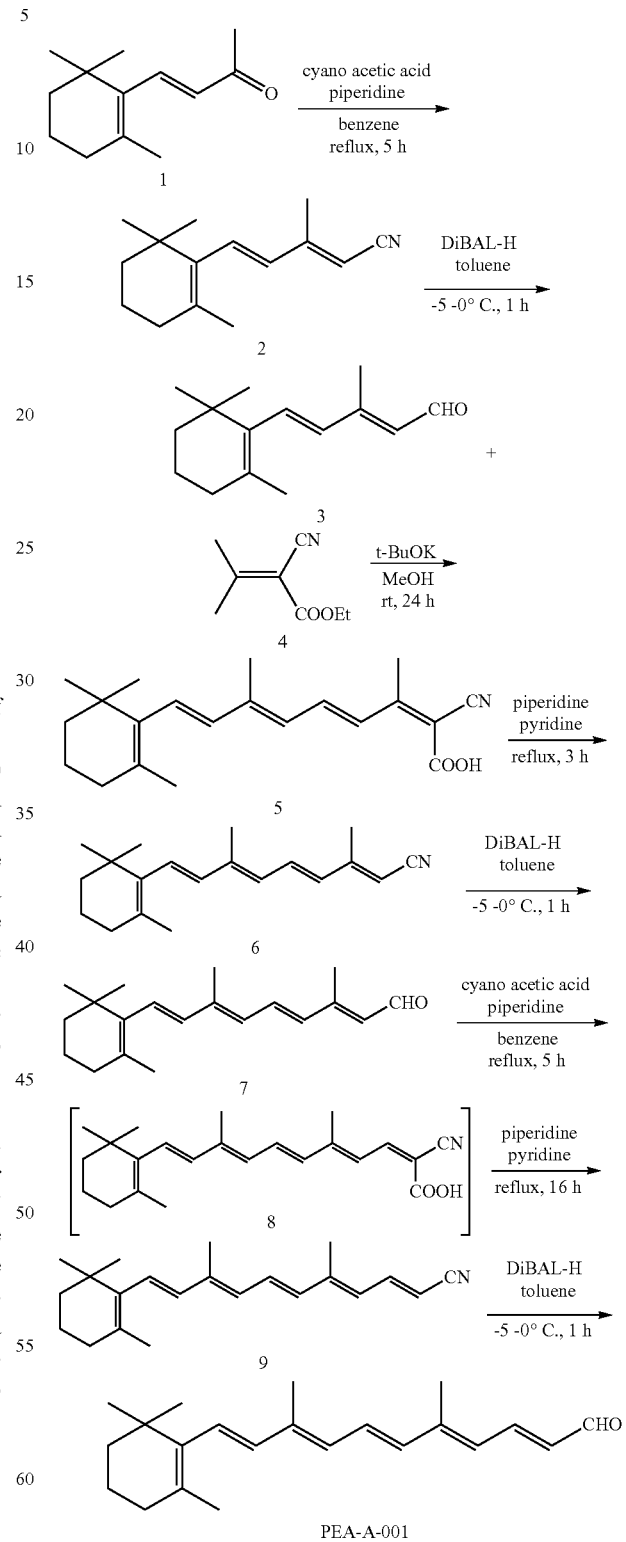

Preparation of Compound-2: To a stirred solution of Compound-1 (20 g, 104 mmol) in benzene (120 mL) at 0° C. was added a solution of cyanoacetic acid (17.6 g, 208 mmol) in benzene (5 mL) followed by piperidine (20.4 mL). The reaction mixture was refluxed for 18 h, cooled to room temperature and diluted with water (200 mL). The aqueous layer was extracted with ethyl acetate (3×200 mL). The combined organic layers were dried over anhydrous $Na_2SO_4$ and concentrated. The residue was purified by column chromatography on 60-120 mesh silica gel and eluted with 0.5% ethyl acetate/petroleum ether to obtain compound-2 (19.3 g, 86%). MS (m/z): [M+H]$^+$, 216.3.

Preparation of Compound-3: To a stirred solution of Compound-2 (19.3 g, 89.6 mol) in dry toluene (96 mL) at −5° C. was slowly added DIBAL-H (1 M in toluene, 89.6 mL) and the reaction mixture was stirred at 0° C. for 1 h. The reaction was quenched with chilled 1 M $H_2SO_4$ and the resulting mixture was extracted thrice with ether. The combined organic layers were dried over anhydrous $Na_2SO_4$ and concentrated. The residue was purified by column chromatography on 60-120 mesh silica gel and eluted with 0.5% ethyl acetate/petroleum ether to obtain compound-3 (15.6 g, 79.7%). MS (m/z): [M+H]$^+$, 219.3.

Preparation of Compound-5: To a stirred solution of t-BuOK (4.63 g, 41.25 mmol) in methanol (100 mL) at 0° C. was added a solution of Compound-3 (6.0 g, 27.5 mmol) and Compound-4 (8.425 g, 55 mmol). The solution was stirred at room temperature for 2 h and evaporated under vacuum. The residue was poured into water and extracted thrice with ether. The aqueous layer was acidified with a diluted HCl solution and extracted thrice with ether. The combined organic layers were washed with brine, dried over anhydrous $Na_2SO_4$ and concentrated to obtain Compound-5 (21.6 g). The crude material was used for the next step without further purification.

Preparation of Compound-6: To a stirred solution of crude Compound-5 (21.6 g, 66 mmol) was added dropwise piperidine (20 mL) followed by pyridine (20 mL). The reaction mixture was refluxed for 3 h, and evaporated under vacuum. The residue was poured into ethyl acetate and washed thrice with a diluted HCl solution. The resulting mixture was washed with brine, dried over anhydrous $Na_2SO_4$ and concentrated. The crude compound was purified by column chromatography on 100-200 mesh silica gel with 10% ethyl acetate/petroleum ether as to obtain Compound-6 (4.9 g, 63% for two steps). MS (m/z): [M+H]$^+$, 282.4.

Preparation of Compound-7: To a stirred solution of Compound-6 (8.7 g, 30 mmol) in dry toluene (43.5 mL) at −5° C. under nitrogen was added dropwise DIBAL-H (1 M in toluene, 31 mL). The reaction mixture was stirred at 0° C. for 1 h. the reaction was slowly quenched with potassium sodium tartrate solution and the resulting mixture was filtered through celite. The filtrate was extracted with chloroform thrice. The combined organic layers were dried over anhydrous $Na_2SO_4$ and concentrated. The crude compound was purified by column chromatography on 230-400 mesh silica gel and eluted with 10% DCM/petroleum ether to obtain Compound-7 (2.3 g, 26.2%). MS (m/z): [M+H]$^+$, 285.4.

Preparation of Compound-9: To a stirred solution of Compound-7 (2.1 g, 7.38 mmol) in benzene (12.6 mL) cooled to at 0° C. was added a solution of cyanoacetic acid (1.2 g, 14.7 mmol) followed by piperidine (1.4 mL). The reaction mixture was stirred for 5 h and then evaporated. A solution of piperidine (25 mL) and pyridine (25 mL) was added to the residue. The resulting mixture was refluxed for 16 h and then evaporated under vacuum. The residue was washed thrice with diluted 1 M HCl solution and then brine, dried over anhydrous $Na_2SO_4$ and concentrated under vacuum. The crude compound was purified by column chromatography on 100-200 mesh silica gel and eluted with 20% of DCM/petroleum ether to obtain Compound-9 (600 mg, 26.4%). MS (m/z): [M+H]$^+$, 308.4.

Preparation PEA-A-001: To a stirred solution of Compound-9 (600 mg, 1.95 mmol) in dry toluene (3 mL) at −5° C. under nitrogen was added dropwise DIBAL-H (1 M in toluene, 1.95 mL). The reaction mixture was stirred at 0° C. for 1 h. The reaction was slowly quenched with potassium sodium tartrate solution and the resulting mixture was filtered through celite. The filtrate was extracted with chloroform. The combined organic layers were dried over anhydrous $Na_2SO_4$ and concentrated. The crude compound was purified by column chromatography on 230-400 mesh silica gel and eluted with 1% ethyl acetate/petroleum ether to obtain PEA-A-001 (75 mg, 12.4%). $^1$H NMR (CDCl$_3$, 400 MHz): δ 1.03 (s, 6H), 1.46 (m, 2H), 1.59-1.63 (m, 2H), 1.72 (d, J=0.8 Hz, 3H), 2.01 (d, J=0.8 Hz, 3H), 2.02 (m, 2H), 2.11 (d, J=0.8 Hz, 3H), 6.13-6.40 (m, 6H), 6.92 (dd, J=15.2 Hz, 11.6 Hz, 1H), 7.51 (dd, J=14.8 Hz, 12 Hz, 1H), 6.92 (dd, J=15.2 Hz, 11.6 Hz, 1H), 9.61 (d, J=8 Hz, 1H); $^{13}$C NMR (CDCl$_3$, 100 MHz): δ 13.16, 13.52, 19.43, 22.01, 29.2, 33.36, 34.49, 39.81, 128.71, 128.92, 130.12, 130.19, 130.37, 130.95, 135.72, 137.54, 137.93, 139.7, 146.94, 147.97, 193.87. MS (m/z): [M+H]$^+$, 311.4.

QEA-B-004 (3,7-Di-tert-butyl-9-(2,6,6-trimethyl-cyclohex-1-enyl)-nona-2,4,6,8-tetraenal)

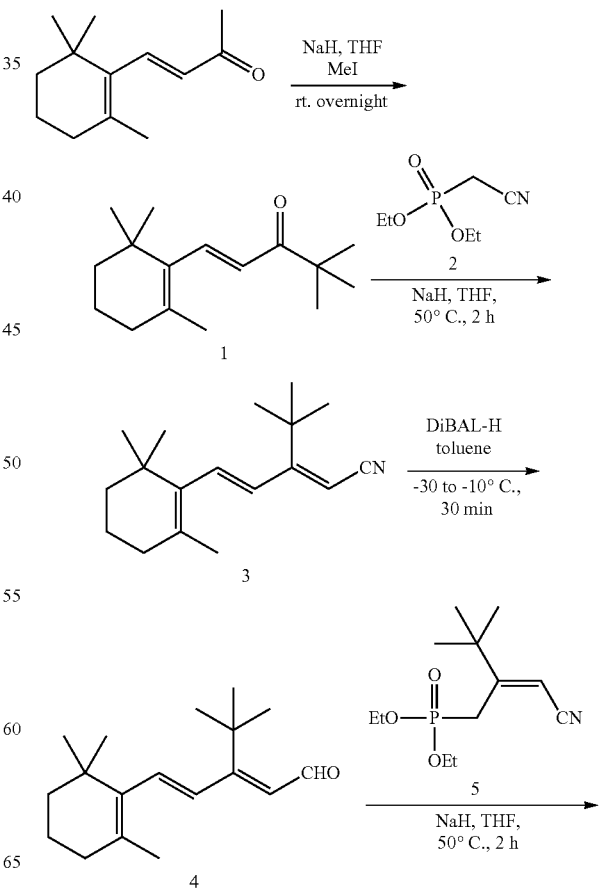

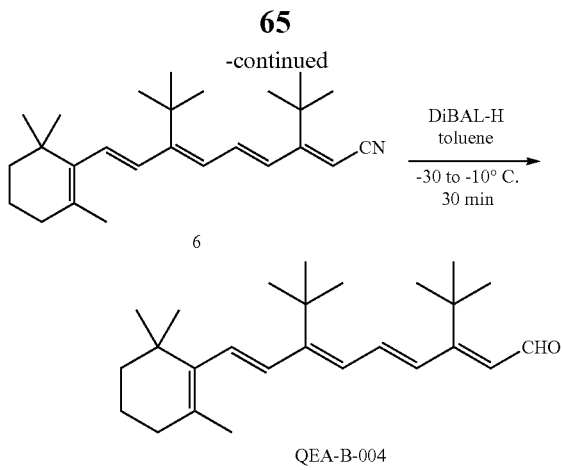

Preparation of Compound-1: To a suspension of NaH (5 g, 0.2 mol) in dry THF (10 mL) at 0° C. was added dropwise a solution of β-ionone (10 g, 52 mmol) in dry THF (10 mL). The reaction mixture was stirred at 0° C. for 1 h. Then a solution of methyl iodide (12.5 mL, 0.2 mol) in dry THF (5 mL) was slowly added and the resulting solution was stirred at room temperature overnight. The reaction was quenched with $NH_4Cl$ solution and the mixture was extracted with ethyl acetate (3×200 mL). The combined organic layers were dried over anhydrous $Na_2SO_4$ and concentrated. The crude compound was purified by column chromatography on 100-200 mesh silica gel and eluted with 0.5% ethyl acetate/petroleum ether to obtain Compound-1 (5 g, 41%). MS (m/z): $[M+H]^+$, 235.3

Preparation of Compound-3: To a stirred suspension of NaH (1.54 g, 64 mmol) in dry THF (20 mL) at 0° C. was added dropwise a solution of Compound-2 (11.4 g, 64 mmol) in dry THF (10 mL). The reaction mixture was stirred at 0° C. for 10 min. Then a solution of Compound-1 (5 g, 21 mmol) in dry THF (10 mL) was slowly added and the solution was stirred at 50° C. for 2 h and at room temperature for 12 h. The reaction was quenched with $NH_4Cl$ solution and the resulting mixture was extracted with ethyl acetate (3×200 mL). The combined organic layers were dried over anhydrous $Na_2SO_4$ and concentrated. The crude compound was purified by column chromatography on 60-120 mesh silica gel 1 and eluted with 0.5% ethyl acetate/petroleum ether to obtain Compound-3 (5 g, 91%). MS (m/z): $[M+H]^+$, 258.4.

Preparation of Compound-4: To a stirred solution of compound-3 (5.3 g, 20.6 mmol) in dry toluene (53 mL) at −30° C. under nitrogen was added dropwise DIBAL-H (1.7 M in toluene, 24 mL). The solution was cooled to −10° C., poured onto wet silica gel and stirred for 30 min. The mixture was filtered through silica gel. The precipitate was washed twice with ether and the filtrate was concentrated. The residue was purified by column chromatography on 60-120 mesh silica gel and eluted with 0.8% ethyl acetate/petroleum ether to obtain Compound-4 (1.53 g, 28.5%). MS (m/z): $[M+H]^+$, 261.4.

Preparation of Compound-6: To a stirred suspension of NaH (69 mg, 2.88 mmol) in dry THF (20 mL) at 0° C. was added dropwise a solution of Compound-5 (747 mg, 2.88 mmol) in dry THF (10 mL). The reaction mixture was stirred for 1 h. Then a solution of Compound-4 (300 mg, 1.15 mmol) in dry THF (10 mL) was slowly added at 0° C. The resulting solution was stirred for 3 h, the reaction was quenched with $NH_4Cl$ solution and the mixture was extracted with ethyl acetate. The combined organic layers were dried over anhydrous $Na_2SO_4$ and concentrated. The crude compound was purified by column chromatography on 60-120 mesh silica gel and eluted with 0.5% ethyl acetate/petroleum ether to obtain Compound-6 (320 mg, 76%). IR: 2208 $cm^{-1}$. MS (m/z): $[M+H]^+$, 366.6.

Preparation of QEA-B-004: To a stirred solution of Compound-6 (320 mg, 0.87 mmol) in dry toluene (10 mL) at −30° C. under nitrogen was added dropwise DIBAL-H (1.7 M in toluene, 2.1 mL). The solution was cooled to −10° C., poured onto wet silica gel and stirred for 30 min. The mixture was filtered, the precipitate was washed twice with ether and the filtrate was concentrated. The residue was purified by column chromatography on 60-120 mesh silica gel and eluted with 1% ethyl acetate/petroleum ether to obtain QEA-B-004 (85 mg, 26.4%). $^1H$ NMR ($CDCl_3$, 300 MHz): δ 1.14 (s, 9H), 1.15 (s, 9H), 1.42-1.46 (m, 2H), 1.58-1.61 (m, 2H), 1.70 (d, J=0.4 Hz, 3H), 1.99 (t, J=6.4 Hz, 2H), 5.89-6.02 (m, 3H), 6.18 (d, J=10.8 Hz, 1H), 6.31 (d, J=14.8 Hz, 1H), 6.80 (dd, J=14.8 Hz, 10.8 Hz, 1H), 9.65 (d, J=7.6 Hz, 1H); $^{13}C$ NMR ($CDCl_3$, 100 MHz): δ 19.42, 22.08, 29.06, 29.47, 29.88, 33.05, 34.25, 36.51, 37.21, 39.60, 121.77, 125.25, 125.8, 129.7, 129.8, 134.9, 137.9, 140.0, 155.8, 173.1, 194.0. MS (m/z): $[M+H]^+$, 369.6.

QEA-B-003 (7-tert-Butyl-3-methyl-9-(2,6,6-trimethyl-cyclohex-1-enyl)-nona-2,4,6,8-tetraenal)

Preparation of Compound-3: To a stirred suspension of NaH (276 mg, 11 mmol) in dry THF (2 mL) at 0° C. was added dropwise a solution of Compound-2 (2.5 g, 11 mmol) in dry THF (10 mL). The reaction mixture was stirred at room temperature for 40 min. Then a solution of Compound-1 (1.2 g, 4.6 mmol) in dry THF (10 mL) was slowly added at 0° C. and the resulting mixture was stirred for 1 h. The reaction was quenched with $NH_4Cl$ solution and the product was extracted with ethyl acetate (3×200 mL). The combined organic layers were dried over anhydrous $Na_2SO_4$ and concentrated. The crude compound was purified by column chromatography on 60-120 mesh silica gel and eluted with 2% ethyl acetate/petroleum ether to obtain Compound-3 (1.4 g, 94%). MS (m/z): [M+H]+, 324.4.

Preparation of QEA-B-003: To a stirred solution of Compound-3 (1.4 g, 4.3 mmol) in dry toluene (10 mL) at −30° C. under nitrogen was added dropwise DIBAL-H (1.7 M in toluene, 5 mL). The solution was cooled to −10° C., poured onto wet silica gel and stirred for 30 min. The mixture was filtered, the precipitate was washed twice with ether and the combined filtrate was concentrated. The residue was purified by column chromatography on 100-200 mesh silica gel and eluted with 2% ethyl acetate/petroleum ether to obtain QEA-B-003 (840 mg, 59.9%). 1H NMR (CDCl3, 300 MHz): δ 1.05 (s, 6H), 1.15 (s, 9H), 1.4-1.5 (m, 2H), 1.6-1.7 (m, 2H), 1.8 (s, 3H), 2.0-2.1 (m, 2H), 2.2-2.3 (s, 3H), 5.9-6.0 (m, 1H), 6.0-6.1 (m, 2H), 6.2-6.3 (d, 1H), 6.4-6.45 (d, 1H), 7.3-7.4 (m, 1H), 10.1 (d, 1H). MS (m/z): [M+H]+, 327.3.

QEA-F-001 (3,7-Dimethyl-9-(2,2,6-trimethyl-cyclohexyl)-nona-2,4,6,8-tetraenal)

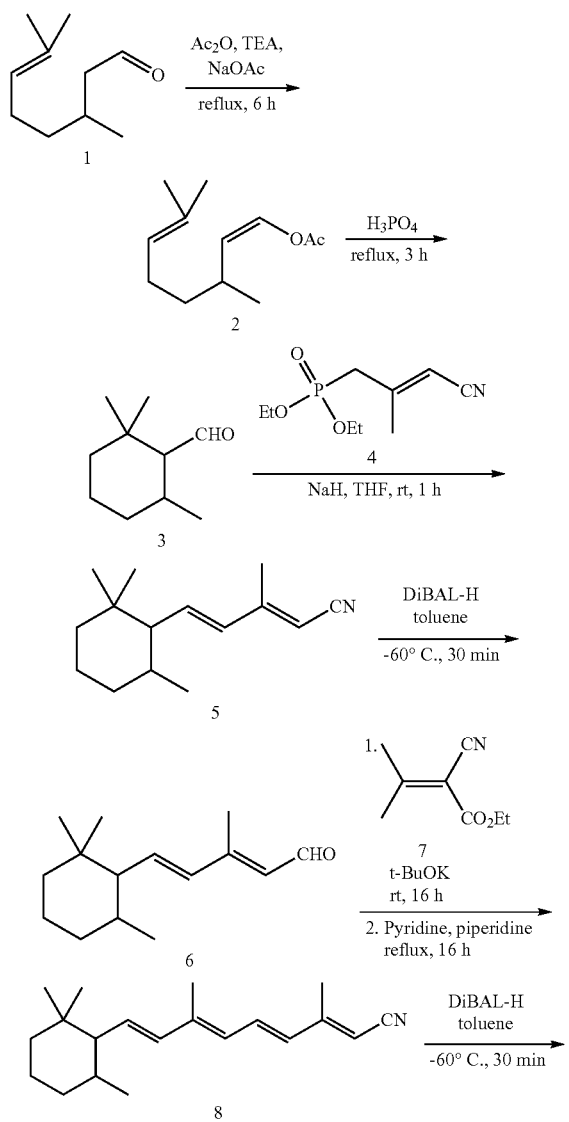

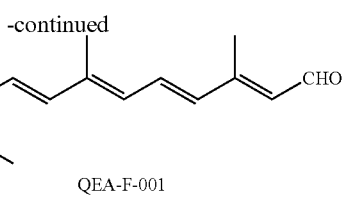

QEA-F-001

Preparation of Compound-2: To Ac2O (148 mL, 1.45 mol) cooled to 0° C. under nitrogen was added NaOAc (4.6 g, 5.5 mmol) followed by TEA (168 mL, 1.2 mol). The solution was heated to 75° C. Then Compound-1 (172 g, 1.11 mol) was added dropwise and the solution was refluxed for 6 h. The reaction was quenched with water (100 mL), and the resulting mixture was extracted with toluene twice. The combined toluene solution was used in the next step without further purification.

Preparation of Compound-3: To a stirred solution of the above Compound-2 in toluene (89 mL) was added dropwise a solution of 85% H3PO4 (110 g). The solution was refluxed for 3 h, cooled to 5° C. and poured into cold water. The organic layer was washed with a NaHCO3 solution, dried over anhydrous Na2SO4 and concentrated. The crude compound was purified by column chromatography on 100-200 mesh silica gel and eluted with 5% of ethyl acetate/petroleum ether to obtain Compound-3 (6.5 g, 3.7%). MS (m/z): [M+H]+, 155.2.

Preparation of Compound-5: To a stirred suspension of NaH (2.025 g, 84 mmol) in THF (190 mL) at 0° C. was slowly added a solution of Compound-4 (18.3 g, 84 mmol). The solution was stirred for 45 min and then cooled to 0° C. A solution of Compound-3 (6.5 g, 42 mmol) in THF (10 mL) was added, and the solution was stirred at room temperature for 1 h. the reaction was quenched with an NH4Cl solution. The resulting mixture was extracted with ethyl acetate (3×100 mL). The combined organic layers were dried over anhydrous Na2SO4 and concentrated. The crude compound was purified by column chromatography on 60-120 mesh silica gel and eluted with 5% ethyl acetate/petroleum ether to obtain Compound-5 (6.1 g, 66.7%). MS (m/z): [M+H]+, 218.2.

Preparation of Compound-6: To a stirred solution of Compound-5 (6 g, 27.6 mmol) in dry toluene (60 mL) cooled to −60° C. under nitrogen was added dropwise DIBAL-H (1.7 M in toluene, 32.5 mL). The reaction mixture was stirred at −60° C. for 30 min, then warmed to −30° C. and poured onto wet silica gel, stirred for 1 h and filtered. The precipitate was washed twice with ether and the filtrate was concentrated. The crude compound was purified by column chromatography on 60-120 mesh silica gel and eluted with 1% of ethyl acetate/petroleum ether as to obtain Compound-6 (1.55 g, 25%). MS (m/z): [M+H]+, 221.2.

Preparation of Compound-8: To a stirred solution of t-BuOK (1 g, 9 mmol) at 0° C. was added methanol (25 mL) followed by a solution of Compound-6 (0.8 g, 3.6 mmol) in methanol (10 mL). Then a solution of Compound-7 (1.1 g, 7.2 mmol) in methanol (10 mL) was added under nitrogen. The reaction solution was stirred at room temperature for 16 h and then evaporated. The residue was dissolved in a solution of pyridine (32 mL) and piperidine (32 mL). The mixture was refluxed for 16 h and then evaporated. Then diluted HCl was added to the residue and the resulting mixture was extracted twice with ethyl acetate. The combined organic layers were washed with brine, dried over anhydrous Na2SO4 and concentrated. The crude compound was purified by column chromatography on 100-200 mesh silica gel and eluted with 0.5% ethyl acetate/hexane to obtain Compound-8 (380 mg, 38%). MS (m/z): [M+H]+, 284.4.

Preparation of QEA-F-001: To a stirred solution of Compound-8 (380 mg, 1.3 mmol) in dry toluene (1.9 mL) cooled to −20° C. under nitrogen was added dropwise DIBAL-H (1 M in toluene, 1.4 mL). The reaction mixture was stirred at −20° C. for 30 min, poured into an ice cold solution of sodium potassium tartrate and stirred at 0° C. for 1 h. The resulting mixture was filtered through celite and the filtrate was extracted twice with chloroform. The combined organic layers were dried over anhydrous Na$_2$SO$_4$ and concentrated. The crude compound was purified by column chromatography on 100-200 mesh silica gel and eluted with 0.5% ethyl acetate/hexane to obtain QEA-F-001 (80 mg, 20.8%). $^1$H NMR (CDCl$_3$, 300 MHz): δ 0.9 (s, 9H), 1.35-1.45 (m, 3H), 1.55-1.65 (m, 4H), 2.1 (m, 3H), 2.2 (m, 1H), 2.3 (s, 3H), 5.9-6.0 (m, 2H), 6.2-6.3 (m, 2H), 6.3-6.4 (m, 1H), 6.6-6.7 (m, 1H), 10.1 (d, 1H). MS (m/z): [M+H]+, 287.4.

QEA-A-006 (9-Cyclohex-1-enyl-3,7-dimethyl-nona-2,4,6,8-tetraenal)

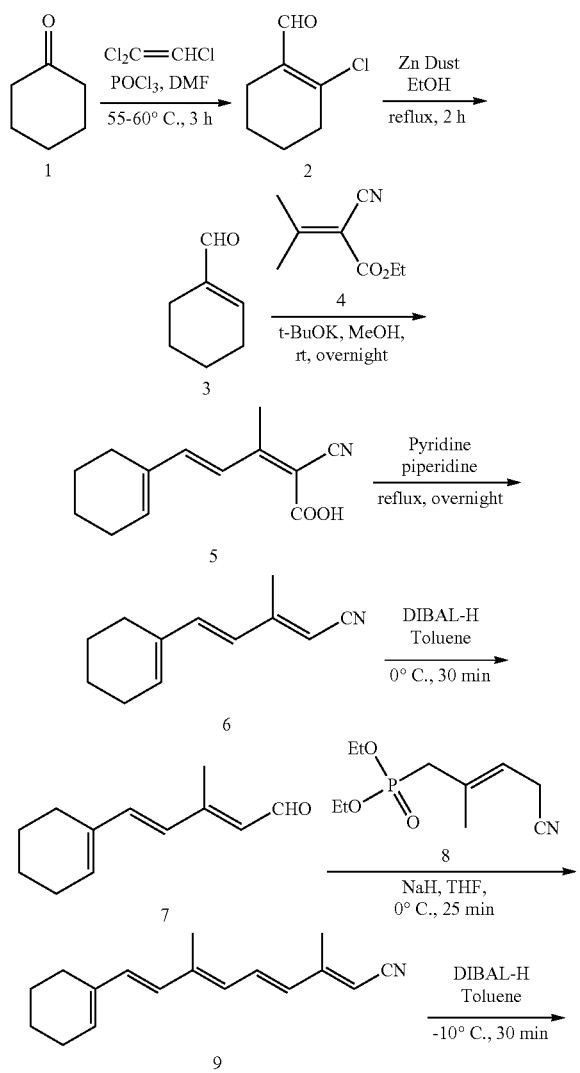

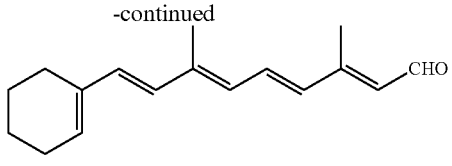

QEA-A-006

Preparation of Compound-2: To a stirred solution of trichloroethylene (5 mL) and DMF (101.5 mL, 1.314 mol) at 0° C. was added dropwise POCl$_3$ and the solution was stirred at room temperature for 30 min. Then a solution of Compound-1 (100 g, 1.01 mol) in trichloroethylene (5 mL) was added. The solution was stirred at 55-60° C. for 3 h. A solution of sodium acetate (375 g, 4.57 mol) in water (800 mL) was added to the mixture at 35° C. The resulting organic layer was dried on anhydrous Na$_2$SO$_4$ and concentrated. The crude compound (122 g, 844 mmol) was taken to the next step without further purification. Preparation of Compound-3: To a stirred solution of Compound-2 (122 g, 844 mmol) in ethanol (9.6 mL) at room temperature was added Zn dust (496 g, 7.59 mol). The reaction mixture was refluxed for 2 h, and then cooled to room temperature. The mixture was filtered and the filtrate was concentrated. The residue was dissolved in water and ethyl acetate, then filtered through celite. The organic layer of filtrate was washed with water, dried over anhydrous Na$_2$SO$_4$ and concentrated. The crude compound was purified by fractional distillation to obtain Compound-3 (17 g, 15%). MS (m/z): [M+H]+, 111.2.

Preparation of Compound-5: To a stirred solution of t-BuOK (30.55 g, 272 mmol) in methanol (10 mL) under nitrogen at 0° C. was added a solution of Compound-3 (12 g, 108 mmol) in methanol (10 mL) followed by Compound-4 (33.36 g, 210 mmol) in methanol (10 mL). The reaction mixture was stirred at room temperature overnight, and then evaporated. The residue was poured into diluted HCl and extracted twice with ethyl acetate. The combined organic layers were washed with brine, dried over anhydrous Na$_2$SO$_4$ and concentrated to obtain Compound-5 (40 g). The crude material was used for the next step without further purification.

Preparation of Compound-6: A solution of crude Compound-5 (40 g) in piperidine (20 mL) and pyridine (20 mL) was refluxed overnight. Then the solution was evaporated under vacuum. The residue was poured into diluted HCl and extracted with ethyl acetate. The organic layer was washed with brine, dried over anhydrous Na$_2$SO$_4$ and concentrated. The crude compound was purified by column chromatography on 100-200 mesh silica gel and eluted with 1% ethyl acetate/hexane to obtain Compound-6 (4.71 g, 25% in 2 steps). MS (m/z): [M+H]+, 174.2.

Preparation of Compound-7: To a stirred solution of Compound-6 (3.6 g, 20 mmol) in dry toluene (5 mL) at −10° C. was slowly added DIBAL-H (1 M in toluene, 23 mL) and the reaction mixture was stirred at 0° C. for 30 min. Then the mixture was poured into an ice cold solution of sodium potassium tartrate and stirred at 0° C. for 1 h and filtered through celite. The filtrate was extracted twice with chloroform. The combined organic layer was dried over anhydrous Na$_2$SO$_4$ and concentrated. The residue was purified by column chromatography on 100-200 mesh silica gel and eluted with 2% ethyl acetate/hexane to obtain Compound-7 (750 mg, 20%). MS (m/z): [M+H]+, 177.1.

Preparation of Compound-9: To a stirred suspension of NaH (395 mg, 16 mmol) in dry THF (20 mL) at 0° C. was added dropwise a solution of Compound-8 (3.8 g, 16 mmol) in dry THF (10 mL). A solution of Compound-7 (950 mg, 5 mmol) in dry THF (10 mL) was slowly added at 0° C. The reaction solution was stirred at room temperature for 3 h. The reaction was quenched with an NH₄Cl solution and the resulting mixture was extracted twice with ethyl acetate. The combined organic layers were washed with brine, dried over anhydrous Na₂SO₄ and concentrated. The crude compound was purified by column chromatography on 100-200 mesh silica gel and eluted with 2% ethyl acetate/hexane to obtain Compound-9 (750 mg, 58.1%). MS (m/z): [M+H]$^+$, 240.3.

Preparation of QEA-A-006: To a stirred solution of Compound-9 (0.83 g, 3 mmol) in dry toluene (5 mL) at −10° C. was slowly added DIBAL-H (1 M in toluene, 3.8 mL). The reaction mixture was stirred at −10° C. for 30 min, poured into an ice cold solution of sodium potassium tartrate. The resulting mixture was stirred at 0° C. for 1 h, and filtered through celite. The filtrate was extracted twice with chloroform. The combined organic layers were dried over anhydrous Na₂SO₄ and concentrated. The residue was purified by column chromatography on 100-200 mesh silica gel and eluted with 1% ethyl acetate/hexane to obtain QEA-A-006 (120 g, 14.2%). $^1$H NMR (CDCl₃, 400 MHz): δ 1.6-1.7 (m, 4H), 2.01 (d, J=0.8 Hz, 3H), 2.19 (m, 4H), 2.32 (d, J=0.8 Hz, 3H), 5.9 (t, J=3.6 Hz, 1H), 5.97 (d, J=8.4 Hz, 1H), 6.22-6.43 (m, 4H), 7.12 (dd, J=11.4 Hz, 15.4 Hz, 1H), 10.1 (d, J=8 Hz, 1H); $^{13}$C NMR (CDCl₃, 100 MHz): δ 13.33, 13.35, 22.65, 24.74, 26.54, 129.22, 129.38, 130.18, 132.59, 132.81, 134.60, 134.62, 136.32, 141.61, 155.09, 191.35. MS (m/z): [M+H]$^+$, 243.2.

QEA-F-002 (9-Cyclopentyl-3,7-dimethyl-nona-2,4,6,8-tetraenal)

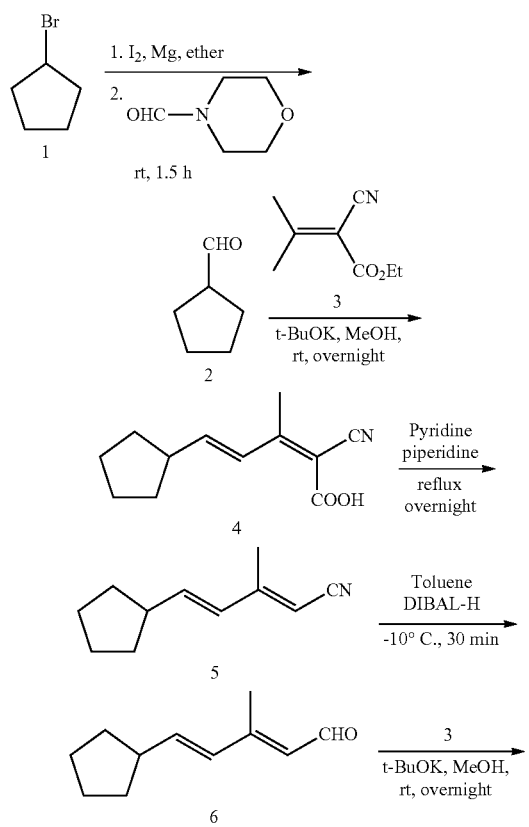

QEA-F-002

Preparation of Compound-2: To a stirred suspension of Mg metal (13.8 g, 0.57 mol) in dry THF (100 mL) at room temperature was slowly added a catalytic amount of iodine followed by Compound-1 (86 g, 0.57 mol) in ether (6 mL). Then a solution of N-formylpiperidine in ether was added. The resulting solution was stirred at room temperature for 1.5 h. The reaction was quenched with 3 M HCl, and the resulting mixture was extracted twice with ether. The combined organic layers were washed serially with aq. NaHCO₃ and brine, dried over anhydrous Na₂SO₄ and concentrated to obtain Compound-2 (24.2 g, 37.8%). IR: 1723 cm$^{-1}$.

Preparation of Compound-4: To a solution of t-BuOK (41.41 g, 369 mmol) in methanol (25 mL) cooled to 0° C. under nitrogen was added a solution of Compound-2 (24.2 g, 246 mmol) in methanol (10 mL) followed by Compound-3 (75.5 g, 493 mmol) in methanol (10 mL). The solution was stirred at room temperature overnight, and then evaporated. The residue was dissolved in water and washed with ethyl acetate. The resulting aqueous layer was acidified with diluted HCl and extracted twice with ethyl acetate. The combined organic layers were washed with brine, dried over anhydrous Na₂SO₄ and concentrated to obtain Compound-4 (84.6 g). The crude material was used for the next step without further purification.

Preparation of Compound-5: A solution of Compound-4 (84.6 g, 412 mmol) in piperidine (20 mL) and pyridine (20 mL) was refluxed overnight. The resulting solution was evaporated, and the residue was poured into diluted HCl and extracted twice with ethyl acetate. The combined organic layers were washed with brine, dried over anhydrous Na₂SO₄ and concentrated. The crude compound was purified by column chromatography on 100-200 mesh silica gel and eluted with 1% of ethyl acetate/hexane to obtain Compound-5 (4 g, 11.4%). MS (m/z): [M+H]$^+$, 162.2.

Preparation of Compound-6: To a stirred solution of Compound-5 (3.5 g, 21 mmol) in dry toluene (5 mL) at −10° C. was slowly added DIBAL-H (1 M in toluene, 2.4 mL). The reaction mixture was stirred at −10° C. for 30 min, poured into a solution of sodium potassium tartrate and stirred at 0° C. for 1 h. Then the mixture was filtered through celite and the filtrate was extracted twice with chloroform. The combined organic layers were dried over anhydrous Na₂SO₄ and concentrated. The residue was purified by column chromatography on 100-200 mesh silica gel and eluted with 0.5% ethyl acetate/hexane to obtain Compound-6 (600 mg, 16.8%). MS (m/z): [M+H]$^+$, 165.2.

Preparation of Compound-7: To a stirred solution of t-BuOK (1 g, 9.1 mol) in methanol at 0° C. under nitrogen was added a solution of Compound-3 (1.119 g, 7.3 mmol) and then Compound-6 (600 mg, 3.65 mmol) in methanol (10 mL). The resulting solution was stirred at room temperature overnight and then evaporated. The residue was diluted with water, washed with ethyl acetate, acidified with diluted HCl, and extracted twice with ethyl acetate. The combined organic layers were washed with brine, dried over anhydrous $Na_2SO_4$ and concentrated to obtain Compound-7. The crude material was used for the next step without further purification. MS (m/z): $[M+H]^+$, 272.3.

Preparation of Compound-8: To the above crude Compound-7 were added both piperidine (20 mL) and pyridine (20 mL) and the reaction mixture was refluxed overnight. Then the solution was evaporated, and the residue was poured into diluted HCl and extracted with ethyl acetate (2×100 mL). The combined organic layers were washed with brine, dried over anhydrous $Na_2SO_4$ and concentrated. The crude compound was purified by column chromatography on 100-200 mesh silica gel and eluted with 1% ethyl acetate/hexane to obtain Compound-8 (340 mg, 41.0%). MS (m/z): $[M+H]^+$, 228.3.

Preparation of QEA-F-002: To a stirred solution of Compound-8 (340 mg, 1.5 mmol) in dry toluene (5 mL) at −10° C. was slowly added DIBAL-H (1 M in toluene, 1.65 mL). The reaction mixture was stirred at −10° C. for 30 min and then poured into a solution of sodium potassium tartrate and stirred at 0° C. for 1 h. The resulting mixture was filtered through celite and the filtrate was extracted twice with chloroform. The combined organic layers were dried over anhydrous $Na_2SO_4$ and concentrated. The residue was purified by column chromatography on 100-200 mesh silica gel and eluted with 0.3% ethyl acetate/hexane to obtain QEA-F-002 (40 mg, 11.6%). $^1$H NMR (CDCl$_3$, 300 MHz): δ 1.2-1.4 (m, 8H), 1.9 (s, 3H), 2.1 (m, 1H), 2.3 (s, 3H), 5.8-5.9 (m, 1H), 5.9-6.0 (d, 1H), 6.1-6.2 (m, 2H), 6.3-6.4 (m, 1H), 7.1-7.2 (m, 1H), 10.1 (d, 1H). MS (m/z): $[M+H]^+$, 231.2.

QEA-B-001 (7-tert-Butyl-9-cyclohex-1-enyl-3-methyl-nona-2,4,6,8-tetraenal)

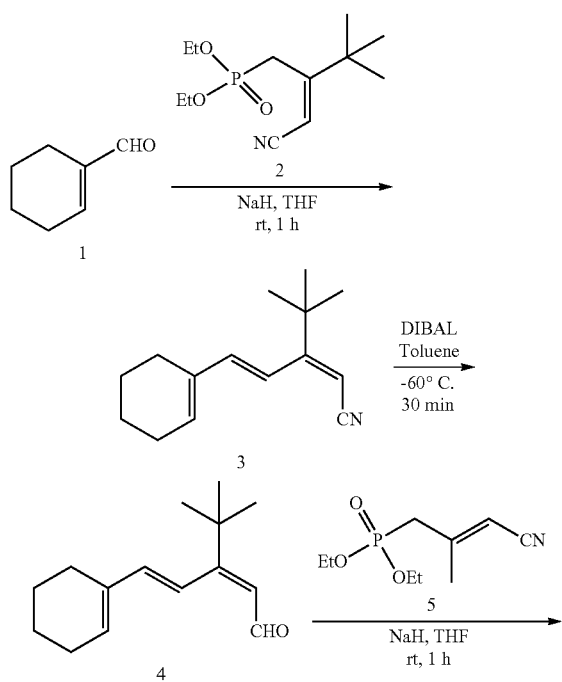

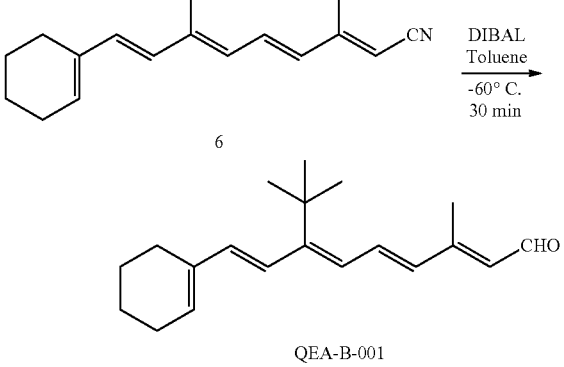

Preparation of Compound-3: To a stirred suspension of NaH (435 mg, 18 mmol) in dry THF (10 mL) at room temperature was added dropwise a solution of Compound-2 (3.53 g, 136 mmol) in dry THF (10 mL). The reaction mixture was stirred at room temperature for 1 h. Then a solution of Compound-1 (1 g, 9.0 mmol) in dry THF (10 mL) was slowly added and the resulting solution was stirred at room temperature for 1 h. the reaction was quenched with a saturated NH$_4$Cl solution and the resulting mixture was extracted twice with ethyl acetate. The combined organic layers were dried over anhydrous $Na_2SO_4$ and concentrated under vacuum. The crude compound was purified by column chromatography on 100-200 mesh silica gel and eluted with 1% ethyl acetate/hexane to obtain Compound-3 (590 mg, 37%). MS (m/z): $[M+H]^+$, 216.3.

Preparation of Compound-4: To a solution of Compound-3 (590 mg, 2.7 mmol) in dry toluene (5.9 mL) cooled to −60° C. under nitrogen was slowly added DIBAL-H (1 M in toluene, 3.2 mL) and the reaction mixture was stirred at −60° C. for 30 min. The mixture was then poured into a saturated sodium potassium tartrate solution and extracted with ethyl acetate. The organic layer was washed with water, dried over $Na_2SO_4$ and concentrated under vacuum. The residue was purified by column chromatography on 100-200 mesh silica gel and eluted with 1.2% ethyl acetate/petroleum ether to obtain compound-4 (250 mg, 41.8%). MS (m/z): $[M+H]^+$, 219.3.

Preparation of Compound-6: To a stirred suspension of NaH (132 mg, 5.5 mmoles) in dry THF at 0° C. under nitrogen was added a solution of Compound-5 (895 mg, 4.12 mmol) in dry THF (6 mL). The reaction solution was stirred at room temperature for 1 h and then cooled to 0° C. A solution of Compound-4 (600 mg, 2.75 mmol) in dry THF (6 ml) was slowly added, and the solution stirred at room temperature for 2 h. The reaction was quenched with a saturated NH$_4$Cl solution, and the resulting mixture was extracted with ethyl acetate. The combined organic layers were dried over anhydrous $Na_2SO_4$ and concentrated under vacuum. The residue was purified by column chromatography on 100-200 mesh silica gel and eluted with 1% ethyl acetate/petroleum ether to obtain Compound-6 (660 mg, 85.3%). MS (m/z): $[M+H]^+$, 282.4.

Preparation of QEA-B-001: To a stirred solution of Compound-6 (660 mg, 2.35 mmol) in dry toluene at −70° C. under nitrogen was added dropwise DIBAL-H (1 M in toluene, 2.76 mL). The reaction mixture was stirred at −70° C. for 30 min. Wet silica gel was added to the reaction mixture at −30° C. The resulting mixture was stirred at same temperature for 1 h, and then filtered. The filtrate was extracted thrice with ether. The combined organic layers were dried over anhydrous Na₂SO₄ and concentrated under vacuum. The residue was purified by column chromatography on 100-200 mesh silica gel and eluted with 1% ethyl acetate/petroleum ether to obtain QEA-B-001 (150 mg, 22.48%). $^1$H NMR (CDCl₃, 400 MHz): δ 1.11 (s, 9H), 1.62-1.74 (m, 4H), 2.16-2.23 (m, 4H), 2.24 (d, J=1.2 Hz, 3H), 5.80 (t, J=4 Hz, 1H), 5.93 (d, J=8.4 Hz, 1H), 6.04-6.19 (m, 3H), 6.35 (d, J=15.6 Hz, 1H), 7.13 (dd, J=10.8 Hz, 15.6 Hz, 1H), 10.07 (d, J=8 Hz, 1H); $^{13}$C NMR (CDCl₃, 100 MHz): δ 13.50, 22.60, 22.65, 24.65, 26.28, 29.92, 36.80, 121.7, 122.7, 128.5, 131.5, 133.6, 135.9, 136.2, 140.1, 156.0, 157.4, 191.5. MS (m/z): [M+H]⁺, 285.3

TEA-B-002 (5-tert-Butyl-7-cyclohex-1-enyl-hepta-2,4,6-trienal)

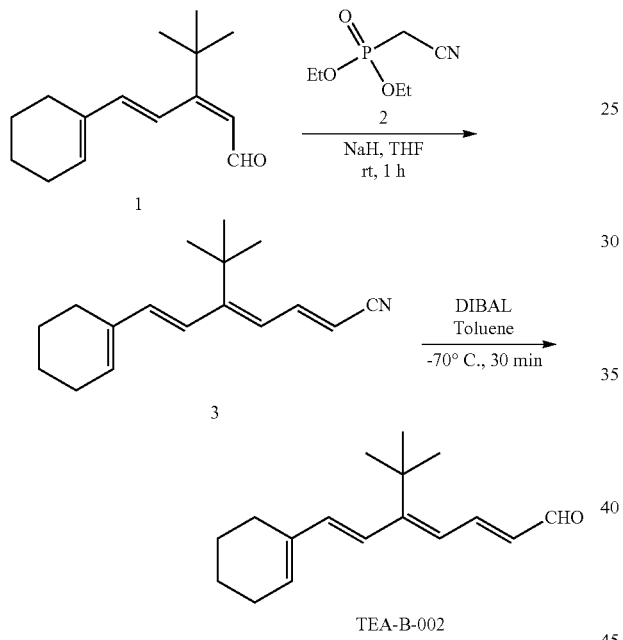

Preparation of Compound-1: To a stirred suspension of NaH (168 mg, 7.0 mmol) in dry THF (10 mL) at room temperature was slowly added dropwise a solution of Compound-2 (1.24 g, 7.0 mmol) in THF (15 mL) over 30 min. A solution of Compound-1 (770 mg, 3.5 mmol) in THF (15 mL) was slowly added at 0° C. and the resulting mixture was stirred at room temperature for 1 h. The reaction was quenched with a saturated NH₄Cl solution and the aqueous layer was extracted twice with ethyl acetate. The combined organic layers were dried over anhydrous Na₂SO₄ and concentrated under vacuum. The residue was purified by column chromatography on 100-200 mesh silica gel and eluted with 1% ethyl acetate/hexane to obtain of Compound-3 (770 mg, 91%). MS (m/z): [M+H]⁺, 282.4.

Preparation of TEA-B-002: To a stirred solution of Compound-3 (770 mg, 3.1 mmol) in dry toluene (10 mL) cooled to −70° C. under nitrogen was slowly added DIBAL-H (3.75 mL, 6.3 mmol) and the reaction mixture was stirred at −70° C. for 30 min. Then the solution was poured onto silica gel, stirred at 0° C. for 1 h and filtered. The filtrate was dried over Na₂SO₄ and concentrated under vacuum. The crude compound was purified by column chromatography on 100-200 mesh silica gel and eluted with 0.4% ethyl acetate/hexane to give TEA-B-002 (220 mg, 28.2%). $^1$H NMR (CDCl₃, 400 MHz): δ 1.14 (s, 9H), 1.62-1.76 (m, 4H), 2.21 (m, 4H), 5.88 (t, J=4 Hz, 1H), 6.06-6.20 (m, 3H), 6.3 (d, J=11.2 Hz, 1H), 7.148 (dd, J=11.2 Hz, 15.2 Hz, 1H), 9.54 (d, J=8 Hz, 1H); $^{13}$C NMR (CDCl₃, 100 MHz): δ 22.53, 22.56, 24.64, 26.3, 29.76, 37.23, 121.11, 121.3, 130.74, 132.83, 135.64, 141.34, 152.23, 163.67, 194.61. IR: 1681.49 cm⁻¹. MS (m/z): [M+H]⁺, 285.4.

QEA-D-001 (6-Bicyclohexyl-1,1'-dien-3-ylidene-3-methyl-hexa-2,4-dienal)

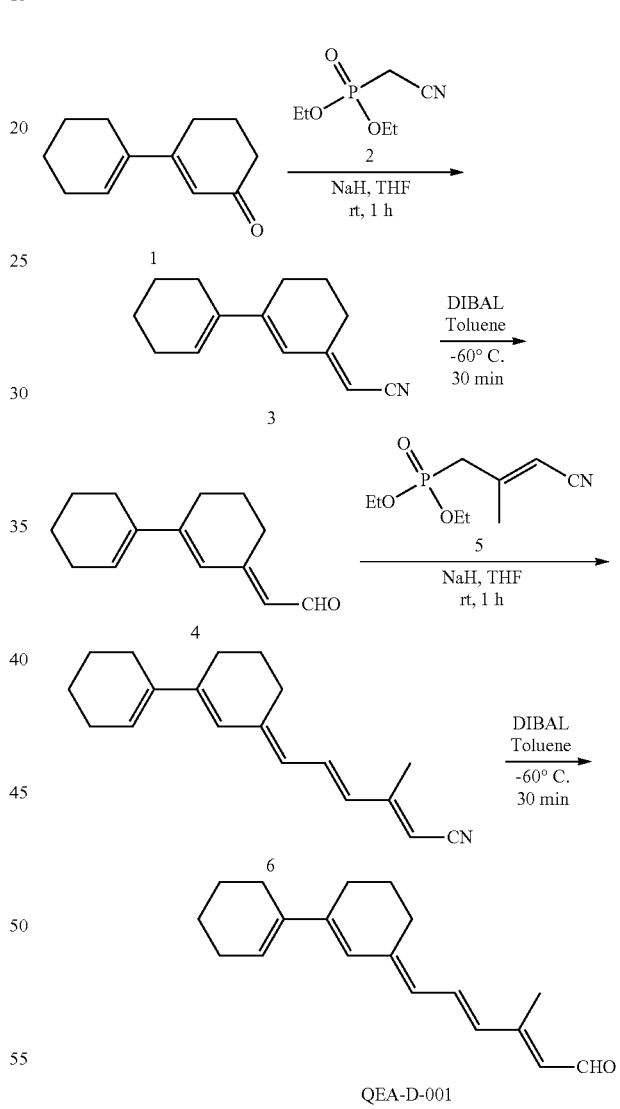

Preparation of Compound-3: To a stirred solution of NaH (245 mg, 10 mmol) in dry THF (10 mL) at room temperature was added dropwise a solution of Compound-2 (1.80 g, 10.0 mmol) in dry THF (10 mL). A solution of Compound-1 (900 mg, 5.1 mmol) in dry THF (10 mL) was slowly added at room temperature. The reaction mixture was stirred at room temperature for 1 h and the reaction was quenched with a saturated NH₄Cl solution. The aqueous layer was extracted twice with ethyl acetate. The combined organic layers were dried over anhydrous Na₂SO₄ and concentrated under vacuum. The crude compound was purified by column chromatography on 100-200 mesh silica gel and eluted with 2% ethyl acetate/hexane to obtain Compound-3 (960 mg, 94.4%). MS (m/z): [M+H]⁺, 200.3.

Preparation of Compound-4: To a solution of Compound-3 (100 mg, 0.5 mmol) in dry toluene (10 mL) cooled to −60° C. under nitrogen was slowly added DIBAL-H (1.7 M in toluene, 0.59 mL) and the reaction mixture was stirred at −60° C. for 30 min. Then the solution was poured onto wet silica gel and filtered. The filtrate was dried over Na₂SO₄ and concentrated to obtain compound-4 (115 mg). The crude material was used for the next step without further purification. MS (m/z): [M+H]⁺, 203.3.

Preparation of Compound-6: To a stirred suspension of NaH (108 mg, 4.5 mmol) in dry THF (10 mL) at 0° C. under nitrogen was added a solution of Compound-5 (740 mg, 3.4 mmol) in dry THF (10 mL). The resulting solution was stirred at room temperature for 1 h. Then a solution of Compound-4 (460 mg, 2.2 mmol) in dry THF (10 mL) was slowly added at 0° C. The mixture was stirred at room temperature for 1 h and the reaction was quenched with a saturated NH₄Cl solution. The aqueous layer was extracted twice with ethyl acetate. The combined organic layers were dried over anhydrous Na₂SO₄ and concentrated under vacuum. The residue was purified by column chromatography on 60-120 mesh silica gel and eluted with 1% ethyl acetate/hexane to obtain Compound-6 (550 mg, 96%). MS (m/z): [M+H]⁺, 266.4.

Preparation of QEA-D-001: To a stirred solution of Compound-6 (550 mg, 2 mmol) in toluene (5.5 mL) at −60° C. under nitrogen was added dropwise DIBAL-H (1.7 M in toluene, 2.4 mL). The reaction mixture was stirred at −60° C. for 30 min. Wet silica gel was added at 0° C., and the suspension was stirred at same temperature for 90 min. The mixture was filtered, and the precipitate was washed thrice with ether. The combined filtrate was dried over anhydrous Na₂SO₄ and concentrated under vacuum. The residue was purified by column chromatography on 100-200 mesh silica gel and eluted with 2% ethyl acetate/hexane to obtain QEA-D-001 (140 mg, 25.2%). ¹H NMR (CDCl₃, 400 MHz): δ 1.56-1.62 (m, 6H), 1.68-1.74 (m, 2H), 176-1.84 (m, 2H), 2.18-2.26 (m, 4H), 2.31 (s, 3H), 2.37 (t, J=6.2 Hz, 2H), 2.52 (m, 2H), 5.96 (d, J=8 Hz, 1H), 6.04 (t, J=4.2 Hz, 1H), 6.09 (d, J=12 Hz, 1H), 6.25 (s, 1H), 6.32 (d, J=15.2 Hz, 1H), 7.11 (dd, J=11.6 Hz, 15 Hz, 1H), 10.09 (d, J=8 Hz, 1H); ¹³C NMR (CDCl₃, 100 MHz): δ 13.32, 22.43, 22.72, 23.11, 25.64, 25.9, 26.13, 26.53, 125.1, 126.42, 126.53, 128.81, 132.76, 133.66, 136.61, 143.02, 144.24, 155.33, 191.3. MS (m/z): [M+H]⁺, 269.2.

TEA-B-004 (7-Cyclohex-1-enyl-5-phenyl-hepta-2,4,6-trienal)

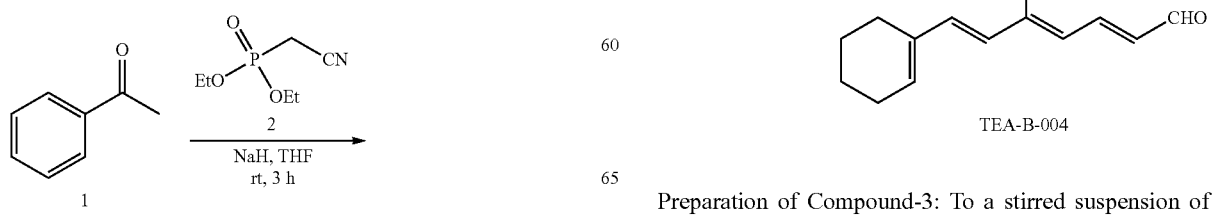

Preparation of Compound-3: To a stirred suspension of NaH (1.5 g, 62.4 mmol) in THF (25 mL) at 0° C. was added dropwise a solution of Compound-2 (11 g, 62.4 mmol) in dry THF (10 mL) and the reaction mixture was stirred for 20 min. Then a solution of Compound-1 (5 g, 41.6 mmol) in THF (25 mL) was slowly added and the resulting solution was stirred at room temperature for 3 h. The reaction was quenched with a saturated NH$_4$Cl solution and the aqueous layer was extracted twice with ethyl acetate. The combined organic layers were washed with brine, dried over anhydrous Na$_2$SO$_4$ and concentrated. The crude compound was purified by column chromatography on 100-200 mesh silica gel and eluted with 1% ethyl acetate/petroleum ether to obtain Compound-3 (5.4 g, 90.7%). MS (m/z): [M+H]$^+$, 144.1.

Preparation of Compound-4: To a stirred solution of Compound-3 (500 mg, 3.49 mmol) in CCl$_4$ (3.5 mL) at room temperature was added NBS (1.65 g, 13.9 mmol) followed by AIBN (57 mg, 0.35 mmol) and the mixture was refluxed overnight. Then the reaction mixture was filtered and the filtrate was concentrated under vacuum. The crude compound was purified by column chromatography on 100-200 mesh silica gel and eluted with 1% ethyl acetate/petroleum ether to obtain Compound-4 (340 mg, 43.9%). MS (m/z): [M+H]$^+$, 223.1.

Preparation of Compound-5: To a stirred solution of Compound-4 (340 mg, 1.53 mmol) in toluene (3.4 mL) at room temperature was added dropwise a solution of P(OEt)$_3$ (TEP, 0.38 g, 2.29 mmol). The solution was refluxed overnight and concentrated. The crude compound was purified by column chromatography on 100-200 mesh silica gel and eluted with 30% ethyl acetate/petroleum ether to obtain Compound-5 (380 mg, 89%). MS (m/z): [M+H]$^+$, 279.2.

Preparation of Compound-7: To a stirred suspension of NaH (327 mg, 13.6 mmol) in dry THF (15 mL) at 0° C. was added dropwise a solution of Compound-5 (3.79 g, 13.6 mmol) in THF (10 mL). The reaction mixture was stirred for at 55° C. for 40 min. Then a solution of Compound-6 (1 g, 9.1 mmol) in THF (15 mL) was slowly added and the resulting solution was stirred at room temperature for 1 h. The reaction was quenched with a saturated NH$_4$Cl solution and the aqueous layer was extracted thrice with ethyl acetate. The combined organic layers were washed with brine, dried over anhydrous Na$_2$SO$_4$ and concentrated under vacuum. The crude compound was purified by column chromatography on 100-200 mesh silica gel and eluted with 1% ethyl acetate/petroleum ether to obtain Compound-7 (940 mg, 44%). MS (m/z): [M+H]$^+$, 235.3.

Preparation of Compound-8: To a stirred solution of Compound-7 (940 mg, 3.9 mmol) in dry toluene (9.4 mL) at −70° C. was added dropwise DIBAL-H (1.7 M in toluene, 4.7 mL). The reaction mixture was stirred for 1 h and the reaction was quenched with wet silica gel at 0° C. The resulting mixture was stirred for 1 h and filtered. The filtrate was dried over Na$_2$SO$_4$ and concentrated under vacuum. The crude compound was purified by column chromatography on 100-200 mesh silica gel and eluted with 0.5% ethyl acetate/petroleum ether to obtain Compound-8 (410 mg, 44%). MS (m/z): [M+H]$^+$, 239.3.

Preparation of Compound-9: To a stirred suspension of NaH (82.5 mg, 0.1 mmol) in dry THF (4.1 mL) at 0° C. under nitrogen was added dropwise a solution of Compound-2 (609 mg, 3.4 mmol) in dry THF (4.1 mL). The reaction mixture was stirred at 0° C. for 20 min and a solution of Compound-8 (410 mg, 1.7 mmol) in THF (10 mL) was slowly added. The resulting reaction solution was stirred at room temperature for 45 min. The reaction was quenched with a saturated NH$_4$Cl solution and the aqueous layer was extracted thrice with ethyl acetate. The combined organic layer was washed with brine solution, dried over anhydrous Na$_2$SO$_4$ and concentrated under vacuum. The crude compound was purified by column chromatography on 60-120 mesh silica gel and eluted with 1% ethyl acetate/petroleum ether to obtain Compound-9 (282 mg, 62.7%). MS (m/z): [M+H]$^+$, 262.2.

Preparation of TEA-B-004: To a stirred solution of Compound-9 (282 mg, 1 mmol) in toluene (3 mL) cooled to −70° C. under nitrogen was added dropwise DIBAL-H (1.7 M in toluene, 1.27 mL). This reaction solution was stirred at −70° C. for 30 min, poured onto wet silica gel at 0° C. and stirred for 1 h. The reaction mixture was filtered through silica gel, dried over anhydrous Na$_2$SO$_4$ and concentrated. The crude compound was purified by column chromatography on 60-120 mesh silica gel and eluted with 1% ethyl acetate/petroleum ether to obtain TEA-B-004 (80 mg, 28%). $^1$H NMR (CDCl$_3$, 400 MHz): δ 1.58-1.78 (m, 4H), 2.12-2.22 (m, 4H), 5.78 (t, J=4 Hz, 1H), 6.05 (d, J=16 Hz, 1H), 6.16 (dd, J=8.2 Hz, 15 Hz, 1H), 6.46 (d, J=15.6 Hz, 1H), 6.53 (d, J=11.6 Hz, 1H), 9.97 (dd, J=11.6 Hz, 15.6 Hz, 1H), 7.17-7.19 (m, 2H), 7.41-7.47 (m, 3H), 9.36 (d, J=8 Hz, 1H); $^{13}$C NMR (CDCl$_3$, 100 MHz): δ 22.46, 22.53, 24.65, 26.58, 128.15, 128.2, 128.36, 128.6, 129.8, 131.11, 135.17, 136.63, 141.15, 149.9, 153.09, 194.0. MS (m/z): [M+H]$^+$, 265.2.

QEA-C-002 (7-tert-Butyl-3-methyl-9-(5,6,7,8-tetra-hydro-naphthalen-2-yl)-nona-2,4,6,8-tetraenal)

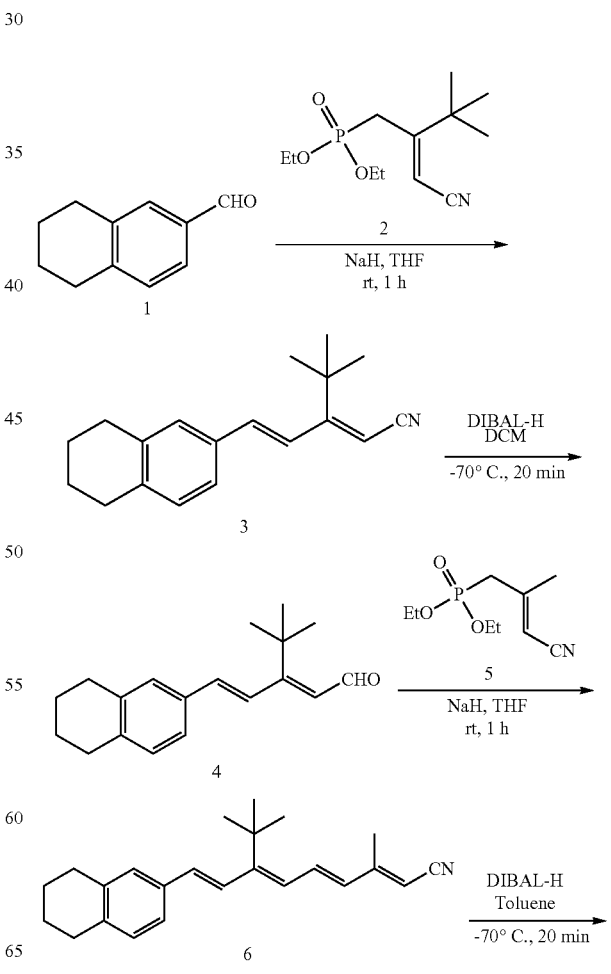

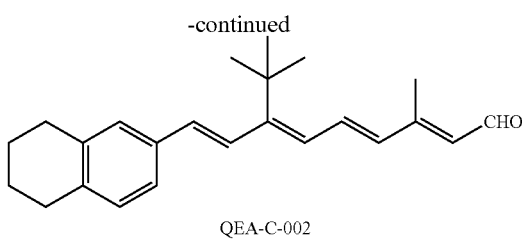

QEA-C-002

Preparation of Compound-3: To a stirred suspension of NaH (1.795 g, 74.8 mmol) in dry THF (10 mL) at room temperature was added dropwise a solution of Compound-2 (11.6 g, 45.0 mmol) in dry THF (10 mL). This reaction mixture was stirred at room temperature for 45 min when a solution of Compound-1 (6.0 g, 37.4 mmol) in dry THF (10 mL) was slowly added and the reaction was stirred at room temperature for 1 h. Then the reaction was quenched with a saturated NH$_4$Cl solution and the aqueous layer was extracted twice with ethyl acetate. The combined organic layers were dried over anhydrous Na$_2$SO$_4$ and concentrated under vacuum. The crude compound was purified by column chromatography on 100-200 mesh silica gel and eluted with 2% ethyl acetate/petroleum ether to obtain Compound-3 (8.0 g, 80.6%). MS (m/z): [M+H]$^+$, 266.3.

Preparation of Compound-4: To a solution of Compound-3 (8 g, 30 mmol) in DCM (80 mL) cooled to −70° C. under nitrogen, DIBAL-H (1.7 M in DCM, 32 mL) was slowly added and the mixture was stirred at −70° C. for 20 min. The reaction solution was poured into 0.3 M H$_2$SO$_4$ solution at 0° C., stirred at room temperature for 20 min, and extracted thrice with ethyl acetate. The combined organic layers were dried over Na$_2$SO$_4$ and concentrated under reduced pressure. The residue was purified by column chromatography on 100-200 mesh silica gel and eluted with 0.6% ethyl acetate/petroleum ether to obtain Compound-4 (3.14 g, 38.8%). MS (m/z): [M+H]$^+$, 269.3.

Preparation of Compound-6: To a stirred suspension of NaH (89 mg, 3.7 mmol) in dry THF (10 mL) at 0° C. under nitrogen was added a solution of Compound-5 (606 mg, 2.79 mmol) in dry THF (11 mL). The reaction solution was stirred at room temperature for 1 h and then a solution of Compound-4 (500 mg, 1.86 mmol) in dry THF (11 mL) was slowly added at 0° C. The mixture was stirred at room temperature for 1 h. The reaction was quenched with a saturated NH$_4$Cl solution and the resulting mixture was extracted thrice with ethyl acetate. The combined organic layers were dried over anhydrous Na$_2$SO$_4$ and concentrated under vacuum. The residue was purified by column chromatography on 60-120 mesh silica gel and eluted with 0.5% ethyl acetate/petroleum ether to obtain Compound-6 (580 mg, 93.9%). MS (m/z): [M+H]$^+$, 332.3.

Preparation of QEA-C-002: To a stirred solution of Compound-6 (580 mg, 1.75 mmol) in dry toluene at −70° C. under nitrogen was added dropwise DIBAL-H (1.7 M in toluene, 1.85 mL). The reaction mixture was stirred at −70° C. for 20 min, and poured into a 0.3 M H$_2$SO$_4$ solution at 0° C. This mixture was stirred at room temperature for 30 min and extracted thrice with ethyl acetate. The combined organic layers were dried over Na$_2$SO$_4$ and concentrated under vacuum. The residue was purified column chromatography on 60-120 mesh silica gel and eluted with 0.4-0.5% ethyl acetate/petroleum ether to obtain QEA-C-002 (200 mg, 34.2%). $^1$H NMR (CDCl$_3$, 400 MHz): δ 1.17 (s, 9H), 1.82 (m, 4H), 2.20 (d, J=0.8 Hz, 3H), 2.79 (d, J=3.6 Hz, 4H), 5.95 (d, J=8 Hz, 1H), 6.27 (d, J=10.8 Hz, 1H), 6.41 (d, J=15.6 Hz, 1H), 6.47 (d, J=16 Hz, 1H), 6.73 (d, J=16 Hz, 1H), 7.08 (d, J=16 Hz, 1H), 7.16-7.26 (m, 3H), 10.07 (d, J=7.6 Hz, 1H); $^{13}$C NMR (CDCl$_3$, 100 MHz): δ 13.43, 23.38, 29.52, 29.67, 29.90, 36.91, 107.5, 123.4, 123.8, 125.0, 128.8, 129.8, 134.2, 134.5, 135.8, 136.2, 137.8, 155.8, 156.8, 191.5. MS (m/z): [M+H]$^+$, 335.2.

TEA-C-001 (5-tert-Butyl-7-(5,6,7,8-tetrahydro-naphthalen-2-yl)-hepta-2,4,6-trienal)

Preparation of Compound-3: To a stirred suspension of NaH (65 mg, 2.79 mmol) in dry THF (5 mL) at room temperature was added dropwise a solution of Compound-2 (495 mg, 2.79 mmol) in dry THF (5 mL) and the resulting solution was stirred for 30 min. Then a solution of Compound-1 (500 mg, 1.86 mmol) in THF (5 mL) was slowly added at 0° C. and the solution was stirred at room temperature for 30 min. The reaction was quenched with a saturated NH$_4$Cl solution and the aqueous layer was extracted twice with ethyl acetate. The combined organic layers were dried over anhydrous Na$_2$SO$_4$ and concentrated under vacuum. The residue was purified by column chromatography on 100-200 mesh silica gel and eluted with 0.5% ethyl acetate/petroleum ether to obtain Compound-3 (470 mg, 86.6%). MS (m/z): [M+H]$^+$, 292.3.

Preparation of TEA-C-001: To a stirred solution of Compound-3 (470 mg, 1.60 mmol) in dry toluene cooled to −70° C. under nitrogen was slowly added DIBAL-H (1.7 M, 1.71 mL) and the reaction mixture was stirred for 20 min. The reaction was quenched with a cold 3 M H$_2$SO$_4$. The resulting mixture was stirred at room temperature for 10 min and then extracted thrice with ethyl acetate. The combined organic layers were dried over Na$_2$SO$_4$ and concentrated under vacuum. The crude compound was purified by column chromatography on 100-200 mesh silica gel and eluted with 2% ethyl acetate/petroleum ether to obtain TEA-C-001 (180 mg, 38.2%). $^1$H NMR (CDCl$_3$, 400 MHz): δ 1.20 (s, 9H), 1.82 (m, 4H), 2.80 (m, 4H), 6.21 (dd, J=15.2 Hz, 8.4 Hz, 1H), 6.39 (d, J=10.8 Hz, 1H), 6.47 (d, J=16 Hz, 1H), 6.76 (d, J=15.6 Hz, 1H), 7.10 (d, J=8 Hz, 1H), 7.18 (s, 1H), 7.24 (m, 1H), 7.55 (dd, J=15.2 Hz, 10.8 Hz 1H), 9.50 (d, J=8 Hz, 1H); $^{13}$C NMR (CDCl$_3$, 100 MHz): δ 23.36, 29.55, 29.65, 29.78, 37.35, 122.0, 124.0, 124.1, 127.9, 129.9, 131.2, 133.9, 137.5, 137.9, 138.2, 151.8, 163.0, 194.6. MS (m/z): [M+H]$^+$, 295.3.

QEA-C-001 (7-tert-Butyl-3-methyl-9-phenyl-nona-2,4,6,8-tetraenal)

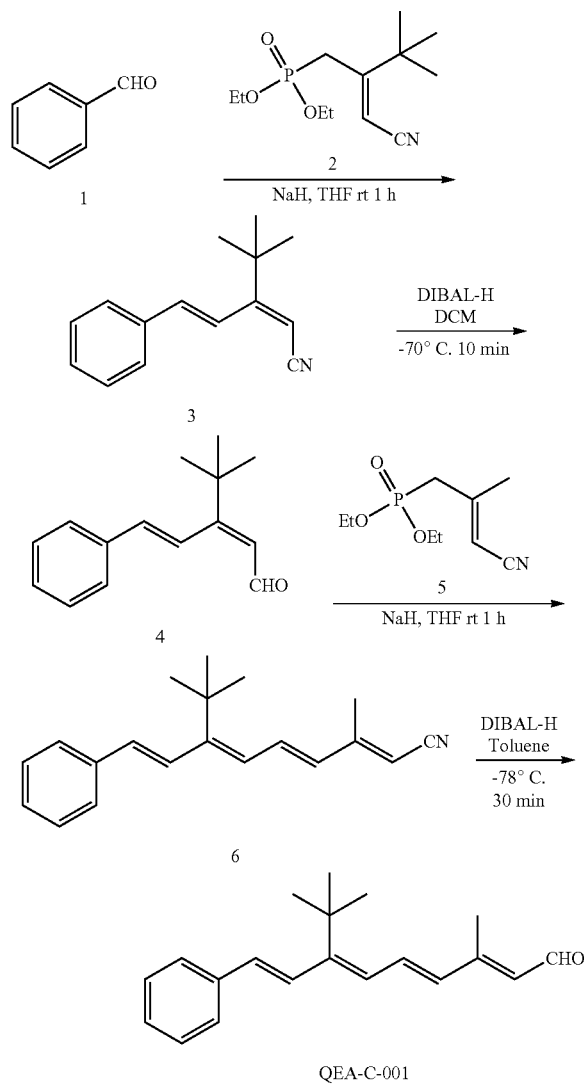

Preparation of Compound-3: To a stirred suspension of NaH (1.36 g, 56.6 mmol) in dry THF (10 mL) at 0° C. was slowly added a solution of Compound-2 (8.8 g, 34 mmol) in dry THF (10 mL). The reaction mixture was stirred at room temperature for 20 min. Then a solution of Compound-1 (3.0 g, 28.3 mmol) in dry THF (10 mL) was added and the resulting solution was stirred at room temperature for 1 h. The reaction was quenched with a saturated NH$_4$Cl solution and the aqueous layer was extracted twice with ethyl acetate. The combined organic layers were dried over anhydrous Na$_2$SO$_4$ and concentrated under vacuum. The crude compound was purified by column chromatography on 60-120 mesh silica gel and eluted with 2% ethyl acetate/petroleum ether to obtain Compound-3 (4.0 g, 67%). MS (m/z): [M+H]$^+$, 212.2.

Preparation of Compound-4: To a solution of Compound-4 (3.0 g, 14.2 mmol) in DCM (30 mL) cooled to −70° C. under nitrogen was slowly added DIBAL-H (1.7 M in DCM, 12.5 mL) and the mixture was stirred for 10 min. The reaction solution was poured into a 0.3 M H$_2$SO$_4$ solution at 0° C. and stirred for 15 min. The aqueous layer was extracted thrice with ethyl acetate, and the combined organic layers were dried over anhydrous Na$_2$SO$_4$ and concentrated under vacuum. The residue was purified by column chromatography on 60-120 mesh silica gel and eluted with 0.8% ethyl acetate/petroleum ether to obtain Compound-4 (920 mg, 30.6%). MS (m/z): [M+H]+, 215.2.

Preparation of Compound-6: To a stirred suspension of NaH (84 mg, 3.45 mmol) in dry THF (10 mL) at 0° C. under nitrogen was added a solution of Compound-5 (608 mg, 2.80 mmol) in dry THF (5 mL). The reaction mixture was stirred at room temperature for 1 h and then a solution of Compound-4 (500 mg, 2.33 mmol) in dry THF (11 mL) was slowly added at 0° C. The solution was stirred at room temperature for 1 h. Then the reaction was quenched with a saturated NH$_4$Cl solution and the mixture was extracted thrice with ethyl acetate. The combined organic layers were dried over anhydrous Na$_2$SO$_4$ and concentrated under reduced pressure. The residue was purified by column chromatography on 100-200 mesh silica gel eluted with 0.3% ethyl acetate/petroleum ether to obtain Compound-6 (560 mg, 86.5%). MS (m/z): [M+H]+, 278.3.

Preparation of QEA-C-001: To a stirred solution of Compound-6 (560 mg, 2.0 mmol) in dry toluene (2 mL) at −78° C. under nitrogen was added dropwise DIBAL-H (1.7 M solution in toluene, 1.78 mL). The resulting solution was stirred at −78° C. for 30 min, poured into a 0.3 M H$_2$SO$_4$ solution at 0° C. and stirred at room temperature for 30 min. The mixture then was extracted thrice with ethyl acetate, dried over Na$_2$SO$_4$ and concentrated under vacuum. The residue was purified by column chromatography on 60-120 mesh silica gel and eluted with 0.6-1% ethyl acetate/petroleum ether to obtain QEA-C-001 (200 mg, 35%). $^1$H NMR (CDCl$_3$, 400 MHz): δ 1.18 (s, 9H), 2.21 (d, J=1.2 Hz, 3H), 5.96 (d, J=8.4 Hz, 1H), 6.30 (d, J=10.8 Hz, 1H), 6.42 (d, J=15.2 Hz, 1H), 6.54 (d, J=16 Hz, 1H), 6.80 (d, J=16 Hz, 1H), 7.21 (dd, J=15.2 Hz, 10.8 Hz, 1H), 7.31 (m, 1H), 7.38 (m, 2H), 7.46 (m, 2H), 10.08 (d, J=8 Hz, 1H); $^{13}$C NMR (CDCl$_3$, 100 MHz): δ 13.41, 29.90, 36.91, 123.7, 126.1, 126.7, 128.2, 128.9, 129.0, 134.4, 135.5, 136.0, 137.1, 155.6, 156.4, 191.5. MS (m/z): [M+H]$^+$, 281.3.

QEA-C-003 (3-Methyl-7-phenyl-9-(4-trifluoromethyl-phenyl)-nona-2,4,6,8-tetraenal)

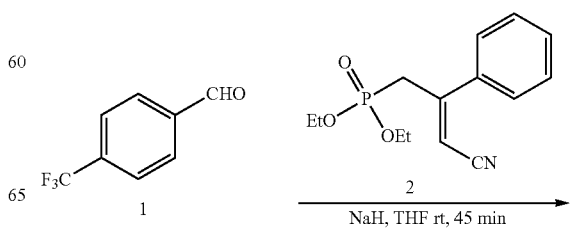

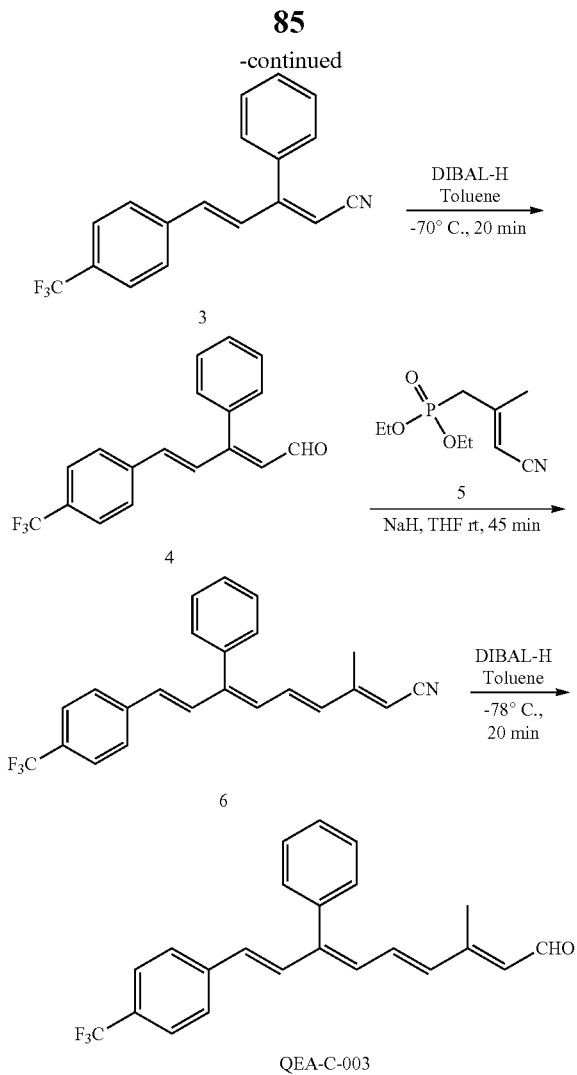

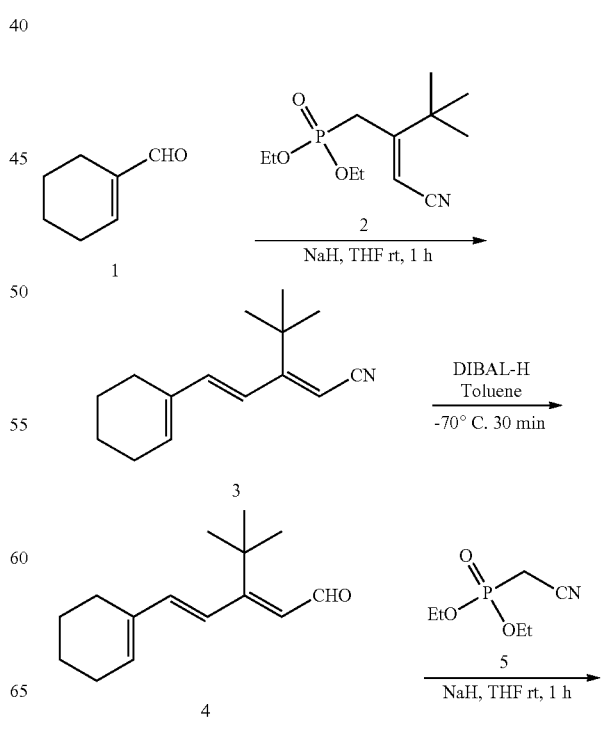

mesh silica gel and eluted with 0.2% ethyl acetate/petroleum ether to obtain Compound-4 (1.15 g, 85%). MS (m/z): [M+H]$^+$, 303.2.

Preparation of Compound-6: To a stirred suspension of NaH (60 mg, 2.48 mmol) in dry THF at 0° C. under nitrogen was slowly added a solution of Compound-5 (467 mg, 2.15 mmol) in dry THF (10 mL). The reaction solution was stirred at room temperature for 45 min and then a solution of Compound-4 (500 mg, 1.6 mmol) in dry THF (10 mL) was slowly added at 0° C. and the resulting solution was stirred at room temperature for 1 h. The reaction was quenched with a saturated NH$_4$Cl solution, extracted thrice with ethyl acetate, dried over anhydrous Na$_2$SO$_4$ and concentrated under vacuum. The residue was purified by column chromatography on 60-120 mesh silica gel and eluted with 1.5% ethyl acetate/petroleum ether to obtain Compound-6 (310 mg, 51.3%). MS (m/z): [M+H]$^+$, 366.3.

Preparation of QEA-C-003: To a stirred solution of Compound-6 (310 mg, 0.84 mmol) in dry toluene (10 mL) at −78° C. under nitrogen was added dropwise DIBAL-H (1.7 M in toluene, 0.99 mL). The reaction mixture was stirred at −78° C. for 20 min. The mixture was poured into a 0.3 M H$_2$SO$_4$ solution at 0° C., stirred at room temperature for 30 min, extracted thrice with ethyl acetate, dried over Na$_2$SO$_4$ and concentrated under vacuum. The residue was purified by column chromatography on 230-400 mesh silica and eluted with 1.4% ethyl acetate/petroleum ether to obtain QEA-C-003 (100 mg, 32%). $^1$H NMR (CDCl$_3$, 400 MHz): δ 2.07 (d, J=1.2 Hz, 3H), 5.96 (d, J=8 Hz, 1H), 6.29 (d, J=14 Hz, 1H), 6.47 (d, J=14.4 Hz, 1H), 6.60-6.65 (m, 2H), 7.14 (d, J=16 Hz, 1H), 7.23 (m, 1H), 7.42-7.54 (m, 8H). 10.05 (d, J=8 Hz, 1H); $^{13}$C NMR (CDCl$_3$, 100 MHz): δ 13.20, 125.8 (m), 127.0, 128.3, 128.8, 129.9, 130.0, 132.3, 133.1, 133.6, 134.6, 136.7, 137.1, 140.6, 146.6, 154.4, 191.4. MS (m/z): [M+H]$^+$, 369.3.

PEA-B-001 (3,9-Di-tert-butyl-11-cyclohex-1-enyl-undeca-2,4,6,8,10-pentaenal)

Preparation of Compound-3: To a stirred suspension of NaH (393 mg, 16.3 mmol) in dry THF (10 mL) at 0° C. under nitrogen was added dropwise a solution of Compound-2 (3.65 g, 13.0 mmol) in dry THF (10 mL). The resulting mixture was stirred at room temperature for 45 min. Then a solution of Compound-1 (1.9 g, 11.0 mmol) in dry THF (10 mL) was slowly added and the reaction solution was stirred at room temperature for 1 h. The reaction was quenched with a saturated NH$_4$Cl solution and the aqueous layer was extracted twice with ethyl acetate. The combined organic layers were dried over anhydrous Na$_2$SO$_4$ and concentrated under vacuum. The crude compound was purified by column chromatography on 100-200 mesh silica gel and eluted with 0.5% ethyl acetate/petroleum ether to obtain Compound-3 (1.34 g, 41%). MS (m/z): [M+H]$^+$, 300.2.

Preparation of Compound-4: To a solution of Compound-3 (1.34 g, 44 mmol) in toluene (10 mL) cooled to −70° C. under nitrogen was slowly added DIBAL-H (1.7 M in toluene, 5.26 mL) and the reaction mixture was stirred at −70° C. for 20 min. Then the solution was poured into a 0.3 M H$_2$SO$_4$ solution at 0° C. and stirred for 20 min at room temperature. The aqueous layer was extracted twice with ethyl acetate. The combined organic layers were dried over anhydrous Na$_2$SO$_4$ and concentrated under vacuum. The residue was purified by column chromatography on 100-200

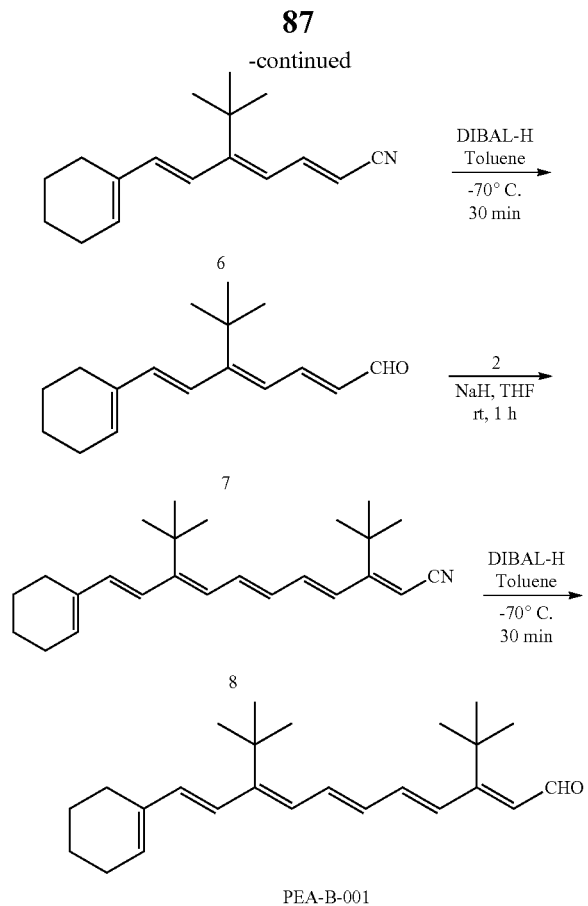

Preparation of Compound-3: To a stirred suspension of NaH (1.74 g, 72.6 mmol) in dry THF (30 mL) at 0° C. was slowly added dropwise a solution of Compound-2 (14.1 g, 54.0 mmol) in dry THF (5 mL). The reaction mixture was stirred at room temperature for 1 h. Then a solution of Compound-1 (4 g, 36.0 mmol) in dry THF (5 mL) was slowly added and the reaction mixture was stirred at room temperature for 1 h. The reaction mixture was quenched with a saturated NH$_4$Cl solution and the aqueous layer was extracted thrice with ethyl acetate. The combined organic layers were dried over anhydrous Na$_2$SO$_4$ and concentrated under vacuum. The crude compound was purified by column chromatography on 100-200 mesh silica gel and eluted with 0.2% ethyl acetate/petroleum ether to obtain Compound-3 (3.6 g, 46%). MS (m/z): [M+H]$^+$, 216.2.

Preparation of Compound-4: To a solution of Compound-3 (3 g, 13.0 mmol) in dry toluene (10 mL) cooled to −70° C. under nitrogen was slowly added DIBAL-H (1.7 M in toluene, 16.4 mL) and the solution was stirred at −70° C. for 30 min. The reaction mixture was poured onto silica gel at 0° C., stirred for 1 h and filtered. The filtrate was washed with ether, dried over anhydrous Na$_2$SO$_4$ and concentrated under reduced pressure. The residue was purified by column chromatography on 100-200 mesh silica gel and eluted with 0.5% ethyl acetate/petroleum ether to obtain Compound-4 (640 mg, 21%). MS (m/z): [M+H]$^+$, 219.2.

Preparation of Compound-6: To a stirred suspension of NaH (103 mg, 4.3 mmol) in dry THF (10 mL) at 0° C. under nitrogen was added a solution of Compound-5 (456 mg, 4.3 mmol) in dry THF (10 mL). The reaction mixture was stirred at 0° C. for 30 min, then a solution of Compound-4 (640 mg, 2.9 mmol) in dry THF (10 mL) was slowly added and stirred at room temperature for 1 h. The reaction mixture was quenched with a saturated NH$_4$Cl solution, extracted thrice with ethyl acetate, dried over anhydrous Na$_2$SO$_4$ and concentrated. The residue was purified by column chromatography on 60-120 mesh silica gel and eluted with 0.5% ethyl acetate/petroleum ether to obtain Compound-6 (580 mg, 82%). MS (m/z): [M+H]$^+$, 242.2.

Preparation of Compound-7: To a stirred solution of Compound-6 (540 mg, 2.1 mmol) in dry toluene (10 mL) at −70° C. under nitrogen was added dropwise DIBAL-H (1.7 M solution in Toluene, 2.6 mL). The reaction mixture was stirred at −70° C. for 30 min, then poured onto silica gel at 0° C. and stirred for 2 h before filtration. The precipitate was washed with ether, and the filtrate was dried over anhydrous Na$_2$SO$_4$ and concentrated under vacuum. The residue was purified by column chromatography on 100-200 mesh silica gel and eluted with 0.5% ethyl acetate/petroleum ether to obtain Compound-7 (230 mg, 42%). MS (m/z): [M+H]$^+$, 245.2.

Preparation of Compound-8: To a stirred suspension of NaH (45 mg, 1.8 mmol) in dry THF (10 mL) at 0° C. under nitrogen was added a solution of Compound-8 (487 mg, 1.8 mmol) in dry THF (10 mL). The reaction mixture was stirred at room temperature for 45 min A solution of Compound-7 (230 mg, 0.9 mmol) in dry THF (10 mL) was slowly added at 0° C. and stirred at room temperature for 2 h. The reaction mixture was quenched with a saturated NH$_4$Cl solution, extracted thrice with ethyl acetate, dried over anhydrous Na$_2$SO$_4$ and concentrated under vacuum. The residue was purified by column chromatography on 60-120 mesh silica gel and eluted with 0.5% ethyl acetate/petroleum ether to obtain Compound-8 (210 mg, 64%). MS (m/z): [M+H]$^+$, 350.3

Preparation of PEA-B-001: To a stirred solution of Compound-8 (210 mg, 0.6 mmol) in dry toluene (10 mL) at −70° C. under nitrogen DIBAL-H (1.7 M solution in toluene, 0.53 mL) was added dropwise. This reaction mixture was stirred at −70° C. for 30 min, then the reaction was quenched with a 0.3 M H$_2$SO$_4$ solution at 0° C. The aqueous layer was extracted thrice with ethyl acetate, and the combined organic layers were dried over anhydrous Na$_2$SO$_4$ and concentrated under vacuum. The residue was purified by column chromatography on 60-120 mesh silica gel and eluted with 0.4-0.5% ethyl acetate/petroleum ether to obtain PEA-B-001 (100 mg, 47.3%). $^1$H NMR (CDCl$_3$, 300 MHz): δ 1.10 (s, 9H), 1.14 (s, 9H), 1.61-1.74 (m, 4H), 2.19 (m, 4H), 5.82 (t, J=8 Hz, 1H), 6.00-6.16 (m, 4H), 6.23-6.44 (m, 3H), 6.74 (dd, J=14 Hz, 11.2 Hz, 1H), 9.66 (d, J=7.2 Hz, 1H); $^{13}$C NMR (CDCl$_3$, 100 MHz): δ 22.63, 22.88, 24.63, 26.21, 29.47, 29.92, 36.56, 37.19, 107.4, 121.7, 125.3, 125.9, 130.2, 131.1, 135.8, 136.3, 139.2, 141.9, 154.9, 172.7, 194.2. MS (m/z): [M+H]$^+$, 353.3.

QEA-E-001 (9-Cyclohex-1-enyl-3-methyl-7-phenyl-nona-2,4,6,8-tetraenal)

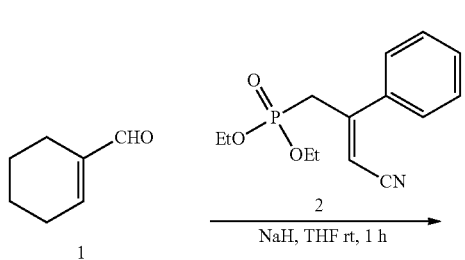

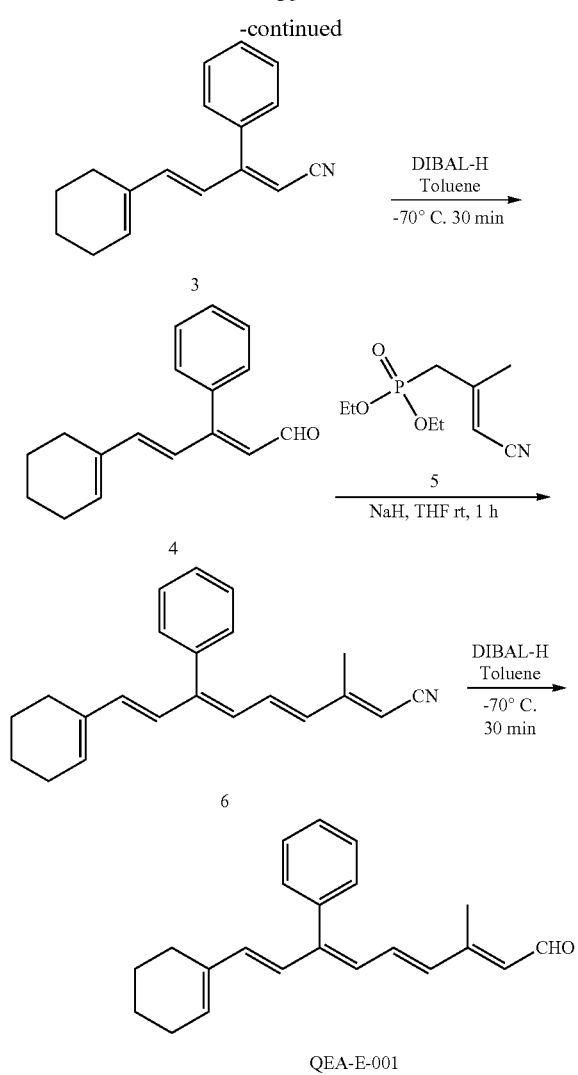

0.5% ethyl acetate/petroleum ether to obtain Compound-4 (530 mg, 72.7%). MS (m/z): [M+H]+, 239.2.

Preparation of Compound-6: To a stirred suspension of NaH (75 mg, 3.13 mmol) in dry THF (10 mL) at 0° C. under nitrogen was added a solution of Compound-5 (590 mg, 2.7 mmol) in dry THF (10 mL). The reaction mixture was stirred at room temperature for 40 min and then a solution of Compound-4 (500 mg, 2.09 mmol) in dry THF (10 mL) was slowly added at 0° C. This mixture was stirred at room temperature for 1 h. Then the reaction was quenched with a saturated $NH_4Cl$ solution, and extracted thrice with ethyl acetate. The combined organic layers were dried over anhydrous $Na_2SO_4$ and concentrated under vacuum. The residue was purified by column chromatography on 100-200 mesh silica gel and eluted with 0.5% ethyl acetate/petroleum ether to obtain Compound-6 (400 mg, 63.2%). MS (m/z): [M+H]+, 302.2.

Preparation of QEA-E-001: To a stirred solution of Compound-6 (400 mg, 1.3 mmol) in dry toluene (10 mL) at −70° C. under nitrogen was added dropwise DIBAL-H (1.7 M in toluene, 1.12 mL). The reaction mixture was stirred at −70° C. for 20 min. The reaction was quenched with a 0.3 M $H_2SO_4$ solution at 0° C. The aqueous layer was extracted thrice with ethyl acetate, and the combined organic layers were dried over anhydrous $Na_2SO_4$ and concentrated under vacuum. The residue was purified by column chromatography on silica geland eluted with 0.5% ethyl acetate/petroleum ether to obtain QEA-E-001 (60 mg, 14.8%). $^1$H NMR ($CDCl_3$, 300 MHz): δ 1.6-1.8 (m, 4H), 2-2.3 (m, 7H), 5.7-5.8 (m, 1H), 5.9-6.0 (m, 2H), 6.4-6.5 (m, 2H), 6.5-6.7 (m, 1H), 7.1-7.2 (d, 2H), 7.3-7.5 (m, 4H), 10.0-10.1 (d, 1H). MS (m/z): [M+H]+, 305.2.

QEA-E-002 (9-Cyclohex-1-enyl-7-(4-methoxy-phenyl)-3-methyl-nona-2,4,6,8-tetraenal)

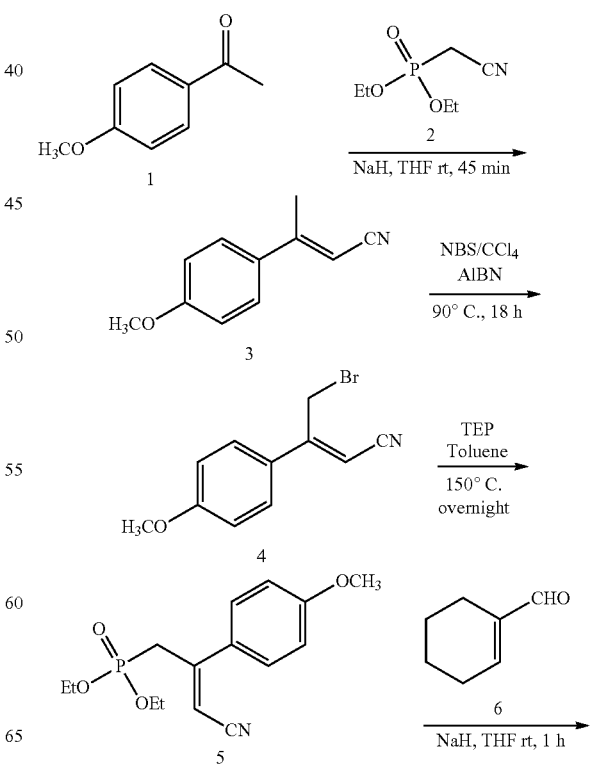

Preparation of Compound-3: To a stirred suspension of NaH (362 mg, 15 mmol) in dry THF (10 mL) at 0° C., a solution of Compound-2 (3.6 g, 12 mmol) in dry THF (10 mL) was added dropwise. The reaction mixture was stirred at 45° C. for 45 min, then a solution of Compound-1 (1.2 g, 10 mmol) in dry THF (10 mL) was slowly added and the resulting mixture was stirred at room temperature for 1 h. The reaction was quenched with a saturated $NH_4Cl$ solution and the aqueous layer was extracted twice with ethyl acetate. The combined organic layers were dried over anhydrous $Na_2SO_4$ and concentrated under reduced pressure. The crude compound was purified by column chromatography on 100-200 mesh silica gel and eluted with 0.5% ethyl acetate/petroleum ether to obtain Compound-3 (720 mg, 28%). MS (m/z): [M+H]+, 236.2.

Preparation of Compound-4: To a solution of Compound-3 (720 mg, 3.0 mmol) in dry toluene (10 mL) cooled to −70° C. under nitrogen was slowly added DIBAL-H (1.7 M in toluene, 3.5 mL) and the reaction mixture was stirred for 30 min. Then the solution was poured into a 0.3 M $H_2SO_4$ solution at 0° C. and the resulting aqueous layer was extracted twice with ethyl acetate. The combined organic layers were dried over anhydrous $Na_2SO_4$ and concentrated under vacuum. The residue was purified by column chromatography on 100-200 mesh silica gel and eluted with

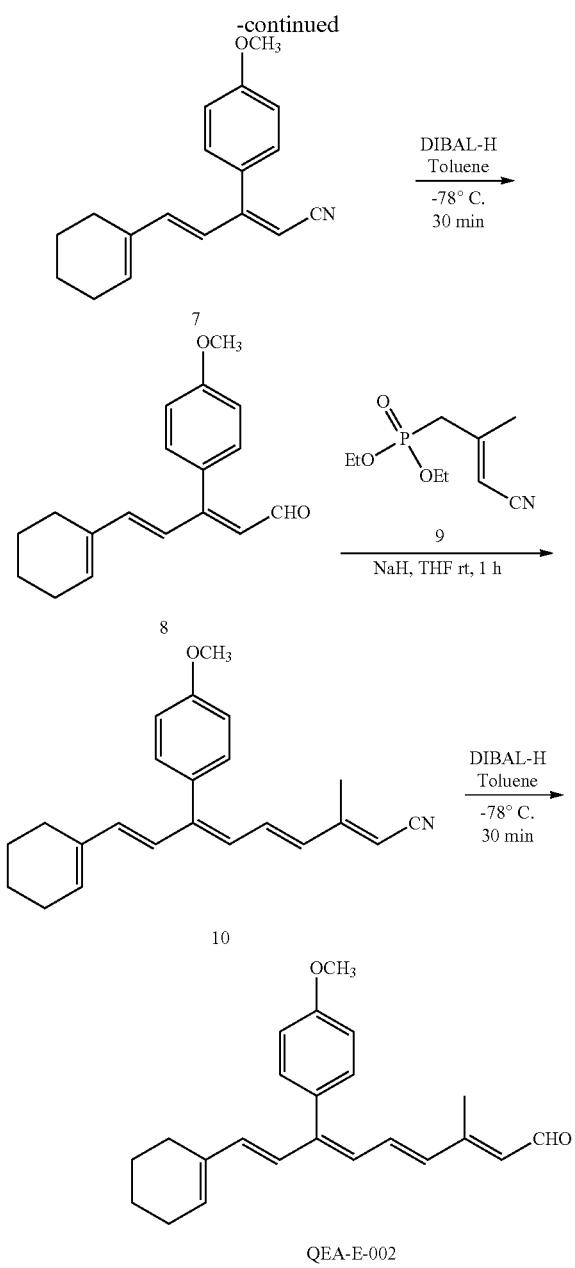

Preparation of Compound-3: To a stirred suspension of NaH (1.44 g, 59 mmol) in dry THF (10 mL) at room temperature under nitrogen was added a solution of Compound-2 (8.5 g, 47 mmol) in dry THF (10 mL). The reaction mixture was stirred at room temperature for 45 min. A solution of Compound-1 (6 g, 39 mmol) in dry THF (10 mL) was slowly added at room temperature. The resulting mixture was stirred at room temperature for 30 min. The reaction was quenched with a saturated NH$_4$Cl solution and extracted thrice with ethyl acetate. The combined organic layers were dried over anhydrous Na$_2$SO$_4$ and concentrated. The residue was purified by column chromatography on 100-200 mesh silica gel and eluted with 1% ethyl acetate/petroleum ether to obtain Compound-3 (6.8 g, 98.3%). MS (m/z): [M+H]$^+$, 174.2.

Preparation of Compound-4: To a stirred solution of Compound-3 (1 g, 5.7 mmol) in CCl$_4$ (20 mL) at room temperature was added NBS followed slowly by AIBN. The reaction mixture was stirred at 90° C. for 18 h and diluted with DCM. The mixture was washed with water (90 mL), the organic layer was dried over anhydrous Na$_2$SO$_4$ and concentrated. The residue was purified by column chromatography on 100-200 mesh silica gel and eluted with 5-8% ethyl acetate/petroleum ether to obtain compound-4 (1.1 g, 75.8%). MS (m/z): [M+H]$^+$, 253.1.

Preparation of Compound-5: To a stirred solution of Compound-4 (1.1 g, 4.3 mmol) in dry toluene (2 mL) at room temperature was slowly added triethyl phosphate (1.6 g, 6.9 mmol) and the reaction mixture was stirred at 150° C. overnight. After the excessive triethyl phosphate was evaporated, the residue was purified by column chromatography on 100-200 mesh silica gel and eluted with 40% ethyl acetate/petroleum ether to obtain Compound-5 (600 mg, 44.7%). MS (m/z): [M+H]$^+$, 310.3.

Preparation of Compound-7: To a stirred suspension of NaH (456 mg, 19 mmol) in dry THF (10 mL) at 0° C. was added dropwise a solution of Compound-5 (4.7 g, 15.2 mmol) in dry THF (10 mL). This reaction mixture was stirred at 0° C. for 30 min. A solution of Compound-6 (1.4 g, 12 mmol) in dry THF (10 mL) then was slowly added and the solution was stirred at room temperature for 1 h. The reaction was quenched with a saturated NH$_4$Cl solution, the resulting aqueous layer was extracted twice with ethyl acetate. The combined organic layers were dried over anhydrous Na$_2$SO$_4$ and concentrated under vacuum. The crude compound was purified by column chromatography on 100-200 mesh silica gel and eluted with 1% ethyl acetate/petroleum ether to obtain Compound-7 (830 mg, 24.6%). MS (m/z): [M+H]$^+$, 266.2.

Preparation of Compound-8: To a solution of Compound-7 (1 g, 3.7 mmol) in dry toluene (10 mL) cooled to −78° C. under nitrogen was slowly added DIBAL-H (1.7 M in toluene, 4.43 mL). The reaction mixture was stirred at −78° C. for 30 min and then quenched with a cold 0.3 M H$_2$SO$_4$ solution. The aqueous layer was extracted thrice with ethyl acetate. The combined organic layers were dried over anhydrous Na$_2$SO$_4$ and concentrated under vacuum. The residue was purified by column chromatography on 100-200 mesh silica gel and eluted with 1% with ethyl acetate/petroleum ether to obtain Compound-8 (640 mg, 63.3%). MS (m/z): [M+H]$^+$, 269.2

Preparation of Compound-10: To a stirred suspension of NaH (57 mg, 2.4 mmol) in dry THF (2 mL) at 0° C. under nitrogen was added a solution of Compound-9 (456 mg, 2.1 mmol) in dry THF (10 mL). The reaction mixture was stirred at room temperature for 1 h. Then a solution of Compound-8 (440 mg, 1.6 mmol) in dry THF (10 mL) was slowly added at 0° C. The resulting reaction mixture was stirred at room temperature for 1 h. the reaction was quenched with a saturated NH$_4$Cl solution, the resulting mixture was extracted thrice with ethyl acetate, dried over anhydrous Na$_2$SO$_4$ and concentrated under vacuum. The residue was purified by column chromatography on 60-120 mesh silica gel and eluted with 1% ethyl acetate/petroleum ether to obtain Compound-10 (400 mg, 73.7%). MS (m/z): [M+H]$^+$, 332.3.

Preparation of QEA-E-002: To a stirred solution of Compound-10 (400 mg, 1.1 mmol) in dry toluene (10 mL) at −78° C. under nitrogen was added drops of DIBAL-H (1.7 M in toluene, 1.42 mL). This reaction mixture was stirred at −78° C. for 30 min, and the reaction was quenched with a 3 M H$_2$SO$_4$ solution at 0° C. The solution was stirred at room temperature for 30 min. The aqueous layer was extracted thrice with ethyl acetate, and the combined organic layers were dried over anhydrous Na$_2$SO$_4$ and concentrated under vacuum. The residue was purified by column chromatography on 60-120 mesh silica gel and eluted with 0.4-0.5% ethyl acetate/petroleum ether to obtain QEA-E-002 (120 mg, 29.7%). $^1$H NMR of major isomer (CDCl$_3$, 300 MHz): δ 1.6-1.8 (m, 4H), 2.1 (s, 3H), 2.2-2.45 (m, 4H), 3.8 (s, 3H), 5.7 (s, 1H), 5.95-6.1 (m, 2H), 6.2-6.3 (m, 1H), 6.4-6.5 (m, 2H), 6.6-6.8 (m, 1H), 6.9-7.0 (d, 2H), 7.1-7.2 (d, 2H), 10.1-10.25 (d, 1H). MS (m/z): [M+H]$^+$, 335.3.

QEA-D-002 (3-Methyl-6-[3-(tetrahydro-pyran-3-yl)-cyclohex-2-enylidene]-hexa-2,4-dienal)

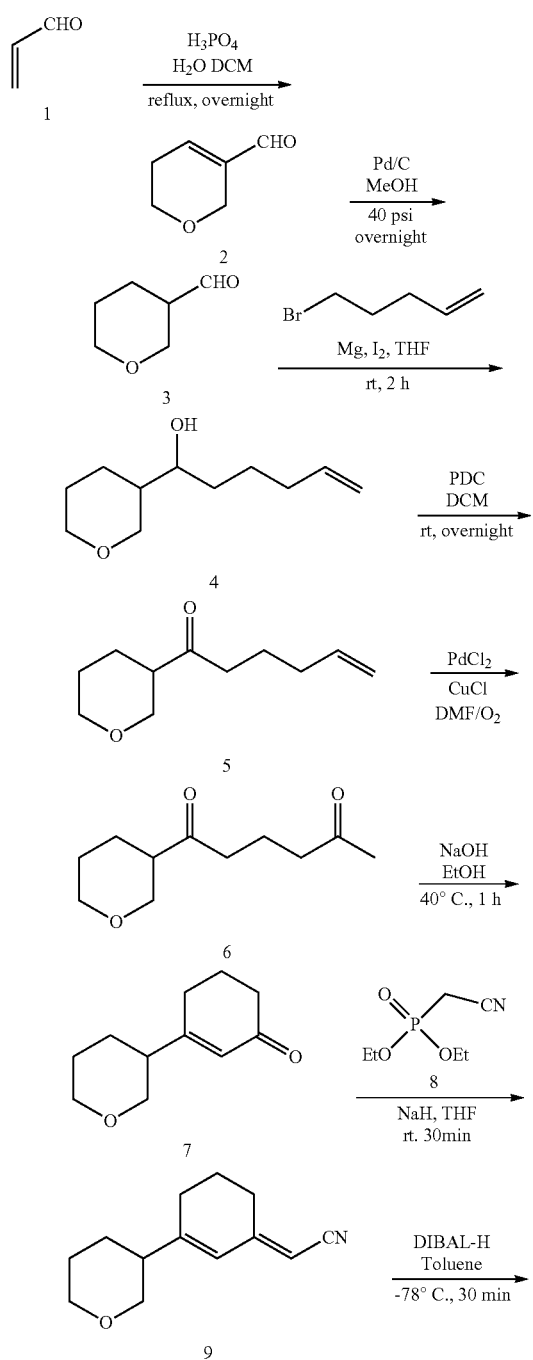

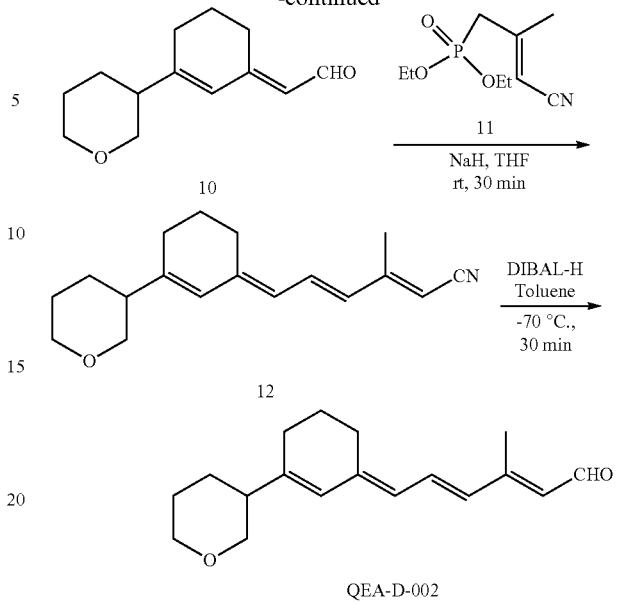

Preparation of Compound-2: To a stirred mixture of Compound-1 (40 g, 713 mmol) in DCM (105 mL) and H$_2$O (2.3 mL) at room temperature, H$_3$PO$_4$ (12.7 mL) was slowly added and the reaction mixture was refluxed overnight. The mixture was purified by fractional distillation at 110-150° C./20 mmHg to obtain Compound-2 (12.6 g, 15.7%). MS (m/z): [M+H]$^+$, 113.1.

Preparation of Compound-3: 10% Pd/C (600 mg) was slowly added to a solution of Compound-2 (6 g, 53.5 mmol) in methanol (10 mL) and the mixture was stirred under hydrogen (40 psi). The reaction mixture was filtered through celite, the precipitate was rinsed with methanol and the filtrate was concentrated under vacuum. The residue was purified by fractional distillation at 125° C./20 mm Hg to obtain Compound-3 (5.5 g, 91.6%). MS (m/z): [M+H]$^+$, 115.1.

Preparation of Compound-4: To a stirred suspension of Mg (2 g, 84 mmol) with cat. I$_2$ in dry THF (20 mL) under nitrogen was slowly added 5-bromopentene (9.9 mL, 84 mmol). The reaction was stirred for 1 h. Then Compound-3 (8 g, 70 mmol) was added at −5° C., and the reaction mixture was stirred at room temperature for 2 h. The reaction was quenched with a saturated NH$_4$Cl solution and extracted thrice with ethyl acetate. The organic layer was dried over anhydrous Na$_2$SO$_4$ and concentrated. The residue was purified by column chromatography on 60-120 mesh silica gel and eluted with 8% ethyl acetate/petroleum ether to obtain Compound-4 (9.5 g, 74.3%). MS (m/z): [M+H]$^+$, 185.1.

Preparation of Compound-5: To a stirred solution of Compound-4 (980 mg, 5.3 mmol) in DCM (10 mL) at 0° C., PDC (3.98 g, 10.6 mmol) was slowly added. The reaction mixture was stirred at room temperature overnight. The mixture then was poured onto a 60-120 mesh silica mesh, the precipitate was rinsed with ether and the filtrate was concentrated under vacuum. The residue was purified by column chromatography on 60-120 mesh silica gel and eluted with 10% ethyl acetate/petroleum ether to obtain Compound-5 (80 mg, 8.25%). MS (m/z): [M+H]$^+$, 183.1.

Preparation of Compound-6: To a stirred suspension of PdCl$_2$ (18.6 mg, 0.1 mmol), CuCl (138.6 mg, 1.4 mmol) in H$_2$O (10 mL) and DMF (10 mL) at room temperature was slowly added a solution of Compound-5 (80 mg, 0.4 mmol)

in dry DMF (16.6 mL). The reaction mixture was stirred under oxygen atmosphere for 3 h, then quenched with a 5% HCl solution and extracted thrice with ether. The combined organic layers were dried over anhydrous $Na_2SO_4$ and concentrated to obtain Compound-6 (220 mg, 64%). MS (m/z): [M+H]$^+$, 199.2.

Preparation of Compound-7: To a stirred solution of Compound-6 (3 g, 15.1 mmol) in ethanol (5 mL) and water (5 mL) at 40° C., NaOH solution (1 M, 30 mL) was slowly added and the reaction mixture was stirred at 40° C. for 1 h. The resulting aqueous layer was extracted thrice with ethyl acetate. The combined organic extracts were dried over anhydrous $Na_2SO_4$ and concentrated under reduced pressure. The residue was purified by column chromatography on 60-120 mesh silica gel and eluted with 20% ethyl acetate/petroleum ether to obtain Compound-7 (2 g, 73.3%). MS (m/z): [M+H]$^+$, 181.1.

Preparation of Compound-9: To a stirred suspension of NaH (475 mg, 19.8 mmol) in dry THF (10 mL) at 0° C. was slowly added a solution of Compound-8 (2.93 g, 16.6 mmol) in dry THF (10 mL). The reaction mixture was stirred at room temperature for 1 h until it turned into light cream color. To the reaction mixture was added a solution of Compound-7 (2 g, 11 mmol) in dry THF (10 mL) and the solution was stirred at room temperature for 30 min. The reaction was quenched with a saturated $NH_4Cl$ solution and the aqueous layer was extracted twice with ethyl acetate. The combined organic layers were dried over anhydrous $Na_2SO_4$ and concentrated under vacuum. The crude compound was purified by column chromatography on 100-200 mesh silica gel and eluted with 10% ethyl acetate/petroleum ether to obtain Compound-9 (2 g, 88.8%). MS (m/z): [M+H]$^+$, 204.2.

Preparation of Compound-10: To a stirred solution of Compound-9 (2 g, 9.8 mmol) in dry toluene (10 mL) cooled to −78° C. under nitrogen was slowly added DIBAL-H (1.7 M, 11.5 mL) and the reaction mixture was stirred at −78° C. for 30 min. The reaction was quenched with 3 M $H_2SO_4$ solution at −78° C. and stirred at room temperature for 30 min. The resulting mixture was extracted thrice with ethyl acetate, and the combined organic layers were dried over $Na_2SO_4$ and concentrated under vacuum. The crude compound was purified by column chromatography on 100-200 mesh silica gel and eluted with 20% ethyl acetate/petroleum ether to obtain Compound-10 (1.5 g, 73.9%). MS (m/z): [M+H]$^+$, 207.2.

Preparation of Compound-12: To a stirred suspension of NaH (86 mg, 3.6 mmol) in dry THF (10 mL) at room temperature was added Compound-11 (781 mg, 3.6 mmol). The reaction mixture was stirred at 50° C. for 30 min. Then Compound-10 (500 mg, 2.4 mmol) in dry THF (10 mL) was slowly added at 0° C. The resulting reaction mixture was stirred at room temperature for 30 min and the reaction was quenched with a saturated $NH_4Cl$ solution. The aqueous layer was extracted twice with ethyl acetate, and the combined organic layers were dried over anhydrous $Na_2SO_4$ and concentrated under vacuum. The crude compound was purified by column chromatography on 60-120 mesh silica gel and eluted with 10% ethyl acetate/petroleum ether to obtain Compound-12 (600 mg, 92%). MS (m/z): [M+H]$^+$, 270.3.

Preparation of QEA-D-002: To a solution of Compound-12 (500 g, 1.8 mmol) in dry toluene (10 mL) cooled to −70° C. under nitrogen was slowly added DIBAL-H (1.7 M, 2.18 mL) and the reaction mixture was stirred at −70° C. for 30 min. The reaction was quenched with 3 M $H_2SO_4$ solution at −70° C. and the mixture was stirred at room temperature for 30 min. The resulting aqueous layer was extracted thrice with ethyl acetate, and the combined organic layers were dried over $Na_2SO_4$ and concentrated under vacuum. The crude compound was purified by column chromatography on 100-200 mesh silica gel and eluted with 10% ethyl acetate/petroleum ether to obtain of QEA-D-002 (102 mg, 23.8%). $^1$H NMR (CDCl$_3$, 400 MHz): δ 1.64-1.68 (m, 2H), 1.73-1.78 (m, 1H), 1.88-1.92 (m, 1H), 2.12-2.16 (m, 1H), 2.17-2.31 (m, 1H), 2.28 (s, 3H), 2.48-2.52 (m, 1H), 3.25-3.37 (m, 2H), 3.90-3.98 (m, 2H), 5.97 (m, 3H), 6.31 (d, J=15.6 Hz, 1H), 7.07 (m, 2H), 10.09 (d, J=6 Hz, 1H); $^{13}$C NMR (CDCl$_3$, 100 MHz): δ 13.10, 22.56, 25.68, 25.91, 28.13, 28.58, 44.31, 68.30, 71.87, 125.1, 126.3, 128.7, 132.3, 133.6, 142.8, 146.4, 155.1, 191.2. MS (m/z): [M+H]$^+$, 273.3.

QEA-G-001 (3-Methyl-6-(3-pyridin-3-yl-cyclohex-2-enylidene)-hexa-2,4-dienal)

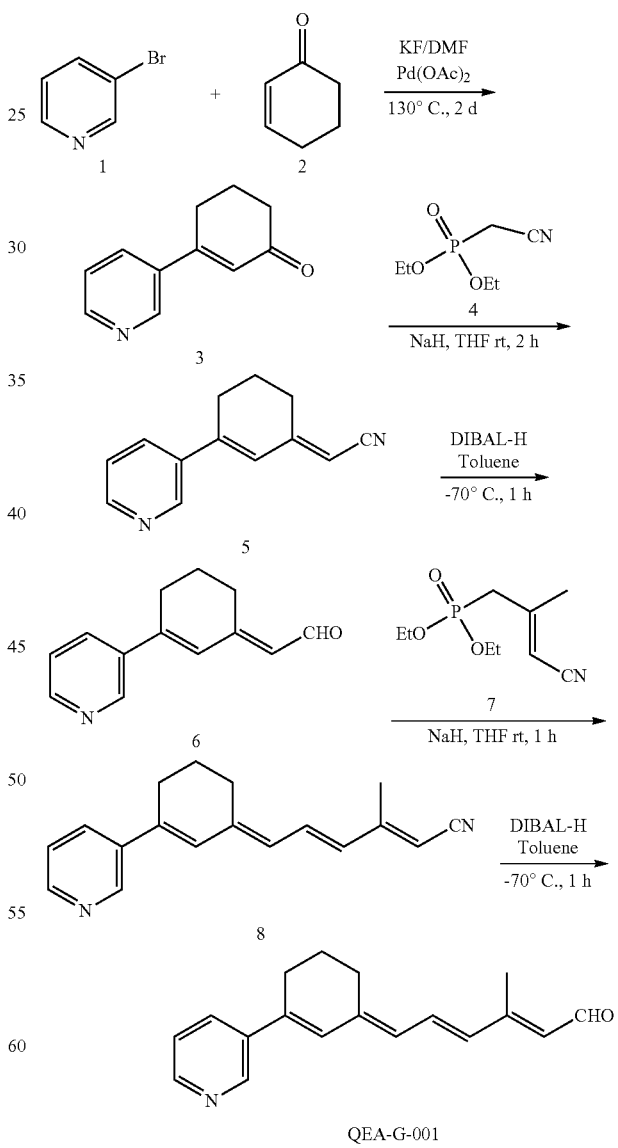

QEA-G-001

Preparation of Compound-3: To a stirred solution of Compound-1 (8 g, 50.6 mmol) in DMF (10 mL) at room temperature were added Compound-2 (9.8 mL, 101.26 mmol), KF (5.88 g, 101.26 mmol) and Pd(OAc)$_2$ (227 mg, 1.012 mmol). The reaction mixture was stirred at 130° C. for 2 d, then diluted with water and extracted with diethyl ether. The combined organic layers were dried over anhydrous Na$_2$SO$_4$ and concentrated under reduced pressure. The residue was purified by column chromatography on 100-200 mesh silica gel and eluted with ethyl acetate to obtain Compound-3 (1.8 g, 20.5%). MS (m/z): [M+H]$^+$, 174.2.

Preparation of Compound-5: To a stirred suspension of NaH (80 mg, 2.8 mmol) in dry THF (20 mL) at 10° C. was slowly added a solution of Compound-4 (380 mg, 2.1 mmol) in dry THF (10 mL). The reaction mixture was stirred at room temperature for 30 min. Then a solution of Compound-3 (250 mg, 1.4 mmol) in dry THF (10 mL) was slowly added and the resulting solution was stirred at room temperature for 2 h. The reaction was quenched with a saturated NH$_4$Cl solution. The aqueous layer was extracted twice with ethyl acetate, and the combined organic layers were dried over anhydrous Na$_2$SO$_4$ and concentrated under vacuum. The crude compound was purified by column chromatography on 100-200 mesh silica gel and eluted with 40-50% ethyl acetate/petroleum ether to obtain Compound-5 (50 mg, 17.7%). MS (m/z): [M+H]$^+$, 197.2.

Preparation of Compound-6: To a stirred solution of Compound-5 (1.18 g, 6.0 mmol) in dry toluene (10 mL) cooled to −70° C. under nitrogen was slowly added DIBAL-H (1.7 M in toluene, 7 mL) and the reaction mixture was stirred at −70° C. for 1 h. Then the solution was poured into a saturated potassium tartrate solution at 10° C. and stirred at room temperature for 1 h. The mixture was alkylinated with NaHCO$_3$, extracted with ethyl acetate, dried over anhydrous Na$_2$SO$_4$ and concentrated under vacuum. The crude compound was purified by column chromatography on neutral alumina and eluted with 15% ethyl acetate/petroleum ether to obtain of Compound-6 (330 mg, 27.5%). MS (m/z): [M+H]$^+$, 200.2.

Preparation of Compound-8: To a stirred suspension of NaH (79 mg, 3.3 mmol) in dry THF (10 mL) cooled to 10° C. was slowly added a solution of Compound-7 (719 mg, 3.3 mmol) in dry THF (10 mL). This reaction mixture was stirred at room temperature for 1 h. Then Compound-6 (330 mg, 1.6 mmol) was added at 10° C. The resulting mixture was stirred at room temperature for 1 h. The reaction was quenched with a saturated NH$_4$Cl solution, the aqueous layer was extracted twice with ethyl acetate, and the combined organic layers were dried over anhydrous Na$_2$SO$_4$ and concentrated under vacuum. The crude compound was purified by column chromatography on 60-120 mesh silica gel and eluted with 30% ethyl acetate/tet ether to obtain Compound-8 (350 mg, 80.6%). MS (m/z): [M+H]$^+$, 263.2.

Preparation of QEA-G-001: To a stirred solution of Compound-8 (350 mg, 1.33 mmol) in dry toluene (10 mL) cooled to −70° C. under nitrogen was slowly added DIBAL-H (1.7 M in toluene, 2.35 mL). The reaction mixture was stirred at −70° C. for 1 h, and then poured into a saturated sodium potassium tartrate solution at 0° C. and stirred at room temperature for 1 h, extracted with ethyl acetate, dried over Na$_2$SO$_4$ and concentrated under vacuum. The crude compound was purified by column chromatography on neutral alumina and eluted with 12-15% ethyl acetate/petroleum ether to obtain of QEA-G-001 (120 mg, 33.8%). $^1$H NMR of major isomer (CDCl$_3$, 300 MHz): δ 1.95-2.01 (m, 2H), 2.34 (s, 3H), 2.59-2.65 (m, 4H), 6.02 (d, J=8 Hz, 1H), 6.29 (d, J=12 Hz, 1H), 6.46 (d, J=11.2 Hz, 1H), 6.78 (s, 1H), 7.09 (dd, J=11.6 Hz, 15.6 Hz, 1H), 7.64 (m, 1H), 8.15 (d, J=7.6 Hz, 1H), 8.53 (bs, 1H), 8.79 (bs, 1H), 10.13 (d, J=8 Hz, 1H);

$^{13}$C NMR (CDCl$_3$, 150 MHz): δ 13.33, 22.25, 25.15, 27.38, 125.3, 130.1, 130.5, 131.3, 132.2, 135.1, 136.8, 137.1, 139.0, 140.9, 141.2, 142.2, 154.1, 191.2. MS (m/z): [M+H]+, 266.2.

QEA-C-006 (Acetic acid 4-[3-(4-methoxy-phenyl)-7-methyl-9-oxo-nona-1,3,5,7-tetraenyl]-phenyl ester)

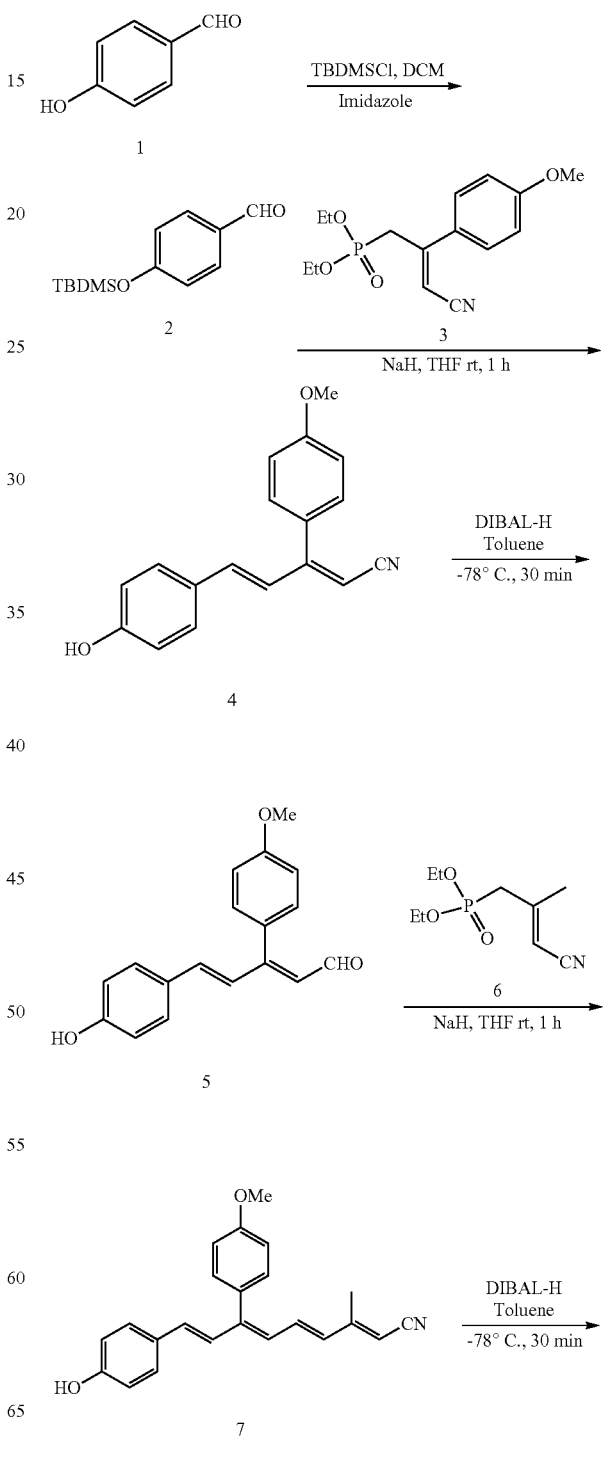

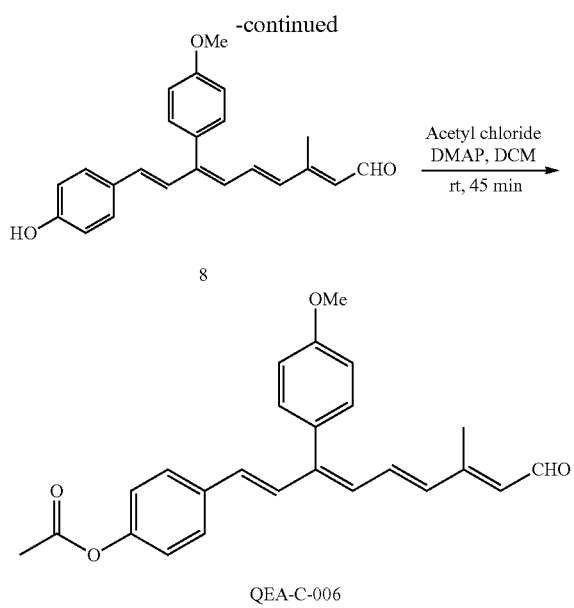

Preparation of Compound-2: To a stirred solution of Compound-1 (10 g, 81.8 mmol) in DCM (10 mL) at 0° C. was slowly added TBDMSCl (24.66 g, 163.6 mmol). Then the reaction was quenched with water and the aqueous layer was extracted thrice with DCM. The combined organic layer was washed with brine, dried over anhydrous $Na_2SO_4$ and concentrated under vacuum. The crude compound was purified by column chromatography on 60-120 mesh silica gel and eluted with 5% ethyl acetate/petroleum ether to obtain Compound-2 (11 g, 56.8%). MS (m/z): $[M+H]^+$, 237.2.

Preparation of Compound-4: To a stirred suspension of NaH (1.56 g, 65 mmol) in dry THF (10 mL) at room temperature under nitrogen was added dropwise a solution of Compound-3 (17.2 g, 55.6 mmol) in dry THF (10 mL). The reaction mixture was stirred at room temperature for 30 min. Then a solution of Compound-2 (11 g, 46.5 mmol) in dry THF (10 mL) was slowly added and the resulting reaction mixture was stirred at room temperature for 1 h. The reaction was quenched with a saturated with $NH_4Cl$ solution and the aqueous layer was extracted thrice with ethyl acetate. The combined organic layers were dried over anhydrous $Na_2SO_4$ and concentrated under vacuum. The crude compound was purified by column chromatography on 60-120 mesh silica gel and eluted with 10% ethyl acetate/petroleum ether to obtain Compound-4 (3.5 g, 27%). MS (m/z): $[M+H]^+$, 278.2.

Preparation of Compound-5: To a solution of Compound-4 (3.5 g, 12.6 mmol) in toluene/DCM (4:1) cooled to −78° C. under nitrogen was slowly added DIBAL-H (1.7 M in toluene, 25.9 mL) and the reaction mixture was stirred for 30 min. The reaction was quenched with a saturated $NH_4Cl$ solution and the aqueous layer was extracted thrice with ethyl acetate. The combined organic layers were dried over anhydrous $Na_2SO_4$ and concentrated. The residue was purified by column chromatography on 60-120 mesh silica gel and eluted with 30% ethyl acetate/petroleum ether to obtain compound-5 (1.5 g, 42.4%). MS (m/z): $[M+H]^+$, 281.2.

Preparation of Compound-7: To a stirred suspension of NaH (0.3 g, 2.5 mmol) in dry THF (10 mL) at room temperature under nitrogen was added dropwise a solution of Compound-6 (1.62 g, 7.5 mmol) in dry THF (10 mL). The reaction mixture was stirred at room temperature for 30 min. A solution of Compound-5 (1.4 g, 5 mmol) in dry THF (10 mL) was slowly added and the solution was stirred at room temperature for 1 h. The reaction was quenched with a saturated $NH_4Cl$ solution and the aqueous layer was extracted thrice with ethyl acetate. The combined organic layers were dried over anhydrous $Na_2SO_4$ and concentrated under vacuum. The crude compound was purified by column chromatography on 60-120 mesh silica gel and eluted with 15% ethyl acetate/petroleum ether to obtain Compound-7 (1.6 g, 93.2%). MS (m/z): $[M+H]^+$, 344.3.

Preparation of Compound-8: To a solution of Compound-7 (1.6 g, 4.65 mmol) in mixture of toluene (5 mL) and DCM (5 mL) cooled to −70° C. under nitrogen was slowly added DIBAL-H (1.7 M in toluene, 9.6 mL) and the reaction mixture was stirred for 1 h. The reaction was quenched with a 0.3 M $H_2SO_4$ solution and the aqueous layer was extracted with ethyl acetate. The combined organic layers were dried over anhydrous $Na_2SO_4$ and evaporated under vacuum. The residue was purified by column chromatography on 100-200 mesh silica gel and eluted with 12% ethyl acetate/petroleum ether to obtain Compound-8 (1 g, 62%). MS (m/z): $[M+H]^+$, 347.3.

Preparation of QEA-C-006: To a stirred solution of compound-7 (1 g, 2.8 mmol) in DCM at 0° C. under nitrogen was added DMAP (512 mg, 4.2 mmol) followed by acetyl chloride (329 mg, 4.2 mmol). The reaction mixture was stirred at room temperature for 45 min, diluted with water, extracted thrice with ethyl acetate. The combined organic layers were dried over anhydrous $Na_2SO_4$ and concentrated under vacuum. The residue was purified by column chromatography on 100-200 mesh silica gel and eluted with 1% ethyl acetate/petroleum ether to obtain QEA-C-006 (330 mg, 29.4%). $^1$H NMR ($CDCl_3$, 400 MHz): δ 2.11 (d, J=1.2 Hz, 3H), 2.29 (s, 3H), 3.89 (s, 3H), 5.95 (d, J=8 Hz, 1H), 6.31 (d, J=16 Hz, 1H), 6.44 (d, J=15.2 Hz, 1H), 6.53 (d, J=11.2 Hz, 1H), 6.55-6.69 (m, 1H), 6.71 (dd, J=11.2 Hz, 15.2 Hz, 1H), 6.98-7.05 (m, 4H), 7.16 (d, J=8.8 Hz, 2H), 7.37 (d, J=11.2 Hz, 2H), 10.06 (d, J=8.4 Hz, 1H); $^{13}$C NMR ($CDCl_3$, 100 MHz): δ 13.28, 21.39, 55.53, 114.0, 122.1, 127.9, 129.1, 129.6, 131.3, 131.8, 132.8, 133.0, 134.2, 135.1, 136.0, 146.9, 150.5, 154.9, 159.5, 169.7, 191.4. MS (m/z): $[M+H]^+$, 389.3.

QEA-C-005 (7-(4-Methoxy-phenyl)-3-methyl-9-(4-nitro-phenyl)-nona-2,4,6,8-tetraenal)

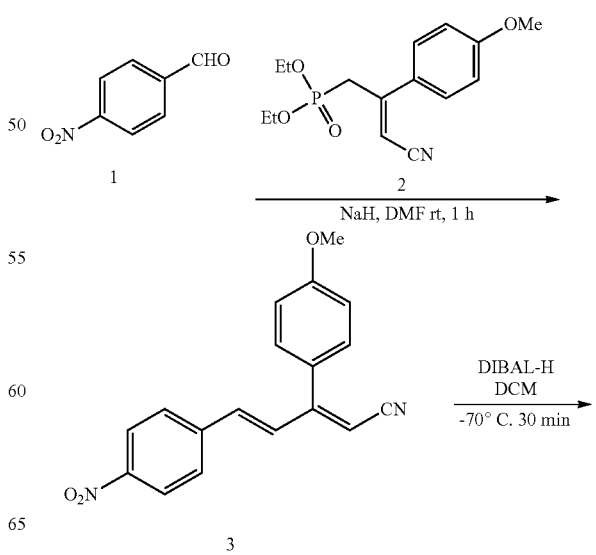

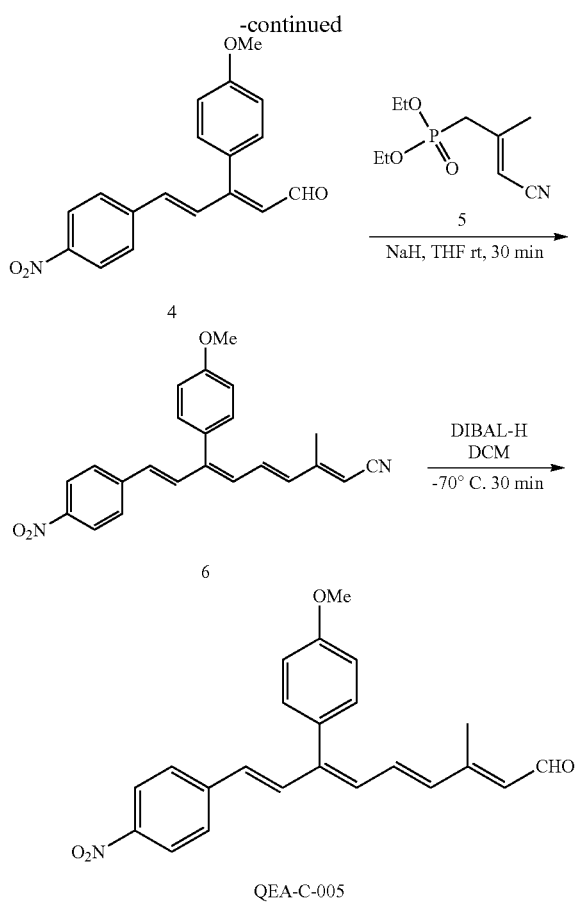

Preparation of Compound-3: To a suspension of NaH (633 mg, 26.4 mmol) in dry DMF (10 mL) cooled to 0° C. under nitrogen was added dropwise a solution of Compound-2 (6.12 g, 19.8 mmol) in dry DMF (10 mL). The reaction mixture was stirred at room temperature for 30 min. To the reaction mixture was slowly added a solution of Compound-1 (2 g, 13.2 mmol) in dry DMF (10 mL) at 10° C. and the resulting mixture was stirred at room temperature for 10 min. The reaction was quenched with a saturated NH$_4$Cl solution. The aqueous layer was extracted with ethyl acetate, and the combined organic layers were dried over anhydrous Na$_2$SO$_4$ and concentrated under vacuum. The crude compound was purified by column chromatography on 60-120 mesh silica gel and eluted with 10% ethyl acetate/petroleum ether to obtain Compound-3 (2.5 g, 62%). MS (m/z): [M+H]$^+$, 307.3.

Preparation of Compound-4: To a solution of Compound-3 (2.18 g, 7.1 mmol) in DCM (5 mL) cooled to −70° C. under nitrogen was slowly added DIBAL-H (1.7 M in toluene, 8.4 mL) and the reaction mixture was stirred at for 30 min. The reaction was quenched with a 0.3 M H$_2$SO$_4$ solution and stirred at room temperature for 30 min. The mixture was extracted thrice with ethyl acetate, and the combined organic layers were dried over Na$_2$SO$_4$ and concentrated under vacuum. The residue was purified by column chromatography on 60-120 mesh silica gel and eluted with 13-15% ethyl acetate/petroleum ether to obtain Compound-4 (1 g, 45.4%). MS (m/z): [M+H]$^+$, 310.2.

Preparation of Compound-6: To a stirred suspension of NaH (115 mg, 4.8 mmol) in dry THF (10 mL) at room temperature under nitrogen was added dropwise a solution of Compound-5 (825 mg, 3.8 mmol) in dry THF (10 mL). The reaction mixture was stirred at room temperature for 30 min. Then a solution of Compound-4 (1 g, 3.2 mmol) in dry THF (10 mL) was slowly added and the solution was stirred at room temperature for 30 min. The reaction was quenched with a saturated NH$_4$Cl solution and the aqueous layer was extracted thrice with ethyl acetate. The combined organic layers were dried over anhydrous Na$_2$SO$_4$ and concentrated under vacuum. The crude compound was purified by column chromatography on 100-200 mesh silica gel and eluted with 8-10% ethyl acetate/petroleum ether to obtain Compound-6 (1.09 g, 90.8%). MS (m/z): [M+H]$^+$, 373.3.

Preparation of QEA-C-005: To a solution of Compound-6 (1.09 g, 2.9 mmol) dissolved in mixture of toluene (10 mL) and DCM (5 mL) cooled to −70° C. under nitrogen was added dropwise DIBAL-H (1.7 M in toluene, 3.44 mL). The reaction mixture was stirred at −70° C. for 30 min and then poured into a 0.3 M H$_2$SO$_4$ solution at 0° C. The reaction mixture was stirred at room temperature for 30 min, extracted thrice with ethyl acetate. The combined organic layers were dried over Na$_2$SO$_4$ and concentrated under vacuum. The residue was purified by column chromatography on 100-200 mesh silica gel and eluted with 10-12% ethyl acetate/petroleum ether to obtain QEA-C-005 (700 mg, 63.7%). $^1$H NMR of major isomer (CDCl$_3$, 400 MHz): δ 2.12 (s, 3H), 3.91 (s, 3H), 5.99 (d, J=8 Hz, 1H), 6.36 (d, J=16 Hz, 1H), 6.51 (d, J=14.8 Hz, 1H), 6.64-6.72 (m, 2H), 7.02 (dd, J=6.4 Hz, 2 Hz, 2H), 7.17 (dd, J=8.4 Hz, 2 Hz, 2H), 7.48 (d, J=9.2 Hz, 2H), 7.48 (m, 1H), 8.16 (d, J=8.8 Hz, 2H), 10.07 (d, J=8 Hz, 1H); $^{13}$C NMR (CDCl$_3$, 100 MHz): δ 13.27, 55.55, 114.2, 114.3, 124.3, 127.2, 130.2, 131.2, 143.8, 145.9, 154.3, 159.7, 133.5, 134.3, 137.0, 137.6, 191.3. MS (m/z): [M+H]$^+$, 376.3.

QEA-G-002 (7-(4-Methoxy-phenyl)-3-methyl-9-pyridin-3-yl-nona-2,4,6,8-tetraenal)

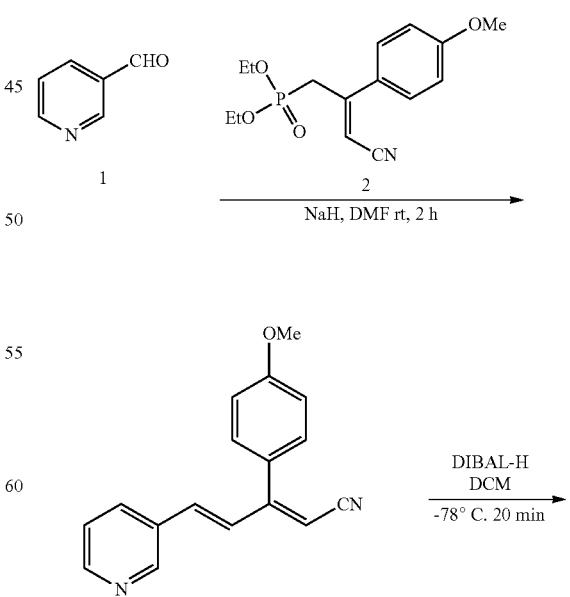

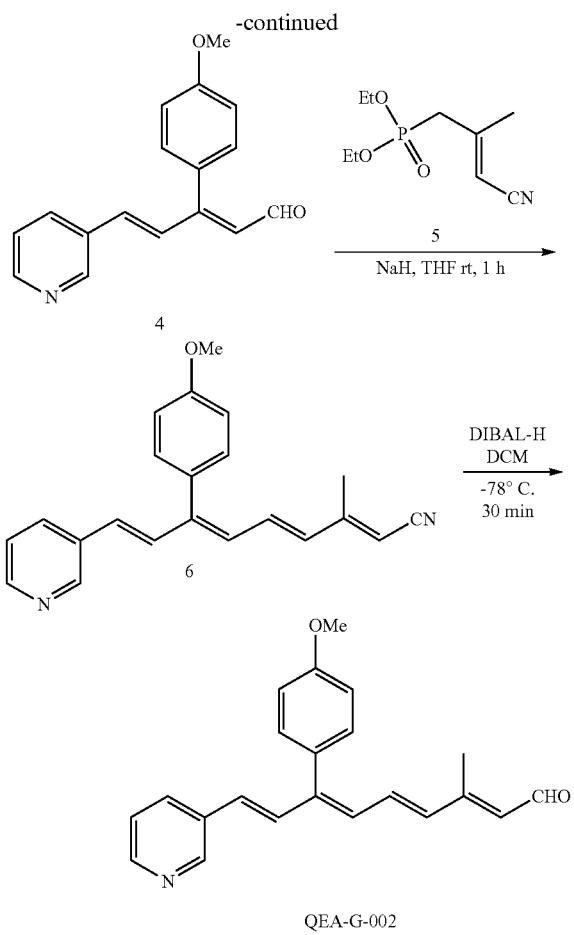

QEA-G-002

Preparation of Compound-3: To a stirred suspension of NaH (892 mg, 37.2 mmol) in dry DMF (10 mL) at 0° C. under nitrogen was added dropwise a solution of Compound-2 (6.89 g, 22.3 mmol) in dry DMF (10 mL). The reaction mixture was stirred at room temperature for 1 h. Then a solution of Compound-1 (2 g, 18.6 mmol) in dry THF (10 mL) was slowly added at 10° C. and the solution was stirred at room temperature for 2 h. The reaction was quenched with a saturated NH₄Cl solution and the aqueous layer was extracted thrice with ethyl acetate. The combined organic layers were dried over anhydrous Na₂SO₄ and concentrated under vacuum. The crude compound was purified by column chromatography on 60-120 mesh silica gel and eluted with 50% ethyl acetate/petroleum ether to obtain Compound-3 (4.5 g, 91.8%). MS (m/z): [M+H]⁺, 263.1.

Preparation of Compound-4: To a solution of Compound-3 (3.8 g, 14.4 mmol) in DCM (10 mL) cooled to −78° C. under nitrogen was slowly added DIBAL-H (1.7 M in toluene, 17 mL) and the reaction mixture was stirred for 20 min. Then the reaction was quenched with a saturated potassium sodium tartrate solution. The mixture was stirred at room temperature for 1 h. The resulting aqueous layer was extracted thrice with ethyl acetate. The combined organic layers were dried over anhydrous Na₂SO₄ and concentrated under vacuum. The residue was purified by column chromatography on 100-200 mesh silica gel and eluted with 40% ethyl acetate/petroleum ether to obtain Compound-4 (950 mg, 25%). MS (m/z): [M+H]+, 266.2.

Preparation of Compound-6: To a stirred suspension of NaH (261.8 mg, 55%, 6 mmol) in dry THF (10 mL) at room temperature under nitrogen was added dropwise a solution of Compound-5 (653 mg, 3 mmol) in dry THF (10 mL). The reaction mixture was stirred at room temperature for 30 min. A solution of Compound-4 (800 mg, 3.01 mmol) in dry THF (10 mL) was slowly added and the mixture was stirred at room temperature for 1 h. The reaction was quenched with a saturated NH₄Cl solution and the aqueous layer was extracted thrice with ethyl acetate. The combined organic layers were dried over anhydrous Na₂SO₄ and concentrated under vacuum. The crude compound was purified by column chromatography on 100-200 mesh silica gel and eluted with 25% ethyl acetate/petroleum ether to obtain Compound-6 (500 mg, 50.5%). MS (m/z): [M+H]+, 329.2.

Preparation of QEA-G-002: To a stirred solution of Compound-6 (1.2 g, 3.65 mmol) in dry toluene (10 mL) cooled to −70° C. under nitrogen was added dropwise DIBAL-H (1.7 M in toluene, 4.3 mL). The reaction mixture was stirred at −70° C. for 30 min, and then the reaction was quenched with a potassium sodium tartrate solution at 0° C. The resulting mixture was stirred for at room temperature for 30 min and extracted thrice with ethyl acetate. The combined organic layers were dried over Na₂SO₄ and concentrated. The residue was purified by column chromatography on 100-200 mesh silica gel and eluted with 1% ethyl acetate/petroleum ether to obtain QEA-G-002 (210 mg, 17.3%). ¹H NMR of major isomer (CDCl₃, 300 MHz): δ 2.09 (s, 3H), 3.90 (s, 3H), 5.98 (d, J=8 Hz, 1H), 6.30 (d, J=15.6 Hz, 1H), 6.50 (d, J=14.8 Hz, 1H), 6.58-6.71 (m, 2H), 6.99-7.03 (m, 2H), 7.15-7.19 (m, 3H), 7.38-7.43 (m, 1H), 7.87 (dd, J=2 Hz, 8.4 Hz, 1H), 8.46 (d, J=5.2 Hz, 1H), 8.61 (s, 1H), 10.07 (d, J=8.4 Hz, 1H); ¹³C NMR (CDCl₃, 150 MHz): δ 13.27, 55.54, 114.2, 124.6, 128.3, 128.7, 129.2, 130.1, 131.1, 133.5, 133.8, 134.4, 135.3, 136.0, 137.4, 145.7, 145.9, 154.3, 159.7, 191.3. MS (m/z): [M+H]⁺, 332.2.

QEA-C-004 (9-(4-Chloro-phenyl)-3-methyl-7-phenyl-nona-2,4,6,8-tetraenal)

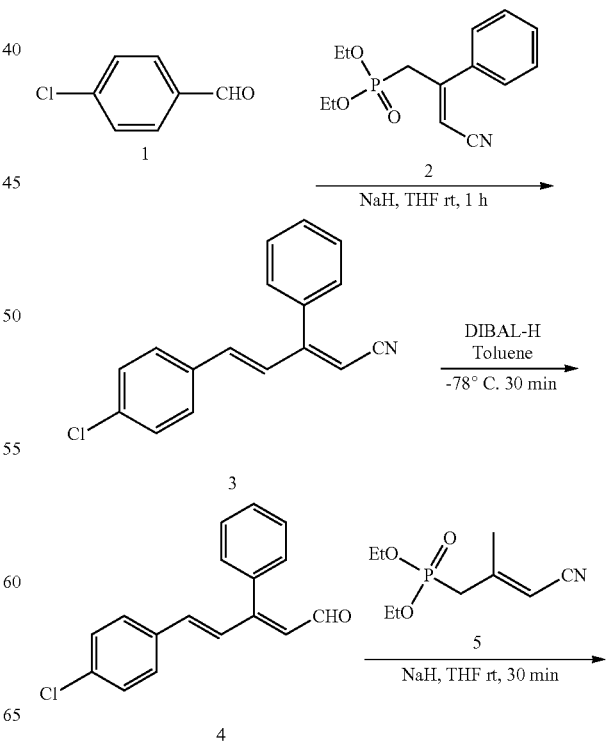

-continued

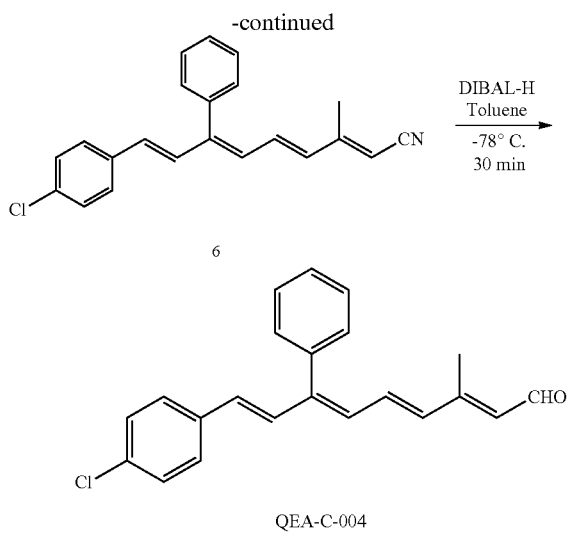

Preparation of Compound-3: To a stirred suspension of NaH (715 mg, 29.8 mmol) in dry THF (10 mL) at room temperature under nitrogen was added dropwise a solution of Compound-2 (7.1 g, 25 mmol) in dry THF (10 mL). The reaction mixture was stirred at room temperature for 40 min Then a solution of Compound-1 (3 g, 21.3 mmol) in dry THF (10 mL) was slowly added at 0° C. and the mixture was stirred at room temperature for 1 h. Then the reaction was quenched with a saturated NH$_4$Cl solution and the aqueous layer was extracted thrice with ethyl acetate. The combined organic layers were dried over anhydrous Na$_2$SO$_4$ and concentrated under vacuum. The crude compound was purified by column chromatography on 100-200 mesh silica gel and eluted with 1% ethyl acetate/petroleum ether to obtain Compound-3 (2 g, 35.2%). MS (m/z): [M+H]$^+$, 266.1.

Preparation of Compound-4: To a solution of Compound-3 (2 g, 7.5 mmol) in toluene (20 mL) cooled to −78° C. under nitrogen was slowly added DIBAL-H (1.7 M in toluene, 8.8 mL) and the reaction mixture was stirred for 30 min. The reaction was quenched with a saturated potassium sodium tartrate solution at −70° C. The resulting mixture was stirred at room temperature for 1 h. and extracted thrice with ethyl acetate. The combined organic layers were dried over anhydrous Na$_2$SO$_4$ and concentrated under vacuum. The residue was purified by column chromatography on 60-120 mesh silica gel and eluted with 1% ethyl acetate/petroleum ether to obtain Compound-4 (1.6 g, 79.2%). MS (m/z): [M+H]$^+$, 269.1.

Preparation of Compound-6: To a stirred suspension of NaH (132 mg, 5.5 mmol) in dry THF (10 mL) at room temperature under nitrogen was added dropwise a solution of Compound-5 (955 mg, 4.4 mmol) in dry THF (10 mL). This reaction mixture was stirred at room temperature for 20 min. Then a solution of Compound-4 (1 g, 3.7 mmol) in dry THF (10 mL) was slowly added and the reaction was stirred at room temperature for 30 min. The reaction mixture was quenched with a saturated NH$_4$Cl solution and the aqueous layer was extracted thrice with ethyl acetate. The combined organic layers were dried over anhydrous Na$_2$SO$_4$ and concentrated under vacuum. The crude compound was purified by column chromatography on 100-200 mesh silica gel and eluted with 1% ethyl acetate/petroleum ether to obtain Compound-6 (430 mg, 35%). IR: 2206 cm$^{-1}$. MS (m/z): [M+H]$^+$, 332.1.

Preparation of QEA-C-004: To a stirred solution of Compound-6 (580 mg, 1.74 mmol) in dry toluene at −78° C. under nitrogen was added dropwise DIBAL-H (1.7 M in toluene, 4.3 mL). The reaction mixture was stirred at −78° C. for 30 min and then poured into a 0.3 M H$_2$SO$_4$ solution at 0° C. The reaction mixture was quenched with a potassium sodium tartrate solution at 0° C. The mixture was stirred at room temperature for 30 min, and extracted thrice with ethyl acetate. The combined organic layers were dried over Na$_2$SO$_4$ and concentrated under vacuum. The residue was purified by column chromatography on 100-200 mesh silica gel and eluted with 1% ethyl acetate/petroleum ether to obtain QEA-C-004 (210 mg, 36%). $^1$H NMR of major isomer (CDCl$_3$, 400 MHz): δ 2.08 (d, J=1.2 Hz, 3H), 5.96 (d, J=8 Hz, 1H), 6.23 (d, J=15.6 Hz, 1H), 6.46 (d, J=14.8 Hz, 1H), 6.54-6.65 (m, 2H), 7.05 (d, J=15.6 Hz, 1H), 7.23-7.30 (m, 6H), 7.43-7.48 (m, 3H). 10.05 (d, J=8 Hz, 1H); $^{13}$C NMR (CDCl$_3$, 150 MHz): δ 13.20, 128.1, 128.2, 128.7, 129.1, 129.8, 130.0, 132.2, 132.7, 132.9, 133.8, 135.7, 136.5, 136.9, 147.0, 154.7, 191.4. MS (m/z): [M+H]+, 335.2.

TEA-C-002 (3,8,8-Trimethyl-7-naphthalen-2-yl-nona-2,4,6-trienal)

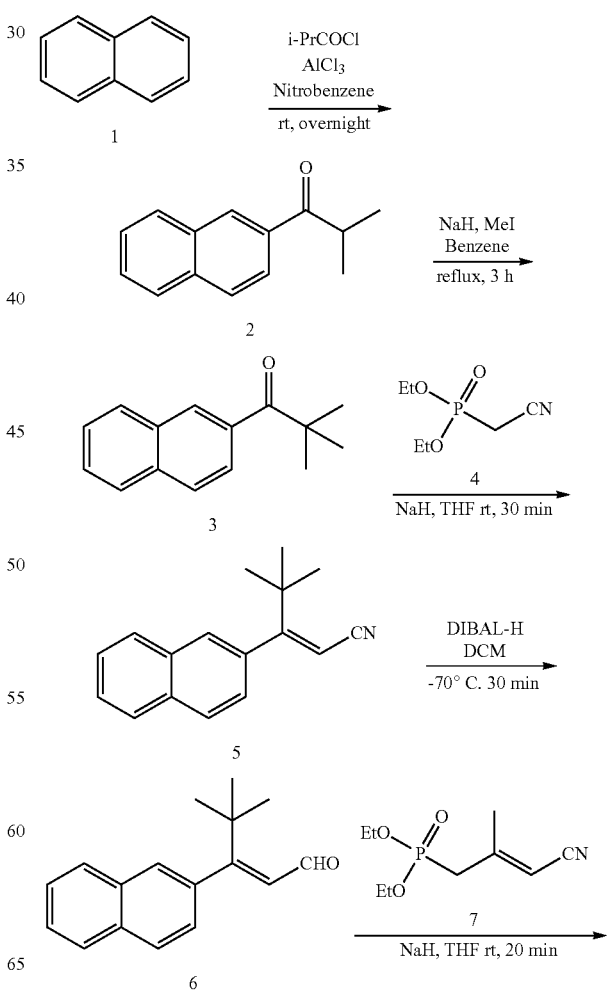

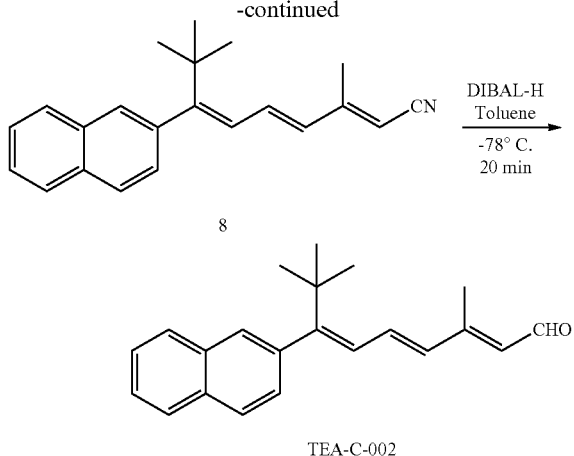

Preparation of Compound-2: To a stirred solution of nitrobenzene (23 mL) and AlCl₃ at room temperature were slowly added Compound-1 (10 g, 78 mmol) and a solution of isobutyryl chloride (9.3 mL, 88 mmol) in nitrobenzene (20 mL) at 40° C. This reaction mixture was stirred at room temperature overnight and then poured into a diluted HCl solution. The resulting white precipitate was removed by filtration. The filtrate was extracted thrice with diethyl ether, and the combined organic layers were dried over anhydrous Na₂SO₄ and concentrated under vacuum. The crude compound was purified by column chromatography on 100-200 mesh silica gel 1 and eluted with 2-5% ethyl acetate/petroleum ether to obtain Compound-3 (10 g, 64.6%). MS (m/z): [M+H]⁺, 199.1.

Preparation of Compound-3: To a stirred solution of Compound-2 (3 g, 15.1 mmol) in benzene (8.4 mL) was added NaH (1.3 g, 60%, 30.2 mmol) and the resulting solution was refluxed for 3 h. Then CH₃I (3.7 mL, 59 mmol) was slowly added at 0° C. The reaction mixture was refluxed for 3 h. The reaction mixture was quenched with 2 M HCl solution at 0° C. The aqueous layer was extracted thrice with ethyl acetate. The combined organic layers were dried over Na₂SO₄ and concentrated. The residue was purified by column chromatography on 100-200 mesh silica gel and eluted with 1% ethyl acetate/petroleum ether to obtain compound-4 (2.5 g, 78%). MS (m/z): [M+H]⁺, 213.1.

Preparation of Compound-5: To a stirred suspension of NaH (444 mg, 18.5 mmol) in dry THF (10 mL) at room temperature was added dropwise a solution of Compound-4 (3.3 g, 18.5 mmol) in dry THF (10 mL). The reaction mixture was refluxed for 30 min. A solution of Compound-3 (2.2 g, 10.3 mmol) in dry THF (10 mL) was slowly added at 0° C. and the solution was stirred at room temperature for 30 min. The reaction was quenched with a saturated NH₄Cl solution and the aqueous layer was extracted thrice with ethyl acetate. The combined organic layers were dried over anhydrous Na₂SO₄ and concentrated under vacuum. The crude compound was purified by column chromatography on 60-120 mesh silica gel and eluted with 0.5% ethyl acetate/petroleum ether to obtain Compound-5 (650 mg, 26.8%). IR: 2218 cm⁻¹. MS (m/z): [M+H]⁺, 236.2.

Preparation of Compound-6: To a stirred solution of Compound-5 (650 mg, 2.68 mmol) in DCM (10 mL) at −70° C. under nitrogen was added dropwise DIBAL-H (1.7 M in toluene, 3.25 mL). The reaction mixture was stirred at −70° C. for 30 min and the reaction was quenched with a saturated potassium sodium tartrate solution at −70° C. The mixture was stirred at room temperature for 30 min and extracted thrice with ethyl acetate. The combined organic layers were dried over Na₂SO₄ and concentrated under vacuum. The residue was purified by column chromatography on 100-200 mesh silica gel and eluted with 1% ethyl acetate/petroleum ether to obtain Compound-6 (480 mg, 73%). MS (m/z): [M+H]⁺, 239.2.

Preparation of Compound-8: To a stirred suspension of NaH (96 mg, 4 mmol) in dry THF (10 mL) at room temperature was added dropwise a solution of Compound-7 (868 mg, 3.5 mmol) in dry THF (10 mL). The reaction mixture was stirred at room temperature for 20 min. Then a solution of Compound-6 (480 mg, 2.0 mmol) in dry THF (10 mL) was slowly added and the solution was stirred at room temperature for 30 min. The reaction was quenched with a saturated NH₄Cl solution and the aqueous layer was extracted thrice with ethyl acetate. The combined organic layers were dried over anhydrous Na₂SO₄ and concentrated under vacuum. The crude compound was purified by column chromatography on 60-120 mesh silica gel and eluted with 1% ethyl acetate/petroleum ether to obtain Compound-8 (480 mg, 79%). IR: 2208 cm⁻¹. MS (m/z): [M+H]⁺, 302.2.

Preparation of TEA-C-002: To a stirred solution of Compound-8 (480 mg, 1.59 mmol) in dry toluene at −78° C. under nitrogen was added dropwise DIBAL-H (1.7 M in toluene, 1.87 mL). The reaction mixture was stirred at −78° C. for 20 min. The reaction was quenched with a saturated potassium sodium tartrate solution at 0° C. The resulting mixture was stirred at room temperature for 30 min, and then extracted thrice with ethyl acetate. The combined organic layers were dried over Na₂SO₄ and concentrated under vacuum. The residue was purified by column chromatography on 100-200 mesh silica gel and eluted with 1% ethyl acetate/petroleum ether to obtain TEA-C-002 (110 mg, 22.8%). ¹H NMR (CDCl₃, 400 MHz): δ 1.18 (s, 9H), 1.88 (s, 3H), 5.89 (d, J=8.4 Hz, 1H), 6.18-6.45 (m, 2H), 6.46 (d, J=14.4 Hz, 1H), 7.20 (dd, J=1.6 Hz, 8.4 Hz, 1H), 7.53 (m, 3H), 7.86 (m, 3H), 9.98 (d, J=8 Hz, 1H); ¹³C NMR (CDCl₃, 100 MHz): δ 13.17, 29.88, 37.34, 125.0, 126.1, 126.4, 127.4, 127.9, 128.2, 128.5, 129.2, 132.5, 133.0, 134.5, 135.0, 135.9, 137.2, 155.4, 159.1, 191.5. MS (m/z): [M+H]⁺, 305.2.

QEA-B-002 (7-tert-Butyl-3-methyl-9-(2-methyl-cyclohex-1-enyl)-nona-2,4,6,8-tetraenal)

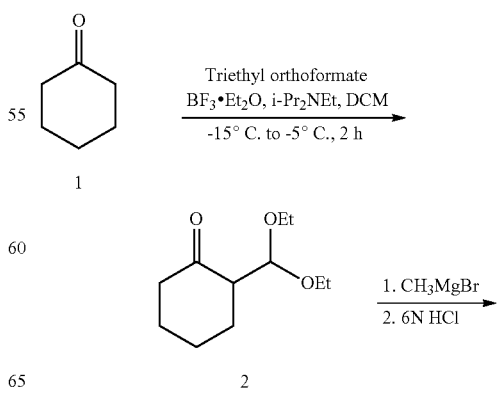

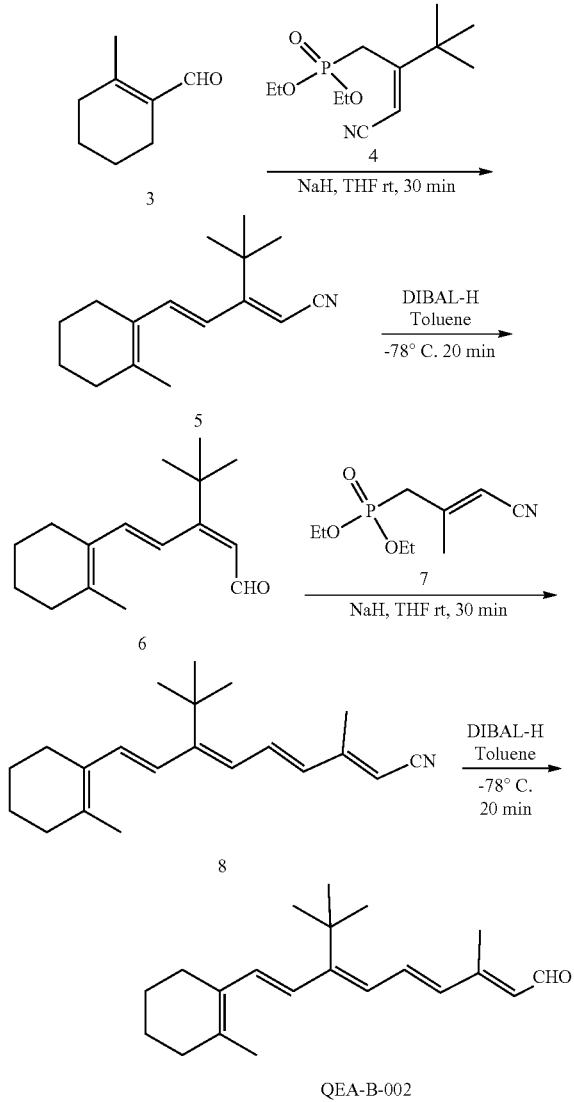

Preparation of Compound-2: To a solution of DCM (10 mL) and triethyl orthoformate (60.3 g, 407.4 mmol) cooled to −35° C. was added dropwise a solution of BF$_3$·Et$_2$O (69 g, 488 mmol) in DCM (10 mL) over a period of 30 min. The reaction mixture was stirred at room temperature for 15 min. Compound-1 (20 g, 204 mmol) and diisopropylethyl amine (79 g, 611.1 mmol) were slowly added to the reaction mixture over a period of 30 min at −78° C. Then the reaction mixture was warmed to −15° C. and stirred at −15° C. to −5° C. for 2 h. The reaction was quenched with aqueous NaHCO$_3$. The aqueous layer was extracted thrice with DCM. The combined organic layers were washed with brine, dried over anhydrous Na$_2$SO$_4$ and concentrated under vacuum. The crude compound was purified by column chromatography on 100-200 mesh silica gel and eluted with petroleum ether to obtain Compound-2 (9 g, 22%). MS (m/z): [M+H]$^+$, 201.1.

Preparation of Compound-3: To a solution of Compound-2 (9 g, 44.9 mmol) in diethyl ether (10 mL) cooled to 0° C. under nitrogen was slowly added CH$_3$MgBr (3 M in diethyl ether, 59.9 mL). The reaction mixture was stirred at 0° C. for 1 h and then at room temperature overnight. The reaction was quenched with 6 M HCl and the solution was stirred at room temperature for 3 h. The aqueous layer was extracted twice with ethyl acetate. The combined organic layers were dried over anhydrous Na$_2$SO$_4$ and concentrated under vacuum. The residue was purified by column chromatography on 60-120 mesh silica gel and eluted with 2-5% ethyl acetate/petroleum ether to obtain compound-3 (2.5 g, 44.8%). MS (m/z): [M+H]$^+$, 125.1.

Preparation of Compound-5: To a stirred suspension of NaH (1.76 g, 55%, 40.4 mmol) in dry THF (10 mL) at room temperature under nitrogen was added dropwise a solution of Compound-4 (6.27 g, 24.2 mmol) in dry THF (10 mL). The reaction mixture was stirred at room temperature for 30 min. Then a solution of Compound-3 (2.52 g, 20.2 mmol) in dry THF (10 mL) was slowly added and the mixture was stirred at room temperature for 20 min. The reaction was quenched with a saturated NH$_4$Cl solution and the aqueous layer was extracted thrice with ethyl acetate. The combined organic layers were dried over anhydrous Na$_2$SO$_4$ and concentrated under vacuum. The crude compound was purified by column chromatography on 60-120 mesh silica gel and eluted with 0.5% ethyl acetate/petroleum ether to obtain Compound-5 (3.3 g, 70.9%). MS (m/z): [M+H]$^+$, 230.1.

Preparation of Compound-6: To a stirred solution of compound-5 (2.7 g, 11.7 mmol) in toluene (10 mL) at −78° C. under nitrogen was added dropwise DIBAL-H (1.7 M in toluene, 13.87 mL). The reaction mixture then was stirred at −78° C. for 20 min. and poured into 0.3N H$_2$SO$_4$ at −10° C. Ethyl acetate was added and the mixture was stirred at room temperature for 30 min. The aqueous layer was extracted thrice with ethyl acetate. The combined organic layers were dried over Na$_2$SO$_4$ and concentrated under vacuum. The residue was purified by column chromatography on 100-200 mesh silica gel and eluted with 1% ethyl acetate/petroleum ether to obtain Compound-6 (840 mg, 30.7%). MS (m/z): [M+H]$^+$, 233.2.

Preparation of Compound-8: To a stirred suspension of NaH (111 mg, 4.64 mol) in dry THF (10 mL) at room temperature under nitrogen was added dropwise a solution of Compound-7 (603 mg, 2.78 mmol) in dry THF (10 mL). The reaction mixture was stirred at room temperature for 20 min. Then a solution of Compound-6 (540 mg, 2.32 mmol) in dry THF (10 mL) was slowly added and the solution was stirred at room temperature for 30 min. The reaction was quenched with a saturated NH$_4$Cl solution. The aqueous layer was extracted thrice with ethyl acetate. The combined organic layers were dried over anhydrous Na$_2$SO$_4$ and concentrated under vacuum. The crude compound was purified by column chromatography on 100-200 mesh silica gel and eluted with 0.3% ethyl acetate/petroleum ether to obtain Compound-8 (430 mg, 62.6%). MS (m/z): [M+H]$^+$, 296.2.

Preparation of QEA-B-002: To a stirred solution of compound-8 (430 mg, 1.45 mmol) in toluene (10 mL) at −78° C. under nitrogen was added dropwise DIBAL-H (1.7 M in toluene, 1.71 mL). The reaction mixture was stirred at −78° C. for 20 min and then poured into 0.3N H$_2$SO$_4$ at −10° C. Ethyl acetate was then added and the mixture was stirred at room temperature for 30 min. The aqueous layer was extracted thrice with ethyl acetate, and the combined organic layers were dried over Na$_2$SO$_4$ and concentrated under vacuum. The residue was purified by column chromatography on 100-200 mesh silica gel and eluted with 0.5% ethyl acetate/petroleum ether to obtain QEA-B-002 (140 mg, 32.2%). $^1$H NMR (CDCl$_3$, 400 MHz): δ 1.13 (s, (H), 1.63-1.70 (m, 4H), 2.11-2.14 (m, 2H0, 2.21-2.25 (m, 2H0, 2.25 (s, 3H), 5.95 (d, J=8 Hz, 1H), 5.97 (d, J=8.4 Hz, 1H), 6.11 (d, J=16 Hz, 1H), 6.23 (d, J=10.8 Hz, 1H), 6.38 (d, J=15.6 Hz, 1H), 6.71 (d, J=15.6 Hz, 1H), 7.18-7.27 (m, 1H), 10.08 (d, J=8.4 Hz, 1H). MS (m/z): [M+H]⁺, 299.2.

TEA-B-003 (5-tert-Butyl-7-(2-methyl-cyclohex-1-enyl)-hepta-2,4,6-trienal)

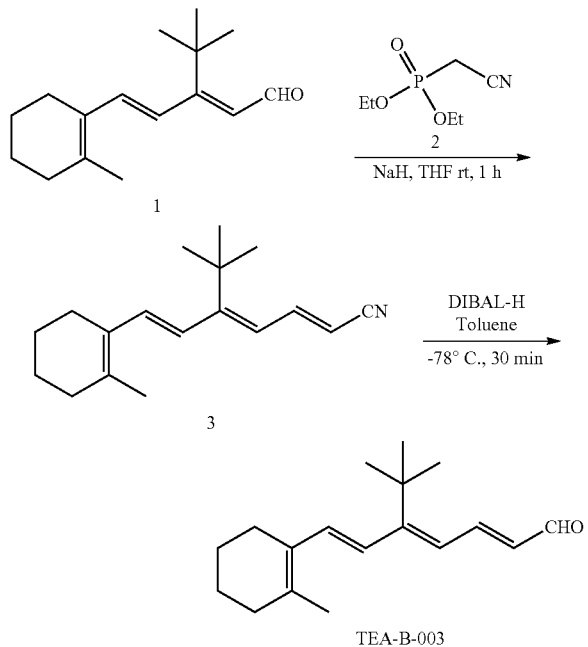

Preparation of Compound-3: To a stirred suspension of NaH (69 mg, 2.87 mmol) in dry THF (10 mL) at room temperature under nitrogen was added dropwise a solution of Compound-2 (517 mg, 2.9 mmol) in dry THF (10 mL). The reaction mixture was stirred at room temperature for 15 min. Then a solution of Compound-1 (450 mg, 1.93 mmol) in dry THF (10 mL) was slowly added and the reaction mixture was stirred at room temperature for 30 min. The reaction was quenched with saturated NH₄Cl solution. The aqueous layer was extracted twice with ethyl acetate, and the combined organic layers were dried over anhydrous Na₂SO₄ and concentrated under vacuum. The crude compound was purified by column chromatography on 100-200 mesh silica gel and eluted with 0.5% ethyl acetate/petroleum ether to obtain Compound-3 (430 mg, 86.9%). MS (m/z): [M+H]⁺, 256.3.

Preparation of TEA-B-003: To a stirred solution of Compound-3 (430 mg, 1.68 mmol) in toluene (10 mL) at −78° C. under nitrogen was added dropwise DIBAL-H (1.7 M in toluene, 2 mL). The reaction mixture was stirred at −78° C. for 30 min and poured into 0.3 M H₂SO₄ at −30° C. Ethyl acetate was added and the mixture then was stirred at room temperature for 1 h. The aqueous layer was extracted thrice with ethyl acetate. The combined organic layers were dried over Na₂SO₄ and concentrated. The residue was purified by column chromatography on 100-200 mesh silica gel and eluted with 0.3% ethyl acetate/petroleum ether to obtain TEA-B-003 (180 mg, 41.3%). ¹H NMR (CDCl₃, 400 MHz): δ 1.15 (s, 9H), 1.58-1.74 (m, 4H), 1.78 (s, 3H), 2.08-2.16 (m, 2H), 2.19-2.24 (m, 2H), 6.11 (d, J=15.6 Hz, 1H), 6.17 (dd, J=8 Hz, 15.2 Hz, 1H), 6.33 (d, J=11.2 Hz, 1H), 6.68 (d, J=16 Hz, 1H), 7.56 (dd, J=10.8 Hz, 15.2 Hz, 1H), 9.66 (d, J=7.2 Hz, 1H)4H), 1.15 (s, 9H); ¹³C NMR (CDCl₃, 100 MHz): δ 19.67, 22.89, 25.65, 29.55, 29.84, 33.40, 37.23, 121.1, 121.4, 127.9, 130.4, 136.7, 152.7, 164.6, 194.6. MS (m/z): [M+H]⁺, 259.3.

TEA-B-001 (5-tert-Butyl-7-(2,6,6-trimethyl-cyclohex-1-enyl)-hepta-2,4,6-trienal)

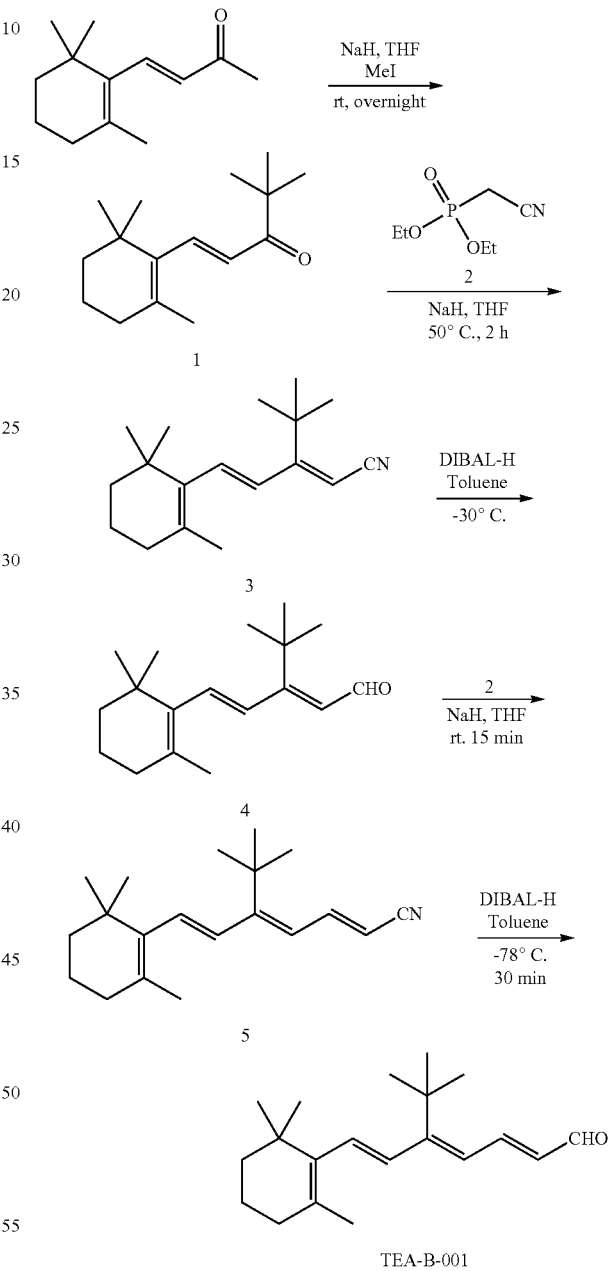

Preparation of Compound-1: To a stirred suspension of NaH (5 g, 0.2 mol) in dry THF (10 mL) at 0° C. was added dropwise a solution of β-ionone (10 g, 52 mmol) in dry THF (10 mL). The reaction mixture was stirred at 0° C. for 2 h. A solution of CH₃I (12.5 mL, 0.2 mol) in dry THF (10 mL) was slowly added and the reaction mixture was stirred at room temperature overnight. The reaction was quenched with an NH₄Cl solution and the mixture was extracted with ethyl acetate (3×200 mL). The combined organic layers were dried over anhydrous Na$_2$SO$_4$ and concentrated. The crude compound was purified by column chromatography on 100-200 mesh silica gel and eluted with 0.5% ethyl acetate/petroleum ether to obtain Compound-1 (5 g, 41%). MS (m/z): [M+H]$^+$, 235.2.

Preparation of Compound-3: To a stirred suspension of NaH (1.54 g, 64 mmol) in dry THF (20 mL) at 0° C. was added dropwise a solution of Compound-2 (11.4 g, 64 mmol) in dry THF (10 mL). The reaction mixture was stirred at 0° C. for 10 min. Then a solution of Compound-1 (5 g, 21 mmol) in dry THF (10 mL) was slowly added. The resulting reaction mixture was stirred at 50° C. for 2 h and then at room temperature for 12 h. The reaction was quenched with an NH$_4$Cl solution and extracted with ethyl acetate. The combined organic layers were dried over anhydrous Na$_2$SO$_4$ and concentrated. The crude compound was purified by column chromatography on 60-120 mesh silica gel and eluted with 0.5% ethyl acetate/petroleum ether to obtain Compound-3 (5 g, 91%). MS (m/z): [M+H]$^+$, 258.2.

Preparation of Compound-4: To a stirred solution of Compound-3 (5.3 g, 20.6 mmol) in dry toluene (53 mL) at −30° C. under nitrogen was added dropwise DIBAL-H (1.7 M in toluene, 24 mL). The reaction mixture was cooled to −10° C. and poured onto wet silica gel. The resulting mixture was stirred for 30 minutes and filtered. The silica bed was washed twice with ether and the filtrate was concentrated. The residue was purified by column chromatography on 60-120 mesh silica gel and eluted with 0.8% ethyl acetate/petroleum ether to obtain Compound-4 (1.53 g, 28.5%). MS (m/z): [M+H]$^+$, 261.2.

Preparation of Compound-6: To a stirred suspension of NaH (133 mg, 5.54 mmol) in dry THF (20 mL) at room temperature under nitrogen was added dropwise a solution of Compound-2 (0.98 g, 5.53 mmol) in dry THF (10 mL). The reaction mixture was stirred at room temperature for 15 min and then a solution of Compound-4 (970 mg, 3.72 mmol) in dry THF (10 mL) was slowly added. The reaction mixture was stirred at room temperature for 15 min and the reaction was quenched with an NH$_4$Cl solution. The mixture was extracted with ethyl acetate. The combined organic layers were dried over anhydrous Na$_2$SO$_4$ and concentrated. The crude compound was purified by column chromatography on 100-200 mesh silica gel and eluted with 0.2% ethyl acetate/petroleum ether to obtain Compound-6 (550 mg, 51.5%). MS (m/z): [M+H]$^+$, 284.3.

Preparation of TEA-B-001: To a stirred solution of Compound-6 (550 mg, 1.94 mmol) in dry toluene (10 mL) cooled to −78° C. under nitrogen was added dropwise DIBAL-H (1.7 M in toluene, 2.28 mL). The reaction mixture was stirred at −78° C. for 30 min and quenched with a 0.3 M H$_2$SO$_4$ solution and extracted with ethyl acetate. The combined organic layers were dried over anhydrous Na$_2$SO$_4$ and concentrated. The crude compound was purified by column chromatography on 100-200 mesh silica gel and eluted with 0.1% ethyl acetate/petroleum ether to obtain TEA-B-001 (180 mg, 32.4%). $^1$H NMR (CDCl$_3$, 400 MHz): δ 1.05 (s, 6H), 1.16 (s, 9H), 1.47-1.51 (m, 2H), 1.62-1.66 (m, 2H), 1.79 (s, 3H), 2.04 (t, J=6.4 Hz, 2H), 6.04 (s, 1H), 6.05 (m, 1H), 6.19 (dd, J=8 Hz, 15.2 Hz, 1H), 6.33 (d, J=11.2 Hz, 1H), 7.64 (dd, J=11.2 Hz, 15.2 Hz, 1H), 9.53 (d, J=8 Hz, 1H); $^{13}$C NMR (CDCl$_3$, 100 MHz): δ 19.37, 22.14, 29.16, 29.77, 33.14, 34.46, 37.17, 39.60, 110.0, 121.3, 129.5, 130.6, 130.7, 136.9, 137.8, 152.5, 163.9, 194.5. MS (m/z): [M+H]$^+$, 287.2.

LIST OF ABBREVIATIONS

DIBAL-H: diisobutylaluminium hydride;
DCM: dichloromethane;
m-CPBA: m-chloroperbenzoic acid
Met: methanol;
THF: tetrahydrofuran;
p-TSA: para-toluenesulfonic acid;
TEA: triethylamine;
t-BuOK: potassium tert-butoxide;
LAH$_4$: lithium aluminum hydride;
PDC: pyridium dichromate;
NBS: N-bromosuccinimide;
AIBN: azobisisobutyronitrile;
TEP: triethylphosphate;
Pd/C: palladium on carbon;
DMF: dimethylformate;
TBDMSCl: tert-butyldimethylsilyl chloride;
DMAP: dimethylaminopyridine;
i-PrCOCl: isobutyryl chloride;
BF$_3$·Et$_2$O: boron trifluoride diethyl etherate;
i-PrNEt: diisopropylethyl amine;
CH$_3$MgBr: methylmagnesium bromide.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating an ocular disorder in a subject associated with increased all-trans-retinal in an ocular tissue, the method comprising:
    administering to the subject a therapeutically effective amount of a primary amine compound of formula (I):

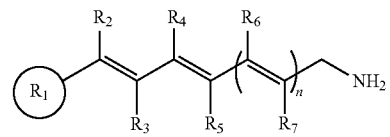

wherein R$_1$ is a cyclic or polycyclic ring, wherein the ring is a substituted or unsubstituted aryl, heteroaryl, cycloalkyl, or heterocyclyl;

n=1-3;

where R$_2$, R$_3$, R$_5$, R$_6$, and R$_7$, are each individually hydrogen, a substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O) (C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$) aryloxycarbonyl, C$_2$-C$_{24}$ alkylcarbonato, C$_6$-C$_{20}$) arylcarbonato, carboxy, carboxylato, carbamoyl, C$_1$-C$_{24}$ alkyl-carbamoyl, arylcarbamoyl, thiocarbamoyl, carbamido, cyano, isocyano, cyanato, isocyanato, isothiocyanato, azido, formyl, thioformyl, amino, C$_1$-C$_{24}$ alkyl amino, C$_5$-C$_{20}$ aryl amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, C$_5$-C$_{20}$ arylsulfinyl, C$_1$-C$_{24}$ alkylsulfonyl, C$_5$-C$_{20}$ arylsulfonyl, phosphono, phosphonato, phosphinato, phospho, or phosphino or combinations thereof;

where R₄ is a t-butyl or aryl group;
and pharmaceutically acceptable salts thereof;
and wherein the primary amine compound has an RPE65 IC$_{50}$ greater than 10 μM.

2. The method of claim 1, the primary amine compound upon administration to the subject transiently sequestering all-trans-retinal in ocular tissue of a subject by forming a reversible Schiff-base with the all-trans-retinal, wherein the primary amine compound does not adversely affect normal retinoid cycle performance.

3. The method of claim 1, the primary amine capable of serving as a substrate of enzymatic LRAT.

4. The method of claim 1, the therapeutically effective amount of the primary amine compound comprising an amount effective to inhibit bright light-induced retinal damage in a Rdh8$^{-/-}$Abca4$^{-/-}$ mouse.

5. The method of claim 1, the primary amine compound when administered to a Rdh8$^{-/-}$Abca4$^{-/-}$ mouse increasing the optical coherence tomography score of the mouse in comparison to untreated control animal.

6. The method of claim 1, the primary amine compound being delivered to the subject by at least one of topical administration, systemic administration, intravitreal injection, and intraocular delivery.

7. The method of claim 1, the primary amine being provided in an ocular preparation for sustained delivery.

8. The method of claim 1, the ocular disorder comprising at least one of light induced retinal degeneration, macular degeneration, Stargardt's disease, and retinitis pigmentosa.

9. The method of claim 1, the primary amine compound not causing night blindness in the subject.

10. The method of claim 1, wherein the primary amine compound is selected from the group consisting of:

QEA-B-001-NH2

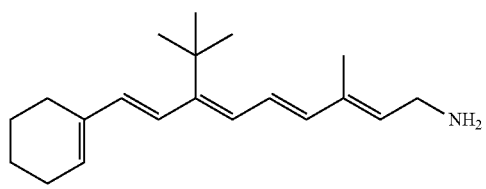

QEA-B-002-NH2

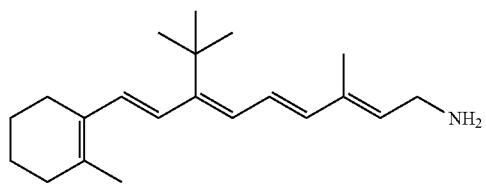

QEA-B-003-NH2

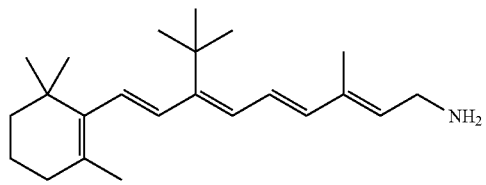

QEA-B-004-NH2

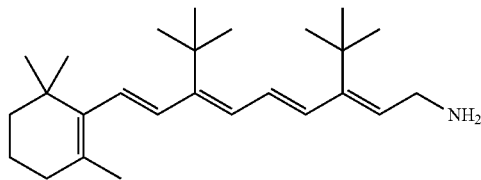

QEA-B-005-NH2

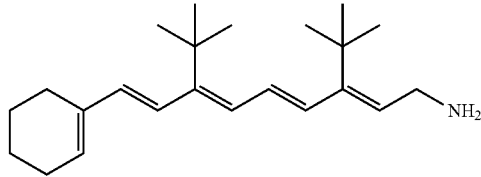

QEA-C-001-NH2

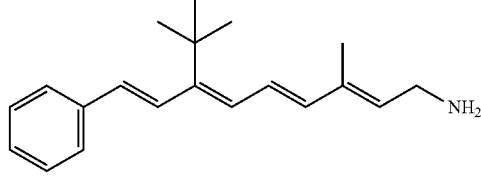

QEA-C-002-NH2

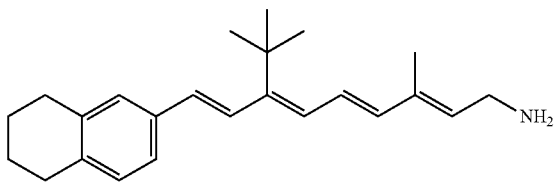

QEA-C-003-NH2

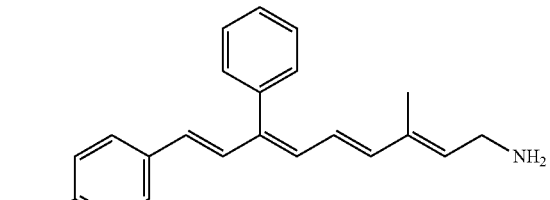

QEA-C-004-NH2

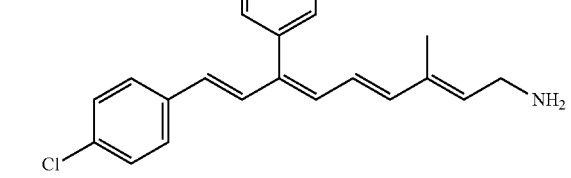

QEA-C-005-NH2
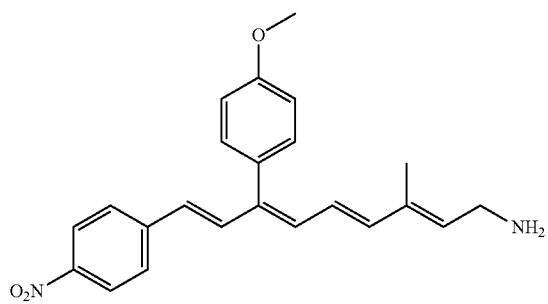
QEA-C-006-NH2
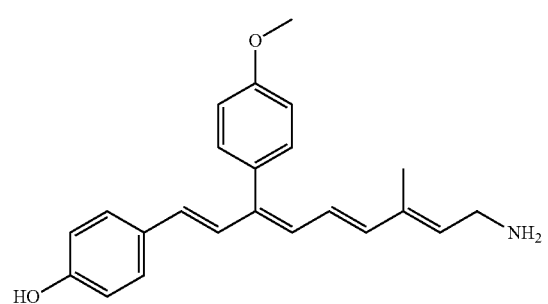
QEA-E-001-NH2
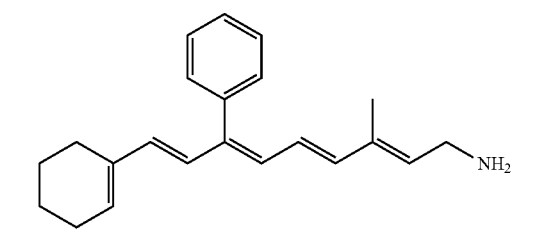
QEA-E-002-NH2
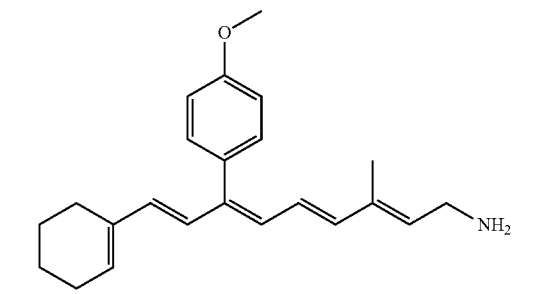
QEA-G-002-NH2
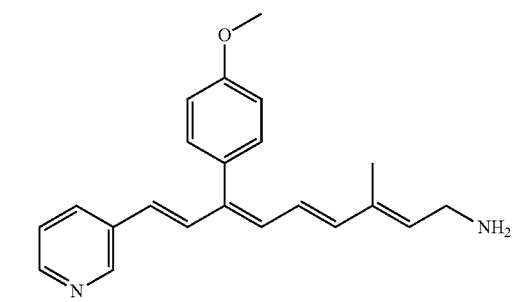
TEA-B-001-NH2
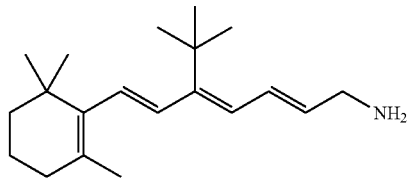
TEA-B-002-NH2
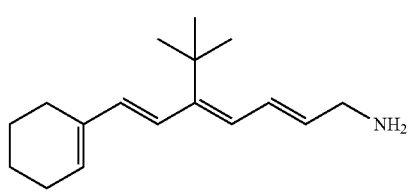
TEA-B-003-NH2
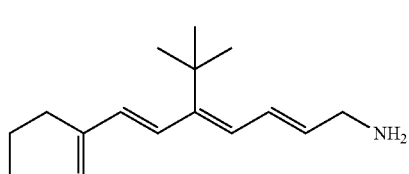
TEA-B-004-NH2
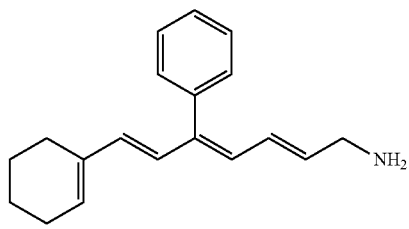
TEA-C-001-NH2
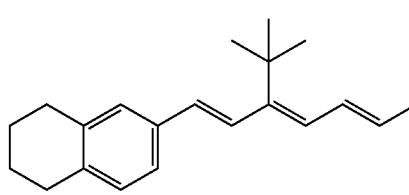
TEA-C-002-NH2
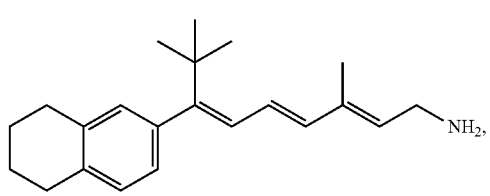
and
pharmaceutically acceptable salts thereof.
11. A method of treating Stargardt disease in a subject, the method comprising:
administering to the subject a therapeutically effective amount of a primary amine compound of formula (I):

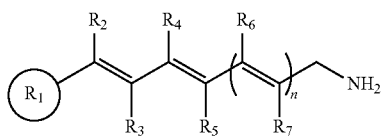

wherein R₁ is a cyclic or polycyclic ring, wherein the ring is a substituted or unsubstituted aryl, heteroaryl, cycloalkyl, or heterocyclyl;

n=1-3;

where $R_2$, $R_3$, $R_5$, $R_6$, and $R_7$, are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$) aryloxycarbonyl, $C_2$-$C_{24}$ alkylcarbonato, $C_6$-$C_{20}$) arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{24}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

where $R_4$ is a t-butyl or aryl group;

and pharmaceutically acceptable salts thereof;

and wherein the primary amine compound has an RPE65 IC$_{50}$ greater than 10 μM.

12. The method of claim 11, the primary amine compound upon administration to the subject transiently sequestering all-trans-retinal in ocular tissue of a subject by forming a reversible Schiff-base with the all-trans-retinal, wherein the primary amine compound does not adversely affect normal retinoid cycle performance.

13. The method of claim 11, the primary amine capable of serving as a substrate of enzymatic LRAT.

14. The method of claim 11, the therapeutically effective amount of the primary amine compound comprising an amount effective to inhibit bright light-induced retinal damage in a Rdh8$^{-/-}$Abca4$^{-/-}$ mouse.

15. The method of claim 11, the primary amine compound when administered to a Rdh8$^{-/-}$Abca4$^{-/-}$ mouse increasing the optical coherence tomography score of the mouse in comparison to untreated control animal.

16. The method of claim 11, the primary amine compound being delivered to the subject by at least one of topical administration, systemic administration, intravitreal injection, and intraocular delivery.

17. The method of claim 11, the primary amine being provided in an ocular preparation for sustained delivery.

18. The method of claim 11, the primary amine compound not causing night blindness in the subject.

19. The method of claim 11, wherein the primary amine compound is selected from the group consisting of:

QEA-B-001-NH2

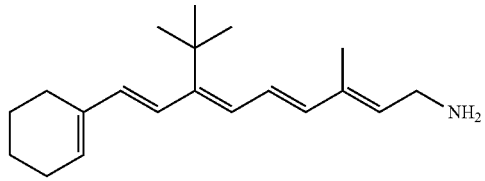

QEA-B-002-NH2

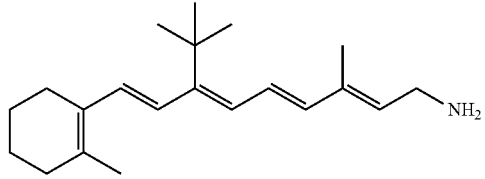

QEA-B-003-NH2

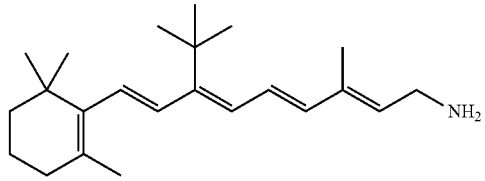

QEA-B-004-NH2

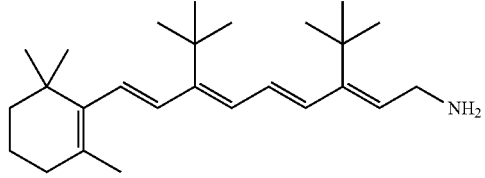

QEA-B-005-NH2

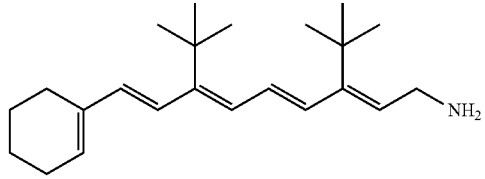

QEA-C-001-NH2

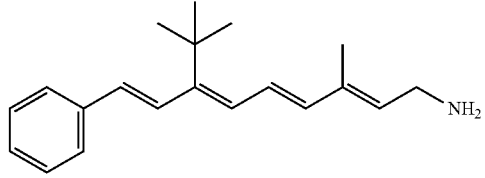

QEA-C-002-NH2

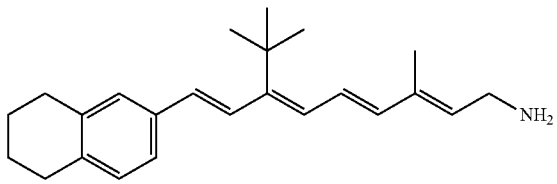

QEA-C-003-NH2
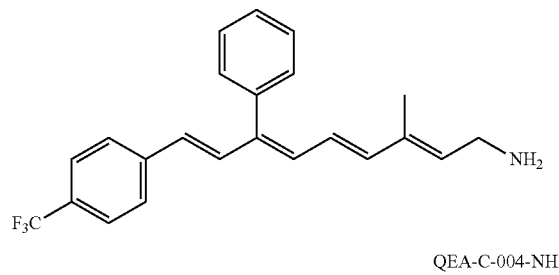
QEA-C-004-NH2
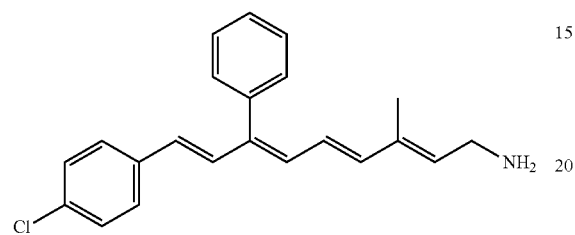
QEA-C-005-NH2
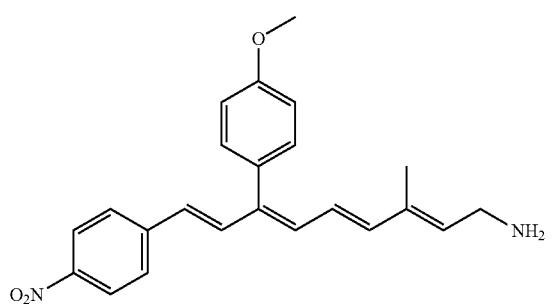
QEA-C-006-NH2
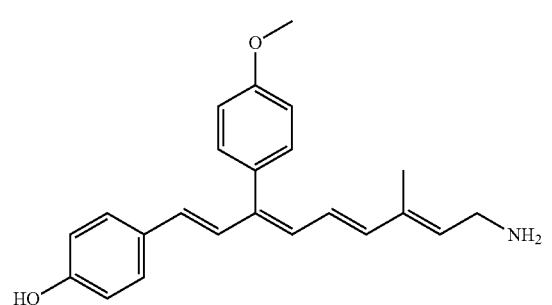
QEA-E-001-NH2
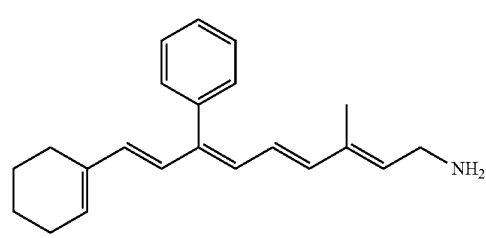
QEA-E-002-NH2
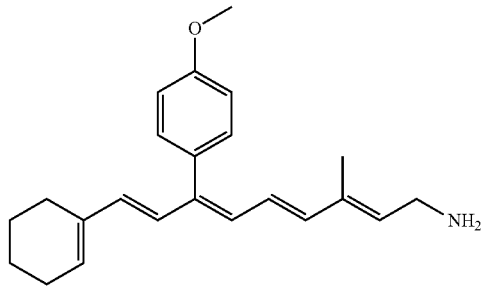
QEA-G-002-NH2
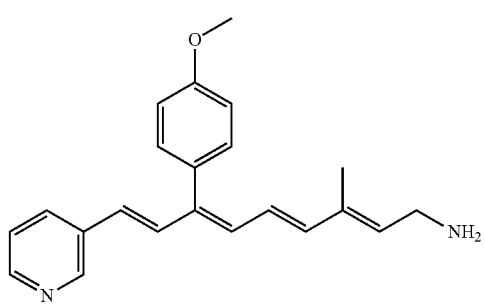
TEA-B-001-NH2
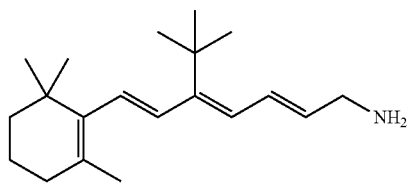
TEA-B-002-NH2
TEA-B-003-NH2

-continued

TEA-B-004-NH2

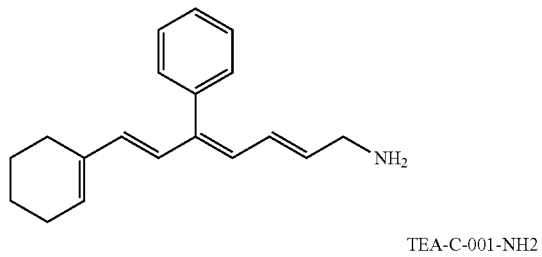

TEA-C-001-NH2

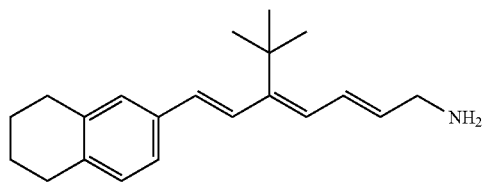

TEA-C-002-NH2

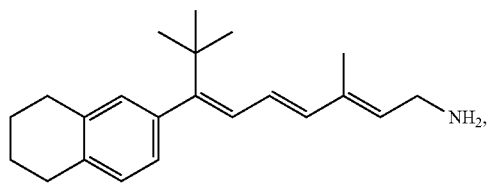

and
pharmaceutically acceptable salts thereof.

20. The method of claim 1, where n is 1.
21. The method of claim 20, wherein the primary amine compound is

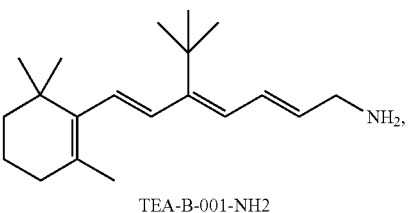 [SMILES: CC1=C(/C=C/C(=C/C=C/CN)C(C)(C)C)C(C)(C)CCC1]

TEA-B-001-NH2 and pharmaceutically
acceptable salts thereof.

22. The method of claim 11, where n is 1.
23. The method of claim 22, wherein the primary amine compound is

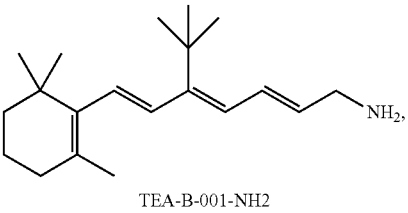 [SMILES: CC1=C(/C=C/C(=C/C=C/CN)C(C)(C)C)C(C)(C)CCC1]

TEA-B-001-NH2 and pharmaceutically
acceptable salts thereof.

* * * * *